(12) United States Patent  
Rajamani et al.

(10) Patent No.: US 8,691,757 B2  
(45) Date of Patent: Apr. 8, 2014

(54) HEPATITIS C VIRUS INHIBITORS

(75) Inventors: Ramkumar Rajamani, Woodbridge, CT (US); Kishore V. Renduchintala, Bangalore (IN); Kandhasamy Sarkunam, Hosur (IN); Pulicharla Nagalakshmi, Bangalore (IN); Nicholas A. Meanwell, East Hampton, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 106 days.

(21) Appl. No.: 13/492,982

(22) Filed: Jun. 11, 2012

(65) Prior Publication Data  
US 2013/0142754 A1 Jun. 6, 2013

Related U.S. Application Data

(60) Provisional application No. 61/497,141, filed on Jun. 15, 2011.

(51) Int. Cl.  
*A61K 38/00* (2006.01)  
*A01N 37/18* (2006.01)

(52) U.S. Cl.  
USPC .............................. 514/3.7; 514/4.3

(58) Field of Classification Search  
None  
See application file for complete search history.

(56) References Cited

U.S. PATENT DOCUMENTS

| | | | |
|---|---|---|---|
| 5,223,432 A | 6/1993 | Wirz et al. | |
| 6,608,027 B1 * | 8/2003 | Tsantrizos et al. | 514/4.3 |
| 7,449,479 B2 | 11/2008 | Wang et al. | |
| 7,582,605 B2 | 9/2009 | Moore et al. | |
| 7,601,709 B2 | 10/2009 | Miao et al. | |
| 7,605,126 B2 | 10/2009 | Niu et al. | |
| 7,635,683 B2 | 12/2009 | Gai et al. | |
| 7,915,291 B2 | 3/2011 | Wang et al. | |
| 8,232,246 B2 | 7/2012 | McDaniel et al. | |
| 8,268,776 B2 | 9/2012 | Sun et al. | |
| 8,299,094 B2 | 10/2012 | Wang et al. | |
| 8,309,685 B2 | 11/2012 | Petter et al. | |
| 8,338,606 B2 | 12/2012 | Perrone et al. | |
| 2005/0209135 A1 | 9/2005 | Busacca et al. | |
| 2006/0199773 A1 | 9/2006 | Sausker et al. | |
| 2006/0257980 A1 | 11/2006 | Li | |
| 2007/0078081 A1 | 4/2007 | Casarez et al. | |
| 2008/0279821 A1 | 11/2008 | Niu et al. | |
| 2012/0330019 A1 | 12/2012 | Wang et al. | |

FOREIGN PATENT DOCUMENTS

| | | |
|---|---|---|
| WO | WO 98/17679 | 4/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |

(Continued)

OTHER PUBLICATIONS

Lauer, G.M. et al., "Hepatitis C Virus Infection", The New England Journal of Medicine, vol. 345, No. 1, pp. 41-52 (2001).

Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).

Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).

Ribeiro, C.M.R. et al., "Ultrasound in enzymatic resolution of ethyl 3-hydroxy-3-phenylpropanoate", Tetrahedron Letters, vol. 42, pp. 6477-6479 (2001).

(Continued)

*Primary Examiner* — Thomas Heard  
(74) *Attorney, Agent, or Firm* — Pamela A. Mingo

(57) ABSTRACT

Hepatitis C virus inhibitors having the general formula (I)

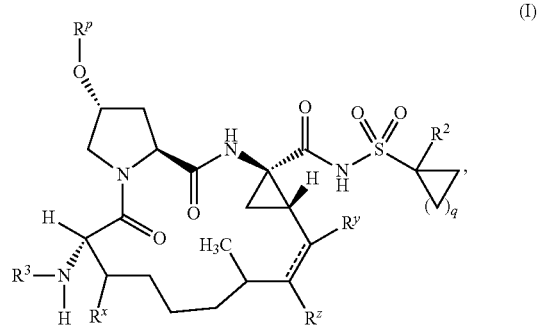

are disclosed. Compositions comprising the compounds and methods for using the compounds to inhibit HCV are also disclosed.

18 Claims, No Drawings

(56) References Cited

FOREIGN PATENT DOCUMENTS

| | | |
|---|---|---|
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/005565 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106130 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/005677 | 1/2009 |
| WO | WO 2009/005690 | 1/2009 |
| WO | WO 2009/010804 | 1/2009 |
| WO | WO 2009/014730 | 1/2009 |
| WO | WO 2009/070692 | 6/2009 |
| WO | WO 2009/082701 | 7/2009 |
| WO | WO 2009/085659 | 7/2009 |
| WO | WO 2009/129109 | 10/2009 |
| WO | WO 2009/140475 | 11/2009 |
| WO | WO 2009/140500 | 11/2009 |
| WO | WO 2009/142842 | 11/2009 |
| WO | WO 2009/146347 | 12/2009 |
| WO | WO 2010/031829 | 3/2010 |
| WO | WO 2010/031832 | 3/2010 |
| WO | WO 2010/036551 | 4/2010 |
| WO | WO 2010/036871 | 4/2010 |
| WO | WO 2010/036896 | 4/2010 |
| WO | WO 2010/065577 | 6/2010 |
| WO | WO 2010/077783 | 7/2010 |
| WO | WO 2011/002807 | 1/2011 |
| WO | WO 2011/005646 | 1/2011 |
| WO | WO 2011/038283 | 3/2011 |
| WO | WO 2011/038293 | 3/2011 |
| WO | WO 2011/046811 | 4/2011 |
| WO | WO 2011/063502 | 6/2011 |
| WO | WO 2011/072370 | 6/2011 |
| WO | WO 2012/018829 | 2/2012 |
| WO | WO 2012/040242 | 3/2012 |
| WO | WO 2009/148923 | 4/2012 |
| WO | WO 2012/092411 | 7/2012 |
| WO | WO 2012/151195 | 11/2012 |
| WO | WO 2012/166459 | 12/2012 |

OTHER PUBLICATIONS

Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).

Wirz, B. et al., "Enzymatic preparation of homochiral 2-isobutyl succinic acid derivatives", Tetrahedron: Asymmetry, vol. 8, No. 2, pp. 187-189 (1997).

Yang, S., "Chemoenzymatic Synthesis of (R)-(—)-Citramalic Acid", Synthesis, pp. 365-366 (1992).

* cited by examiner

HEPATITIS C VIRUS INHIBITORS

CROSS-REFERENCE TO RELATED APPLICATIONS

This application claims the benefit of U.S. Provisional Application Ser. No. 61/497,141 filed Jun. 15, 2011.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with additional compounds having anti-HCV activity.

In its first aspect the present disclosure provides a compound of formula (I):

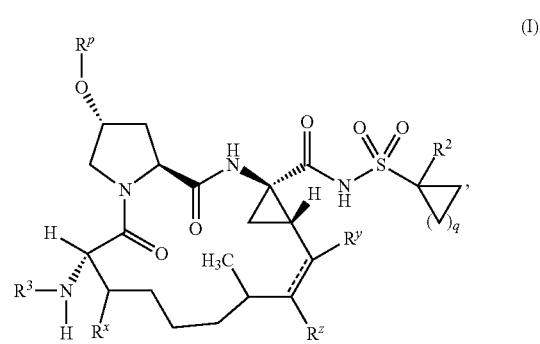

or a pharmaceutically acceptable salt thereof, wherein q is 1 or 2;

==== is a single or double bond;

$R^p$ is selected from

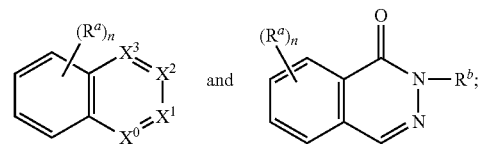

wherein $R^p$ is attached to the parent molecular moiety through any substitutable carbon atom in the group;

n is 0, 1, 2, 3, 4, 5, or 6;

$X^0$ is selected from CH and N;

$X^1$ is selected from CH and N;

$X^2$ and $X^3$ are independently selected from CH, C($R^a$) and N; provided that at least one of $X^1$, $X^2$, and $X^3$ is other than N;

each $R^a$ is independently selected from alkenyloxy, alkoxy, alkoxyalkoxy, alkyl, benzodioxanyl, carboxamido, carboxy, carboxyalkoxy, cyano, cycloalkylalkoxy, cycloalkyloxy, deuteroalkoxy, dialkylamino, halo, haloalkyl, haloalkoxy, haloalkoxycarbonyl, hydroxy, morpholinyl, phenyl, piperazinyl, pyrazolyl, pyridinyl, and pyrrolidinyl, wherein the morpholinyl, the phenyl, the piperazinyl, the pyridinyl, and the pyrrolidinyl are optionally substituted with one or two groups independently selected from alkoxy, alkyl, alkylsulfonyl, halo, haloalkoxy, haloalkyl, and morpholinyl; and wherein two adjacent $R^a$ groups, together with the carbon atoms to which they are attached, can optionally form a ring selected from dioxanyl, dioxolanyl, morpholinyl, pyranyl, and phenyl, wherein the ring is optionally substituted with one or two groups independently selected from alkyl and halo;

$R^b$ is alkyl;

$R^x$ is selected from methyl and ethyl;

$R^y$ and $R^z$ are independently selected from hydrogen and hydroxy; provided that when ==== is a double bond, $R^y$ and $R^z$ are each hydrogen;

$R^2$ is selected from hydrogen, alkyl, halo, haloalkoxy, haloalkyl, and hydroxyalkyl; and $R^3$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl.

In a first embodiment of the first aspect the present disclosure provides a compound of formula (I), or a pharmaceutically acceptable salt thereof, wherein:

q is 1;

==== is a double bond;

$R^x$ is methyl; and $R^y$ and $R^z$ are each hydrogen.

In a second embodiment of the first aspect the present disclosure provides a compound of formula (I), or a pharmaceutically acceptable salt thereof, wherein $R^p$ is:

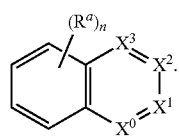

In a third embodiment the present disclosure provides a compound of formula (I), or a pharmaceutically acceptable salt thereof, wherein:

$R^p$ is

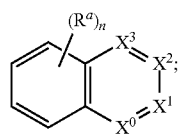

n is 0, 1, 2, or 3;

each $R^a$ is independently selected from alkoxy, and halo; and $R^3$ is selected from alkoxycarbonyl and haloalkoxycarbonyl.

In a second aspect the present disclosure provides a compound of formula (II)

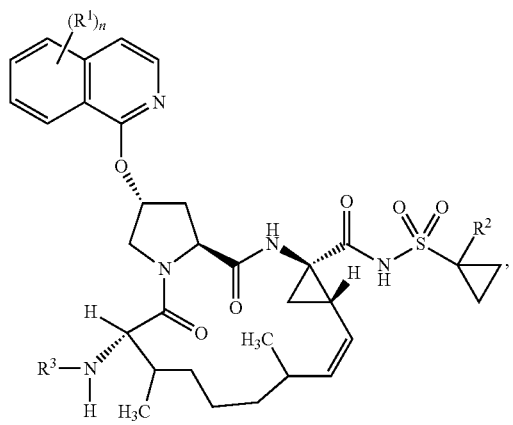

or a pharmaceutically acceptable salt thereof, wherein n is 0, 1, 2, 3, 4, 5, or 6;

each $R^1$ is independently selected from alkoxy, alkyl, carboxamido, carboxy, cyano, cycloalkyloxy, dialkylamino, halo, haloalkyl, haloalkoxy, and phenyl, wherein the phenyl is optionally substituted with one or two groups independently selected from alkoxy, alkyl, halo, haloalkoxy, and haloalkyl;

$R^2$ is selected from hydrogen, alkyl, halo, and haloalkyl; and $R^3$ is selected from alkoxycarbonyl, alkylcarbonyl, haloalkoxycarbonyl, haloalkylcarbonyl, and phenylcarbonyl, wherein the phenyl is optionally substituted with one or two groups independently selected from alkyl and halo.

In a third aspect the present disclosure provides a composition comprising a compound of formula (I), or a pharmaceutically acceptable salt thereof, and a pharmaceutically acceptable carrier. In a first embodiment of the third aspect the present disclosure provides a composition comprising a compound of formula (I), or a pharmaceutically acceptable salt thereof, at least one additional compound having anti-HCV activity, and a pharmaceutical carrier. In a second embodiment at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the third aspect the present disclosure provides a composition comprising a compound of formula (I), or a pharmaceutically acceptable salt thereof, at least one additional compound having anti-HCV activity, and a pharmaceutical carrier, wherein at least one of the additional compounds is selected from interleukin 2, interleukin 6, interleukin 12, Imiquimod, ribavirin, an inosine 5'-monophosphate dehydrogenase inhibitor, amantadine, and rimantadine. In a fifth embodiment of the third aspect the present disclosure provides a composition comprising a compound of formula (I), or a pharmaceutically acceptable salt thereof, at least one additional compound having anti-HCV activity, and a pharmaceutical carrier, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a method of treating an HCV infection in a patient, comprising administering to the patient a therapeutically effective amount of a compound of formula (I), or a pharmaceutically acceptable salt thereof. In a first embodiment of the fourth aspect the method further comprises administering at least one additional compound having anti-HCV activity prior to, after, or simultaneously with the compound of formula (I), or a pharmaceutically acceptable salt thereof. In a second embodiment of the fourth aspect at least one of the additional compounds is an interferon or a ribavirin. In a third embodiment the interferon is selected from interferon alpha 2B, pegylated interferon alpha, consensus interferon, interferon alpha 2A, and lymphoblastiod interferon tau. In a fourth embodiment of the fourth aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, Imiquimod, ribavirin, an inosine 5'-monophosphate dehydrogenase inhibitor, amantadine, and rimantadine. In a fifth embodiment of the fourth aspect the present disclosure provides a method of treating an HCV infection in a patient, comprising administering to the patient a therapeutically effective amount of a compound of formula (I), or a pharmaceutically acceptable salt thereof, and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substitutent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^1$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkoxy," as used herein, refers to an alkyl group attached to the parent molecular moiety through an oxygen atom.

The term "alkoxyalkoxy," as used herein, refers to an alkoxyalkyl group attached to the parent molecular moiety through an oxygen atom.

The term "alkoxyalkoxycarbonyl," as used herein, refers to an alkoxyalkoxy group attached to the parent molecular moiety through a carbonyl group.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylamino," as used herein, refers to —NHR$^q$, wherein R$^q$ is alkyl.

The term "alkylaminocarbonyl," as used herein, refers to an alkylamino group attached to the parent molecular moiety through a carbonyl group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "carbonyl," as used herein, refers to —C(O)—.

The term "carboxamido," as used herein, refers to —C(O)NR$^x$R$^y$, wherein R$^x$ and R$^y$ are independently selected from hydrogen and alkyl.

The term "carboxy," as used herein, refers to —CO$_2$H.

The term "carboxyalkoxy," as used herein, refers to a carboxyalkyl group attached to the parent molecular moiety through an oxygen atom.

The term "carboxyalkyl," as used herein, refers to an alkyl group substituted with one, two, or three carboxy groups.

The term "cyano," as used herein, refers to —CN.

The term "cycloalkyl," as used herein, refers to a saturated monocyclic or bicyclic hydrocarbon ring system having three to seven carbon atoms and zero heteroatoms. Representative examples of cycloalkyl groups include, but are not limited to, cyclopropyl, cyclobutyl, and cyclopentyl.

The term "cycloalkylalkoxy," as used herein, refers to a (cycloalkyl)alkyl group attached to the parent molecular moiety through an oxygen atom.

The term "cycloalkylalkoxycarbonyl," as used herein, refers to a cycloalkylalkoxy group attached to the parent molecular moiety through a carbonyl group.

The term "(cycloalkyl)alkyl," as used herein, refers to an alkyl group substituted with one, two, or three cycloalkyl groups.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The term "deuteroalkoxy," as used herein, refers to an alkoxy group wherein at least one of the hydrogen atoms is replaced by a deuterium atom.

The term "deuteroalkoxycarbonyl," as used herein, refers to a deuteroalkoxy group attached to the parent molecular moiety through a carbonyl group.

The term "deuterohaloalkoxy," as used herein, refers to a haloalkoxy group where at least one of the hydrogen atoms is replaced by a deuterium atom.

The term "deuterohaloalkoxycarbonyl," as used herein, refers to a deuterohaloalkoxy group attached to the parent molecular moiety through a carbonyl group.

The term "dialkylamino," as used herein, refers to —NR$^p$R$^q$, wherein R$^p$ and R$^q$ are alkyl groups. The alkyl groups may be the same or different.

The term "dialkylaminocarbonyl," as used herein, refers to a dialkylamino group attached to the parent molecular moiety through a carbonyl group.

The term "dialkylaminocarbonylcarbonyl," as used herein, refers to a dialkylaminocarbonyl group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylcarbonyl," as used herein, refers to a haloalkyl group attached to the parent molecular moiety through a carbonyl group.

The term "haloalkylamino," as used herein, refers to —NHR$^q$, wherein R$^q$ is a haloalkyl group.

The term "haloalkylaminocarbonyl," as used herein, refers to a haloalkylamino group attached to the parent molecular moiety through a carbonyl group.

The term "haloalkylcarbonyl," as used herein, refers to a haloalkyl group attached to the parent molecular moiety through a carbonyl group.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group; and tricyclic groups in which a bicyclic system is fused to a phenyl group, a monocyclic cycloalkenyl group, a monocyclic cycloalkyl group, or another monocyclic heterocyclyl group. The heterocyclyl groups of the present invention can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "phenylcarbonyl," as used herein, refers to a phenyl group attached to the parent molecular moiety through a carbonyl group.

The term "phenyloxy," as used herein, refers to a phenyl group attached to the parent molecular moiety through an oxygen atom.

The term "phenyloxycarbonyl," as used herein, refers to a phenyloxy group attached to the parent molecular moiety through a carbonyl group.

The term "sulfonyl," as used herein, refers to —SO$_2$—.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

Asymmetric centers exist in the compounds of the present disclosure. For example, the compounds may include P1 cyclopropyl element of formula

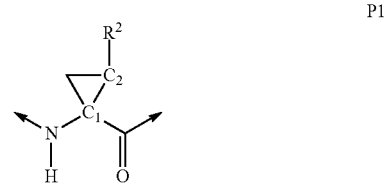

wherein $C_1$ and $C_2$ each represent an asymmetric carbon atom at positions 1 and 2 of the cyclopropyl ring.

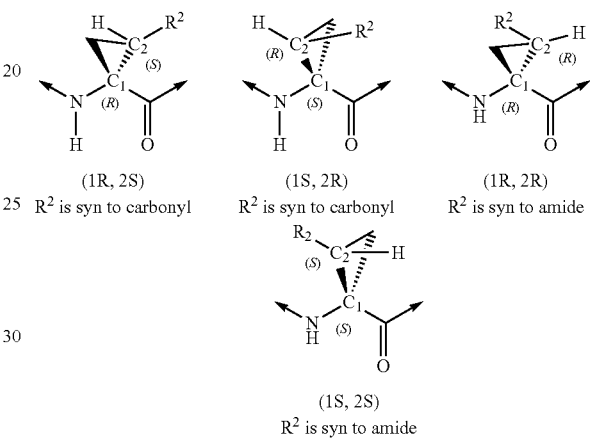

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidyl-cholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |

TABLE 1-continued

| Brand Name | Physiological Class | Type of Inhibitor or Target | Source Company |
|---|---|---|---|
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |

TABLE 1-continued

| Brand Name | Physiological Class | Type of Inhibitor or Target | Source Company |
|---|---|---|---|
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Scheringng-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |

TABLE 1-continued

| Brand Name | Physiological Class | Type of Inhibitor or Target | Source Company |
|---|---|---|---|
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| INX-189 | Antiviral | Nucleotide NS5B Polymerase Inhibitor | Inhibitex |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: $Et_2O$ for diethyl ether; h or hr or hrs for hours; min or mins for minutes; THF for tetrahydrofuran; TBME for methyl tert-butyl ether; DMAP for N,N-dimethylaminopyridine; LiHMDS for lithium hexamethyldisilzide; DCM for dichloromethane; DIPEA for diisopropylethylamine; Boc for tert-butoxycarbonyl; pet ether for petroleum ether; DMSO for dimethylsulfoxide; rt or RT or Rt for room temperature or retention time (context will dictate); IPA for isopropyl alcohol; t-BuO for tert-butoxy; HATU for O-(7-azabenzotriazol-1-yl)-N,N,N',N'-tetramethyluronium hexafluorophosphate; EtOAc for ethyl acetate; TMS for trimethylsilyl; DPPA for diphenylphosphoryl azide; Me for methyl; OAc for acetate; n-Bu for n-butyl; DAST for (diethylamino)sulfur trifluoride; and TFA for trifluoroacetic acid.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

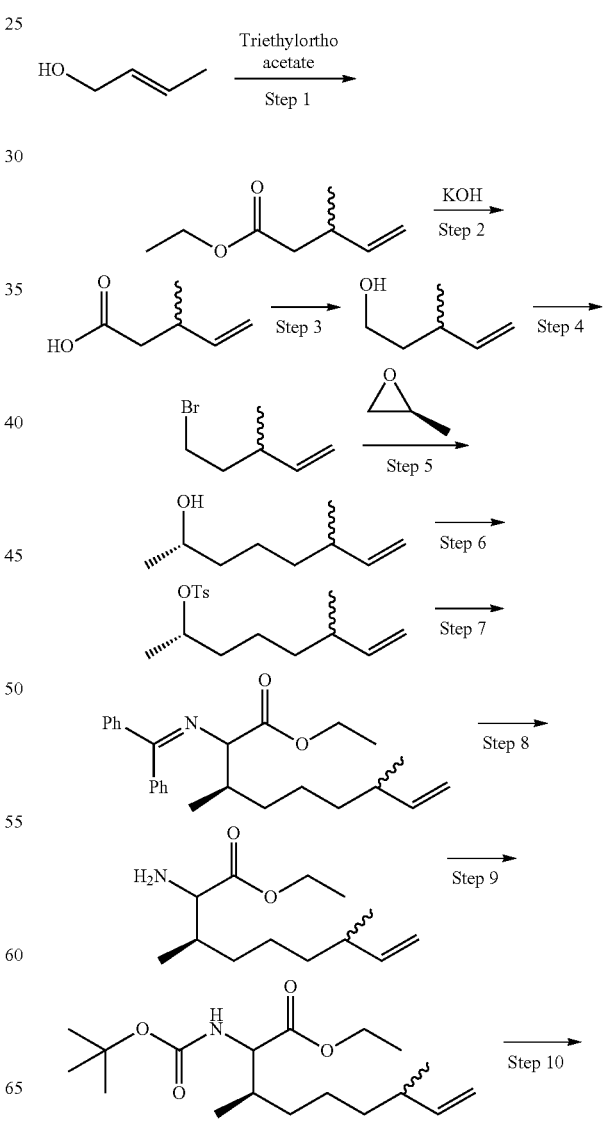

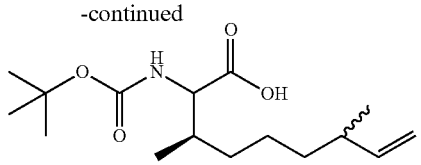

Step 1: Preparation of ethyl 3-methylpent-4-enoate

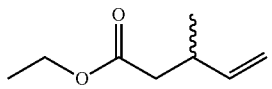

To a solution of (E)-but-2-en-1-ol (50 g, 693 mmol) in 1,1,1-triethoxyethane (890 mL 4854 mmol) was added acetic acid (5 g, 83 mmol) at room temperature. The reaction was heated to 125° C. for 4 h. The by-product ethanol was distilled by normal distillation to get crude compound ethyl 3-methylpent-4-enoate (70 g, 71.0%) as color less oil. This was taken to next step without further purification; $^1$H NMR (DMSO-$d_6$) δ ppm 5.82-5.73 (m, 1H), 5.03-4.92 (m, 2H), 4.08-4.02 (m, 2H), 2.50 (m, 1H), 2.31-2.26 (m, 2H), 1.17 (t, J=8 Hz, 3H), 1.00 (d, J=8 Hz, 3H).

Step 2: Preparation of 3-methyl pent-4-enoic acid

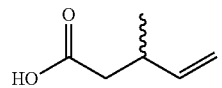

To a solution of ethyl 3-methylpent-4-enoate (70 g, 492 mmol) in methanol (500 mL) was added KOH (41.4 g, 738 mmol) at room temperature. The reaction mass was heated to reflux for 18 h. The reaction mass was distilled under reduced pressure. Ether (750 ml) was added to the residue, washed with saturated sodium bicarbonate solution (350 mL×3). Combined aqueous layer was acidified using con. HCl (250 mL), extracted with DCM (500 mL×3). Combined organic layer was dried over anhydrous sodium sulphate and concentrated under reduced pressure to get crude compound 3-methylpent-4-enoic acid (52 g, 93%) as brown oil; $^1$H NMR (DMSO-$d_6$) δ ppm 12.04 (s, br, 1H), 5.84-5.75 (m, 1H), 5.03-4.92 (m, 2H), 2.56-2.50 (m, 1H), 2.28-2.22 (m, 2H), 1.00 (d, J=8 Hz, 3H).

Step 3: Preparation of 3-methyl pent-4-ene-1-ol

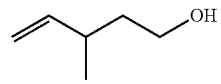

To a suspension of lithium aluminum hydride (6.03 g, 0.159 mol) in 150 mL of dry Et$_2$O at 0° C. was added dropwise a solution of 3-methyl pent-4-enoic acid (17.4 g, 0.122 mol) in 100 mL of dry Et$_2$O. After addition was complete, the reaction was allowed to warm to room temperature and stirred for 2 h. The reaction mass was poured into a 1 L beaker. Water (6.03 mL) and 15% NaOH (6.03 mL) were carefully added with good stirring over a 30 min period. The white solid separated were removed by filtration and washed well with Et$_2$O. The combined filtrates were dried and concentrated by distillation at atmospheric pressure. The residue was distilled to get desired compound 9.04 g (74%); $^1$H NMR (CDCl$_3$) δ ppm 5.65 (m, 1H), 4.90 (m, 2H), 3.55 (m, 2H), 3.30 (m, 1H), 2.25 (m, 1H), 1.50 (q, J=7 Hz, 2H), 1.00 (d, J=7 Hz, 3H).

Step 4: Preparation of 5-bromo-3-methylpent-1-ene

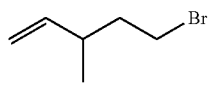

To a stirred solution of 4.504 g (44.97 mmol) of the 3-methyl pent-4-ene-1-ol in 100 mL of dichloromethane at 0° C. were added 3.8 mL (49.1 mmol) of methanesulfonyl chloride and 6.91 mL (49.6 mmol) of triethylamine sequentially, and the resulting mixture stirred at 0° C. for 15 min. The reaction mixture was then poured into 100 mL of saturated aqueous NaHCO$_3$, and the resulting mixture stirred vigorously for 10 min. The organic phase was separated, dried (Na$_2$SO$_4$), and then concentrated under reduced pressure to get crude Mesylate compound. The crude compound was dissolved in 130 mL of dry THF and to the solution was added 5.87 g (67.6 mmol) of anhydrous lithium bromide. The resulting mixture was refluxed for 4 h. The reaction mass was cooled to room temperature and diluted with 300 mL of pentane. The organic phase washed with two 100-mL portions of saturated NaHCO$_3$, and five 100-mL portions of water and then dried (Na$_2$SO$_4$). Solvent was removed by distillation through a 30-cm Vigreux column at atmospheric pressure. Evaporative distillation of the residue (70 deg C., 80 mmHg) gave 6.28 g (86%) of the bromide. $^1$H NMR (CDCl$_3$) δ ppm 1.01 (d, J=5 Hz, 3H,), 1.80 (dt, J=J'=5 Hz, 2H,), 2.35 (m, J=5 Hz, 1H), 3.36 (t, J=5 Hz, 2H), 5.02 (m, 2H), 5.64 (m, 1H).

Step 5: Preparation of (2R)-6-methyloct-7-en-2-ol

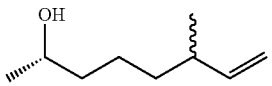

Magnesium turnings (1.3 g, 55.2 mmol) were suspended in dry THF (50 mL) and to the mixture was added a pinch of iodine (20 mg) at room temperature. To this reaction mass was added a solution of 5-bromo-3-methylpent-1-ene (6 g, 36.8 mmol) in THF (200 mL). The reaction mass was heated with hot air gun to initiate the reaction. When the reaction was judged complete, the solution was cannulated to a solution of (S)-propylene oxide (3.21 g, 55.2 mmol) and copper bromide (0.528 g, 3.68 mmol) in THF (50 mL) at −78° C. The reaction mass was allowed to come to room temperature and stirred overnight. The reaction mass was quenched with saturated ammonium chloride solution and extracted with diethyl ether (200 mL×3). The combined organic layer was dried over anhydrous Na$_2$SO$_4$ and concentrated at room temperature to get crude compound. The crude compound was purified by column chromatography (Silica gel, 10% TBME in pet ether) to get (2R)-6-methyloct-7-en-2-ol (12.4 g, 92%) as oily liquid. $^1$H NMR (400 MHz, CDCl$_3$): δ ppm 5.82-5.69 (m, 1H), 4.98-4.91 (m, 2H), 4.27-4.26 (m, 1H), 3.65-3.39 (m, 1H), 2.15-1.98 (m, 1H), 1.36-1.19 (m, 5H), 1.18-1.1 (m, 1H), 1.08-0.95 (m, 5H), 0.89-0.78 (m, 1H).

Step 6: Preparation of (2R)-6-methyloct-7-en-2-yl 4-methylbenzenesulfonate

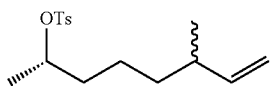 [SMILES: C=CC(C)CCC[C@H](C)OS(=O)(=O)c1ccc(C)cc1]

To a solution of (2R)-6-methyloct-7-en-2-ol (12 g, 84 mmol) in pyridine (16 mL) was added DMAP (0.51 g, 4.22 mmol) and the solution was stirred for 10 min. P-Toluenesulfonyl chloride (18.5 g, 97 mmol) was added to the reaction mass at 0° C. The reaction mass was allowed to come to room temperature and stirred overnight. Pyridine was removed under reduced pressure and the residue was diluted with ethyl acetate (200 mL). The organic solution was washed with aqueous 1.5 N HCl solution, saturated bicarbonate solution, brine solution, dried over anhydrous Na$_2$SO$_4$ and concentrated under reduced pressure to get crude compound (14.5 g, 32%). The crude compound was taken to the next step without further purification.

Step 7: Preparation of (3R)-ethyl 2-(diphenylmethyleneamino)-3,7 dimethylnon-8-enoate

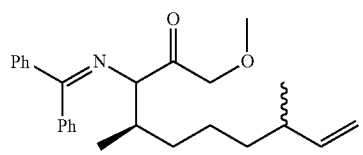 [SMILES: C=CC(C)CCC[C@@H](C)C(N=C(c1ccccc1)c1ccccc1)C(=O)COC]

To a solution of 2R)-6-methyloct-7-en-2-yl 4-methylbenzenesulfonate (15 g, 50.6 mmol) and N-(diphenylmethylene)glycinate ethyl ester (13.53 g, 50.6 mmol) in toluene (120 mL) was added LiHMDS (60.7 mL, 60.7 mmol, 1M solution in THF) at 0° C. The reaction mass was allowed to come to room temperature heated at 110° C. for 2 h. The reaction mass was cooled to room temperature, quenched with water and extracted with ethyl acetate (200 mL×3). The combined organic layer was dried over anhydrous Na$_2$SO$_4$ and concentrated under reduced pressure to get crude compound (14.5 g). The crude compound was taken to the next step without further purification. MS: MS m/z 392.1 (M$^+$+1).

Step 8: Preparation of (3R)-ethyl 2-amino-3,7-dimethylnon-8-enoate

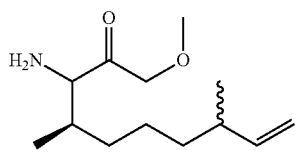 [SMILES: C=CC(C)CCC[C@@H](C)C(N)C(=O)COC]

To a solution of (3R)-ethyl 2-(diphenylmethyleneamino)-3,7 dimethylnon-8-enoate (14.5 g, 37 mmol) in diethyl ether (25 mL) was added aqueous 1.5 N HCl solution (125 mL) and the reaction mass was stirred at room temperature overnight. The reaction mass was washed with diethyl ether (100 mL). The aqueous solution was basified using saturated sodium bicarbonate solution and extracted with ethyl acetate (100 mL×3). The combined organic layer was dried over anhydrous Na$_2$SO$_4$ and concentrated under reduced pressure to get crude compound (2.1 g, 23%). The crude compound was taken to the next step without further purification. $^1$H NMR (400 MHz, CDCl$_3$): δ ppm 5.85-5.60 (m, 1H), 4.98-4.85 (dd, J=1.6, 2.8 Hz, 2H), 4.10-4.06 (m, 2H), 3.15-3.14 (m, 1H), 2.15-2.02 (m, 1H), 1.94-1.75 (m, 3H), 1.32-1.17 (m, 9H), 0.95-0.93 (m, 3H), 0.84-0.74 (m, 3H). MS: MS m/z 227.7 (M$^+$+1).

Step 9: Preparation of (3R)-ethyl 2-(tert-butoxycarbonylamino)-3,7-dimethylnon-8-enoate

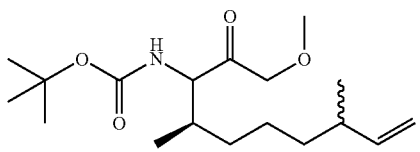 [SMILES: C=CC(C)CCC[C@@H](C)C(NC(=O)OC(C)(C)C)C(=O)COC]

A solution of (3R)-ethyl 2-amino-3,7-dimethylnon-8-enoate (2.0 g, 8.8 mmol) in DCM (20 mL) was added DIPEA (1.7 g, 13.2 mmol) followed by (Boc)$_2$O (2.4 g, 11.4 mmol) at room temperature. The reaction mass was stirred at room temperature overnight. The reaction mass was diluted with DCM and washed with water. The organic layer was dried over anhydrous Na$_2$SO$_4$ and concentrated under reduced pressure to get crude compound. The crude compound was purified by column chromotography (Silica gel, 20% ethyl acetate in pet-ether) to get 2.7 g, (84%) of (3R)-ethyl 2-(tert-butoxycarbonylamino)-3,7-dimethylnon-8-enoate as oily liquid. $^1$H NMR (400 MHz, CDCl$_3$): δ ppm 5.85-5.60 (m, 1H), 4.98-4.85 (dd, J=1.6, 2.8 Hz, 2H), 4.10-4.06 (m, 2H), 2.15-2.02 (m, 1H), 1.55-1.44 (m, 8H), 1.39-1.30 (s, 9H), 1.27-1.21 (m, 4H), 0.95-0.93 (m, 3H), 0.84-0.74 (m, 3H).

Step 10: Preparation of (3R)-2-(tert-butoxycarbonylamino)-3,7-dimethylnon-8-enoic acid

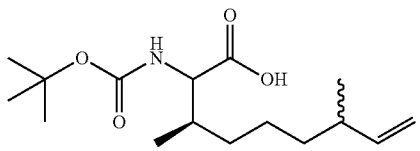 [SMILES: C=CC(C)CCC[C@@H](C)C(NC(=O)OC(C)(C)C)C(=O)O]

To a solution of (3R)-ethyl 2-(tert-butoxycarbonylamino)-3,7-dimethylnon-8-enoate (2.7 g, 8.25 mmol) in THF/water (40 mL, 1:1) was added methanol (20 mL) followed by LiOH (0.987 g, 41.2 mmole) at room temperature. The reaction mass was stirred at room temperature overnight. Solvent was evaporated under reduced pressure and the residue was diluted with water (100 mL). The aqueous solution was acidified with aqueous 1.5 N HCl solutions to pH~3 and extracted with ethyl acetate (100 mL×3). The combined organic layer was dried over anhydrous Na₂SO₄ and concentrated under reduce pressure to get crude compound. The crude compound was purified by column chromotography (Silica gel, 3% methanol in DCM) to get 2.1 g (85%) of desired compound as gummy liquid. ¹H NMR (400 MHz, DMSO-D₆): δ ppm 12.2-12.02 (bs, 1H), 6.92-6.85 (m, 1H) 5.72-5.66 (m, 1H), 4.98-4.85 (dd, J=1.6, 2.8 Hz, 2H), 4.03-3.95 (m, 1H), 2.58-2.56 (m, 1H) 2.15-2.02 (m, 1H), 1.45-1.36 (m, 10H), 1.27-1.21 (m, 5H), 0.95-0.93 (m, 3H), 0.84-0.74 (m, 3H).
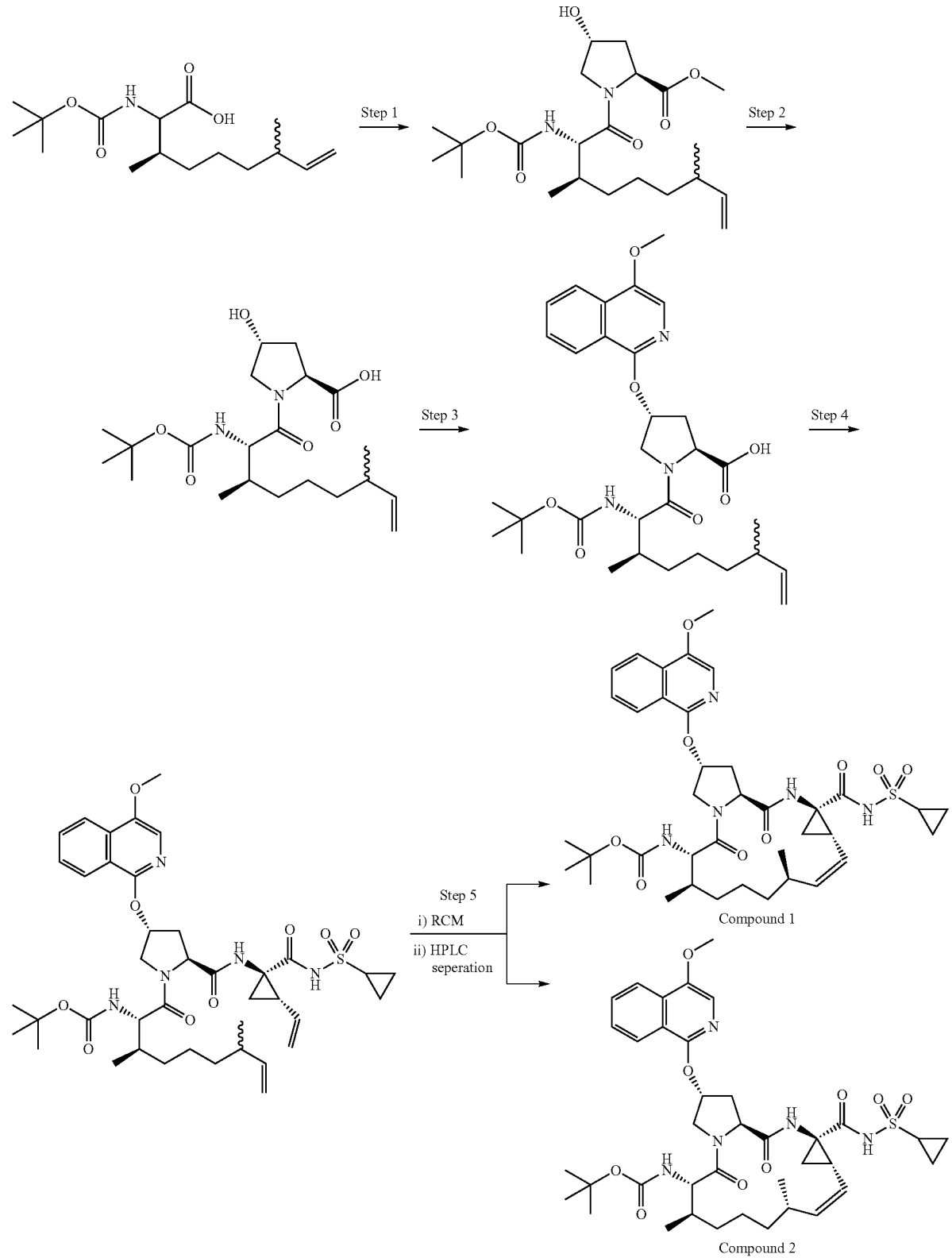

Step 1: Preparation of (2S,4R)-methyl 1-((2S,3R)-2-(tert-butoxycarbonylamino)-3,7-dimethylnon-8-enoyl)-4-hydroxypyrrolidine-2-carboxylate

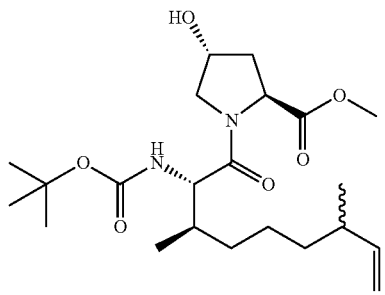 [SMILES: C=CC(C)CCC[C@@H](C)[C@H](NC(=O)OC(C)(C)C)C(=O)N1C[C@H](O)C[C@H]1C(=O)OC]

To a slurry of (3R)-2-((tert-butoxycarbonyl)amino)-3,7-dimethylnon-8-enoic acid (6.5 g, 21.7 mmol), L-4-hydroxyproline methyl ester hydrochloride (3.9 g, 21.7 mmol) and O-(7-Azabenzotriazol-1-yl)-N,N,N',N'-tetramethyluronium hexafluorophosphate (8.36 g, 21.7 mmol) in DCM (50 mL) at 0° C., N,N-diisopropylethylamine (11.5 mL, 66.6 mmol) was added dropwise. The resulting light yellow mixture was stirred at rt overnight, washed with 1M HCl (35 ml) and brine, dried over $Na_2SO_4$, filtered, concentrated in vacuo. The residual oil (12 g) was purified by conventional column chromatography (60-120 g silica gel column), eluted with 4%~8% IPA-Hexane to afford the desired product (2S,4R)-methyl 1-((2S,3R)-2-(tert-butoxycarbonylamino)-3,7-dimethylnon-8-enoyl)-4-hydroxypyrrolidine-2-carboxylate (9a, 4.3 g, 46% yield) as a white foam and the undesired diastereomer (2S,4R)-methyl 1-((2R,3R)-2-(tert-butoxycarbonylamino)-3,7-dimethylnon-8-enoyl)-4-hydroxypyrrolidine-2-carboxylate (9b, 1.9 g, 20% yield) as a viscous oil. $^1$H NMR (400 MHz, CDCl$_3$): δ ppm 5.73-5.64 (m, 1H), 5.19-5.17 (m, 1H), 4.97-4.88 (m, 2H), 4.70-4.66 (t, J=8.4 Hz, 1H), 4.53 (bs, 1H), 4.29-4.25 (m, 1H), 3.99-3.96 (d, J=10.8 Hz, 3H), 3.72 (s, 3H), 3.70-3.66 (m, 1H), 2.34-2.11 (m, 1H), 2.10-2.00 (m, 2H), 1.85-1.81 (m, 1H), 1.49-1.41 (m, 9H), 1.39-1.14 (m, 3H), 0.98-0.86 (m, 7H) MS: MS m/z 427.2 (M$^+$+1).

Step 2: Preparation of (2S,4R)-1-((2S,3R)-2-(tert-butoxycarbonylamino)-3,7-dimethylnon-8-enoyl)-4-hydroxypyrrolidine-2-carboxylic acid

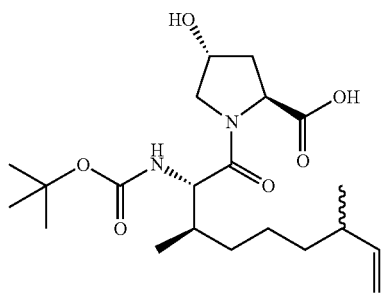 [SMILES: C=CC(C)CCC[C@@H](C)[C@H](NC(=O)OC(C)(C)C)C(=O)N1C[C@H](O)C[C@H]1C(=O)O]

To a solution of (2S,4R)-methyl 1-((2S,3R)-2-(tert-butoxycarbonylamino)-3,7-dimethylnon-8-enoyl)-4-hydroxypyrrolidine-2-carboxylate (4.3 g, 10 mmol) in THF/water (30 mL, 1:1) was added methanol (10 mL) followed by LiOH (1.3 g, 0.030 moles) at room temperature. The reaction mass was stirred at room temperature overnight. Solvent was evaporated under reduced pressure and the residue was diluted with water (100 mL). The aqueous solution was acidified with aqueous 1.5 N HCl solutions to pH~3 and extracted with ethyl acetate (100 mL×3). The combined organic layer was dried over anhydrous $Na_2SO_4$ and concentrated under reduce pressure to get the desired product (2S,4R)-((2S,3R)-2-(tert-butoxycarbonylamino)-3,7-dimethylnon-8-enoyl)-4-hydroxypyrrolidine-2-carboxylic acid (3.2 g, 78% yield) as a white solid. $^1$H NMR (400 MHz, CDCl$_3$): δ ppm 5.70-5.61 (m, 1H), 5.14-5.12 (d, J=8.8 Hz, 1H), 4.96-4.88 (m, 2H), 4.82-4.78 (t, J=8.4 Hz, 1H), 4.52 (bs, 1H), 4.27-4.23 (m, 1H), 3.57-3.53 (m, 3H), 2.48-2.42 (m, 1H), 2.33-2.28 (m, 1H), 1.88-1.82 (m, 2H), 1.45-1.42 (s, 9H), 1.29-1.21 (m, 3H), 0.98-0.93 (m, 7H) MS: MS m/z 411.2 (M$^+$+1).

Step 3: Preparation of (2S,4R)-1-((2S,3R)-2-(tert-butoxycarbonylamino)-3,7-dimethylnon-8-enoyl)-4-(4-methoxyisoquinolin-1-yloxy)pyrrolidine-2-carboxylic acid

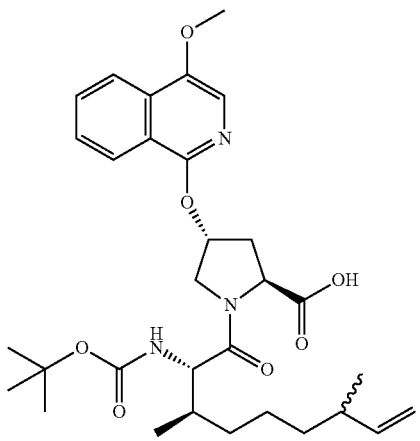 [SMILES: C=CC(C)CCC[C@@H](C)[C@H](NC(=O)OC(C)(C)C)C(=O)N1C[C@H](Oc2ncc(OC)c3ccccc23)C[C@H]1C(=O)O]

To a solution of (2S,4R)-1-((3R)-2-((tert-butoxycarbonyl)amino)-3,7-dimethylnon-8-enoyl)-4-hydroxypyrrolidine-2-carboxylic acid (1.5 g, 3.6 mmol) in DMSO was added 1-chloro-4-methoxyisoquinoline (840 mg, 4.4 mmol) followed by t-BuOK (1M sol. in THF, 18 mL) at room temperature under nitrogen atmosphere. The reaction mass was stirred at room temperature for 4 h. The reaction mass was quenched with aqueous citric acid solution and extracted with ethyl acetate. The combined organic layer was dried over anhydrous $Na_2SO_4$ and concentrated under reduced pressure to get crude compound. The crude compound was purified by combiflash to get desired product (800 mg, 40%) as off-white solid. $^1$H NMR (400 MHz, CDCl$_3$): δ ppm 8.11-8.09 (m, 2H), 7.70-7.66 (t, J=7.4 Hz, 1H), 7.56-7.51 (t, J=8.0 Hz, 1H), 7.47 (s, 1H), 5.78 (bs, 1H), 5.69-5.65 (m, 1H), 5.14-5.11 (m, 1H), 4.96-4.88 (m, 3H), 4.43-4.41 (m, 1H), 4.27-4.24 (m, 1H), 3.99 (s, 4H), 2.75-2.73 (m, 1H), 2.67-2.65 (m, 1H), 2.10 (bs, 1H), 1.88-1.85 (m, 2H), 1.31 (s, 9H), 1.24 (s, 2H), 0.98-0.96 (m, 4H), 0.91-0.86 (m, 4H) MS: MS m/z 568.2 (M$^+$+1).

Step 4: Preparation of tert-butyl (2S,3R)-1-(2S,4R)-2-((1R,2S)-1-(cyclopropylsulfonylcarbamoyl)-2-vinylcyclopropylcarbamoyl)-4-(4-methoxyisoquinolin-1-yloxy)pyrrolidin-1-yl)-3,7-dimethyl-1-oxonon-8-en-2-ylcarbamate

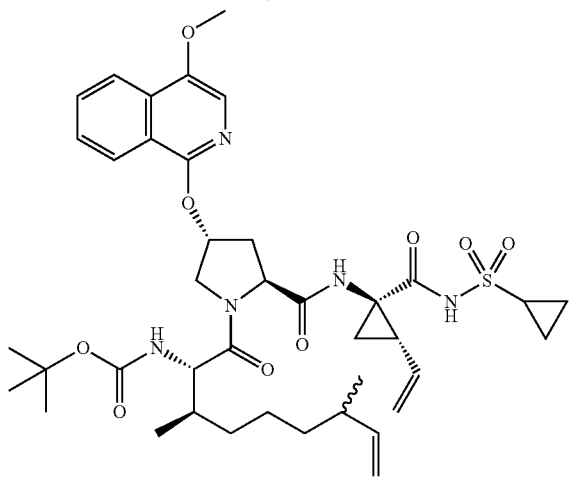 [SMILES: C=CC(C)CCC[C@@H](C)[C@H](NC(=O)OC(C)(C)C)C(=O)N1C[C@H](Oc2ncc(OC)c3ccccc23)C[C@H]1C(=O)N[C@]1(C(=O)NS(=O)(=O)C2CC2)C[C@H]1C=C]

To a solution of (2S,4R)-1-((3R)-2-((tert-butoxycarbonyl)amino)-3,7-dimethylnon-8-enoyl)-4-((4-methoxyisoquinolin-1-yl)oxy)pyrrolidine-2-carboxylic acid (800 mg, 1.4 mmole) in dichloromethane (30 mL) was added DIPEA (0.73 mL, 4.2 mmol), HATU (530 mg, 1.4 mmole) followed by (1R,2S)-1-amino-N-(cyclopropylsulfonyl)-2-vinylcyclopropanecarboxamide hydrochloride (prepared according to the procedure described in WO 03/099274, Page No. 53-59, 74-76) (600 mg, 1.5 mmole) at room temperature. The reaction mixture was stirred at room temperature for 2 h. The reaction mass was diluted with DCM and washed with water. The organic layer was dried over anhydrous $Na_2SO_4$ and concentrated under reduced pressure to get crude compound. The crude compound was purified by combiflash to get desired product (900 mg, 90%) as off-white solid. $^1$H NMR (400 MHz, $CDCl_3$): δ ppm 8.13-8.07 (m, 2H), 7.72-7.67 (t, J=7.2 Hz, 1H), 7.57-7.53 (t, J=7.2 Hz, 1H), 7.47 (s, 1H), 6.80 (bs, 1H), 5.84-5.79 (m, 2H), 5.73-5.64 (m, 1H), 5.39-5.38 (m, 1H), 5.28-5.23 (d, J=17.2 Hz, 1H), 5.15-5.12 (d, J=10.4 Hz, 1H) 4.97-4.88 (m, 2H), 4.49-4.45 (m, 2H), 4.19-4.17 (m, 2H), 4.00 (s, 3H), 2.90-2.81 (m, 1H), 2.54-2.48 (m, 1H), 2.23-2.07 (m, 2H), 2.05-1.99 (m, 2H), 1.49-1.42 (m, 1H), 1.33 (s, 12H), 1.22-1.15 (m, 2H), 1.07-1.02 (m, 2H), 0.98-0.96 (d, J=6.8 Hz, 4H), 0.86-0.81 (d, J=6.8 Hz, 4H), MS: MS m/z 782.2 ($M^+$+1).

Step 5: Preparation of Compound 1 and Compound 2

Compound 1

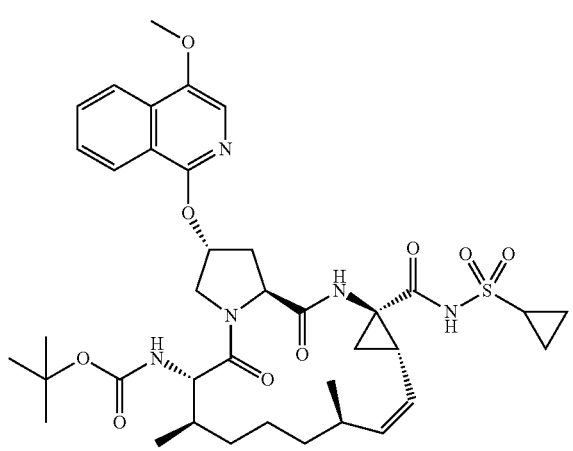

Compound 2

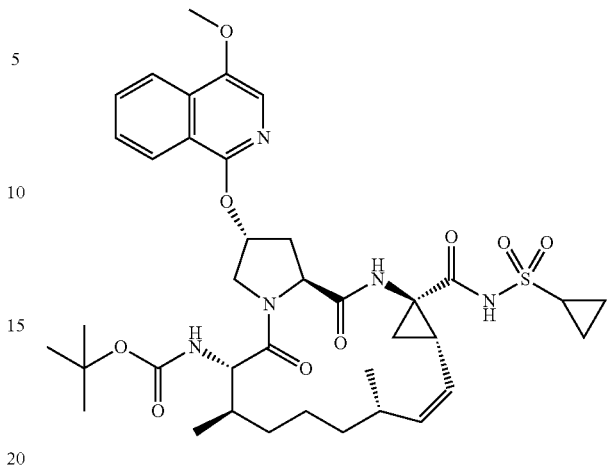

To a degassed solution of tert-butyl (2S,3R)-1-((2S,4R)-2-((1R,2S)-1-(cyclopropylsulfonylcarbamoyl)-2-vinylcyclopropylcarbamoyl)-4-(4-methoxyisoquinolin-1-yloxy)pyrrolidin-1-yl)-3,7-dimethyl-1-oxonon-8-en-2-ylcarbamate (900 mg, 0.3 mmole) in dichloroethane (100 mL) was added Grubbs II generation catalyst (24 mg, 10% w/w) at room temperature under nitrogen atmosphere. The reaction mass was heated at 95° C. overnight. The solvent was evaporated under reduced pressure and the residue was purified by combi-flash to get the (500 mg, 58%) of desired product as a diastereomeric mixture. The diastereomer mixture was separated using Prep-HPLC to get compound 1 (12 mg, 8%) and compound 2 (8 mg, 3%).

Compound 1: tert-butyl (2R,6S,7R,11R,13aS,14aR,16aS,Z)-14a-(cyclopropylsulfonylcarbamoyl)-2-(4-methoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, $CD_3OD$): δ ppm $^1$H NMR (400 MHz, $CD_3OD$): δ ppm 8.17-8.15 (d, J=8.4 Hz, 1H), 8.13-8.11 (d, J=8.4 Hz, 1H), 7.75-7.71 (t, J=8.0 Hz, 1H), 7.58-7.54 (m, 2H), 7.30-7.28 (d, J=7.6 Hz, 1H), 5.83 (bs, 1H), 5.37-5.32 (t, J=11.2 Hz, 1H), 5.05-5.01 (m, 1H), 4.77-4.74 (d, J=11.2 Hz, 1H), 4.67-4.63 (m, 1H), 4.04-4.02 (m, 1H), 3.96 (s, 3H), 3.87-3.83 (m, 1H), 2.97-2.96 (m, 1H), 2.76-2.65 (m, 3H), 2.45-2.38 (m, 1H), 1.82-1.81 (m, 1H), 1.78-1.72 (m, 1H), 1.64-1.61 (m, 3H), 1.45-1.32 (m, 5H), 1.13-1.11 (m, 13H), 0.99-0.98 (d, J=6.4 Hz 3H), 0.95-0.93 (d, J=6.4 Hz, 3H), MS: MS m/z 754.4 ($M^+$+1).

Compound 2: tert-butyl (2R,6S,7R,11S,13aS,14aR,16aS,Z)-14a-(cyclopropylsulfonylcarbamoyl)-2-(4-methoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, $CD_3OD$): δ ppm 8.17-8.15 (d, J=8.0 Hz, 1H), 8.13-8.10 (d, J=8.4 Hz, 1H), 7.75-7.71 (dt, J=6.8 & 1.2 Hz, 1H), 7.58-7.54 (m, 2H), 5.83 (m, 1H), 5.38-5.33 (t, J=10.4 Hz, 1H), 5.06-5.04 (m, 1H), 4.74-4.71 (d, J=11.2 Hz, 1H), 4.69-4.64 (m, 1H), 4.03-4.01 (m, 1H), 3.96 (s, 3H), 3.89-3.84 (t, J=9.6 Hz, 1H), 3.28-3.18 (m, 1H), 2.96-2.88 (m, 1H), 2.72-2.57 (m, 2H), 2.35-2.32 (m, 1H), 1.98-1.95 (m, 1H), 1.75-1.69 (m, 2H), 1.64-1.61 (m, 3H), 1.40-1.38 (m, 1H), 1.30-1.26 (m, 3H), 1.19-1.12 (m, 3H), 1.07 (s, 9H), 0.99-0.91 (m, 6H), MS: MS m/z 752.4 ($M^+$−1).

Preparation of Compound 3 and Compound 4

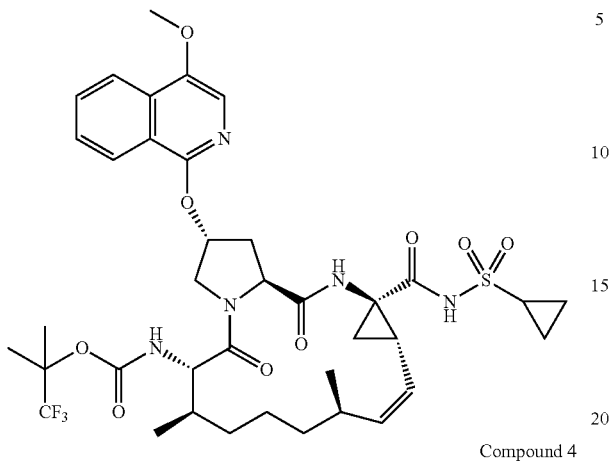

Compound 3

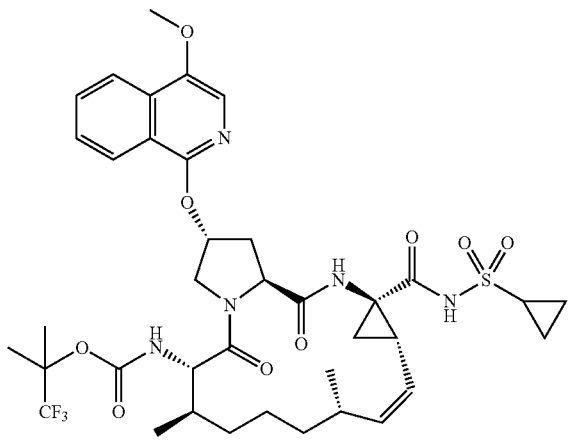

Compound 4

Preparation of (2R,6S,7R,13aS,14aR,16aS,Z)-6-amino-N-(cyclopropylsulfonyl)-2-(4-methoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride

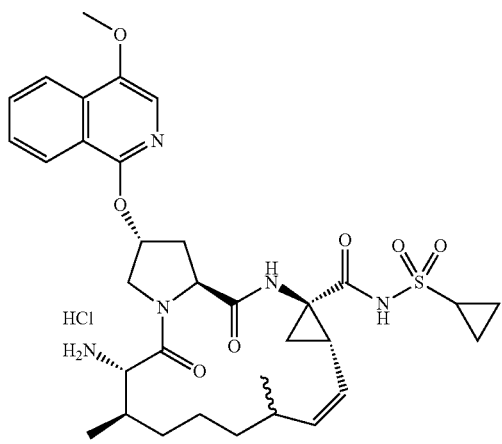 [SMILES: COc1cnc(O[C@@H]2C[C@H]3C(=O)N[C@]4(C(=O)NS(=O)(=O)C5CC5)C[C@H]4/C=C\C(C)CCC[C@@H](C)[C@H](N)C(=O)N3C2)c2ccccc12 ; Cl]

A solution of tert-butyl (2R,6S,7R,13aS,14aR,16aS,Z)-14a-(cyclopropylsulfonylcarbamoyl)-2-(4-methoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (500 mg, 0.66 mmole) in dioxane.HCl was stirred at room temperature for 30 min. The solvent was evaporated under reduced pressure to get crude compound (350 mg, 77%). The crude compound was washed with diethyl ether and taken to the next step without further purification. MS: MS m/z 652.2 ($M^+$−1).

Preparation of pyridin-2-yl 1,1,1-trifluoro-2-methylpropan-2-yl carbonate

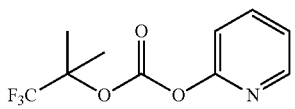

To a slurry of NaH (1.03 g, 25.8 mmol) in THF (70 mL) was added 1,1,1-trifluoro-2-methylpropan-2-ol (3 g, 23.42 mmol). The reaction was stirred at 0° C. for 20 min. A solution of dipyridin-2-yl carbonate (5.06 g, 23.42 mmol) in THF (30 mL) was then added to the mixture. The resulting solution was stirred at room temperature for overnight. Filtered the resulting solid byproducts and washed with EtOAc (2×20 mL). The combined organic layers was washed with water, dried over anhydrous $Na_2SO_4$, filtered and concentrated under reduced pressure. The resulting white pyridin-2-yl (1,1,1-trifluoro-2-methylpropan-2-yl) carbonate (1.24 g, 21%) was directly used as a reagent.

Preparation of Compounds 3 and Compound 4

To a solution of (2R,6S,7R,13aS,14aR,16aS,Z)-6-amino-N-(cyclopropylsulfonyl)-2-(4-methoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride (350 mg, 0.53 mmol) in DCM (4 mL) was added DIPEA (0.3 mL, 1.8 mmole) followed by carbonic acid pyridin-2-yl ester 2,2,2-trifluoro-1,1-dimethyl-ethyl ester (180 mg, 0.72 mmole) at room temperature. The reaction mixture was stirred at room temperature for 30 min. The reaction mass was diluted with DCM and washed with water. The organic layer was dried over anhydrous $Na_2SO_4$ and evaporated under reduced pressure to get crude compound as diastereomer mixture. The diastereomer mixture was separated using prep-HPLC to get compound 3 (50 mg, 12%) and Compound 4 (30 mg, 7%) as white solid.

Compound 3: 1,1,1-trifluoro-2-methylpropan-2-yl (2R,6S,7R,11R,13aS,14aR,16aS,Z)-14a-(cyclopropylsulfonylcarbamoyl)-2-(4-methoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate $^1$H NMR (400 MHz, $CD_3OD$): δ ppm 8.17-8.15 (d, J=8.4 Hz, 1H), 8.13-8.11 (d, J=8.4 Hz, 1H), 7.75-7.71 (t, J=8.0 Hz, 1H), 7.58-7.54 (m, 2H), 7.30-7.28 (d, J=7.6 Hz, 1H), 5.82 (m, 1H), 5.38-5.32 (t, J=10.4 Hz, 1H), 5.04-4.98 (m, 1H), 4.79-4.77 (d, J=10.8 Hz, 1H), 4.79-4.77 (m, 1H), 4.02 (s, 3H), 4.00-3.99 (m, 1H), 3.85-3.79 (m, 1H), 3.98-2.94 (m, 1H), 2.77-2.66 (m, 3H), 2.42-2.38 (m, 1H), 1.88-1.82 (m, 1H), 1.74-1.71 (m, 1H), 1.64-1.57 (m, 3H), 1.44-1.40 (m, 1H), 1.36-1.31 (m, 6H), 1.17-1.11 (m, 4H), 0.99-0.93 (m, 9H), $^{19}$F NMR: δ ppm −85.12 (3 F); MS: MS m/z 808.1 (M$^+$+1).
Compound 4: 1,1,1-trifluoro-2-methylpropan-2-yl (2R,6S,7R,11S,13aS,14aR,16aS,Z)-14a-(cyclopropylsulfonylcarbamoyl)-2-(4-methoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. MS: MS m/z 808.3 (M$^+$+1).
Preparation of Compound 5 and Compound 6
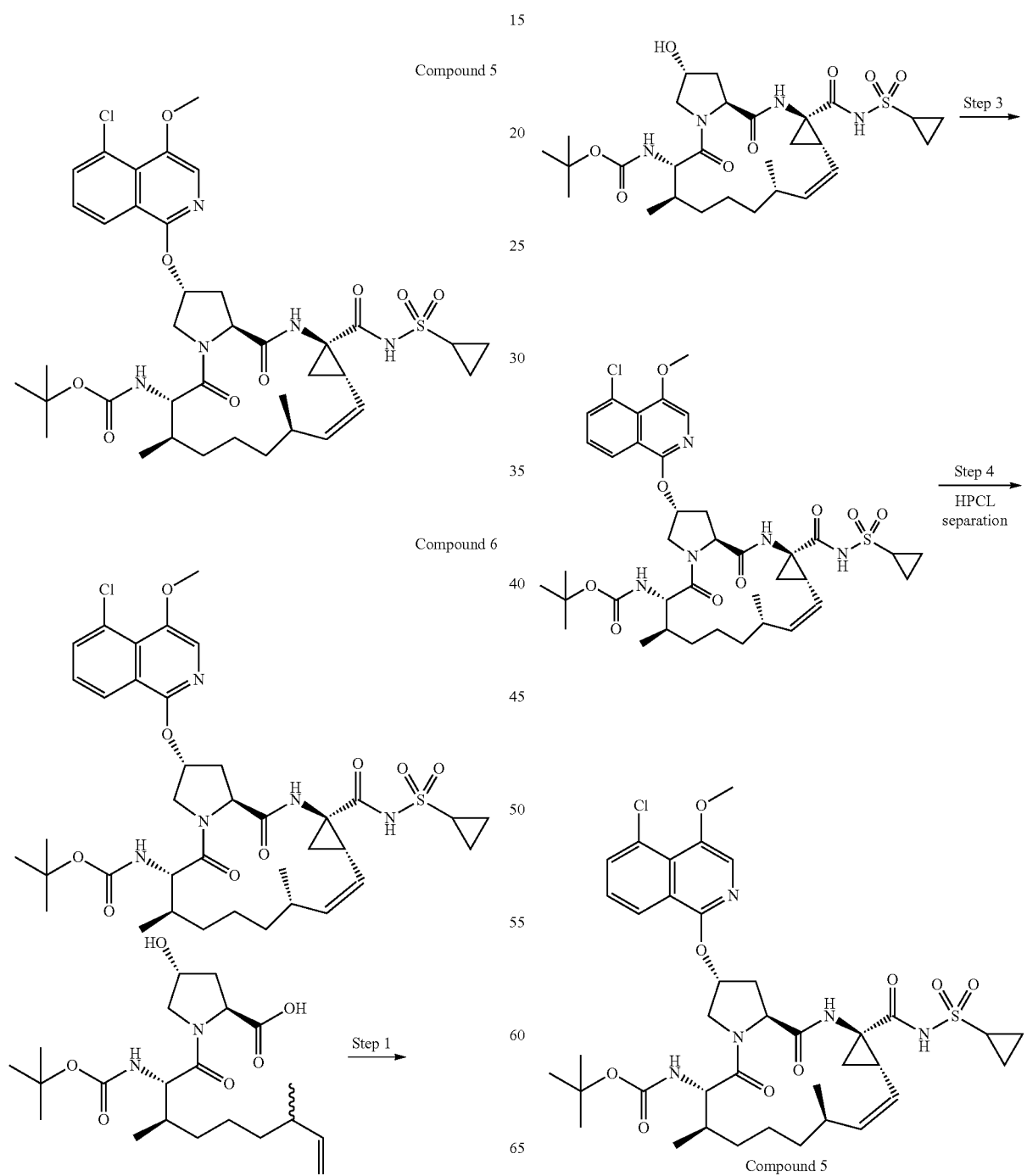

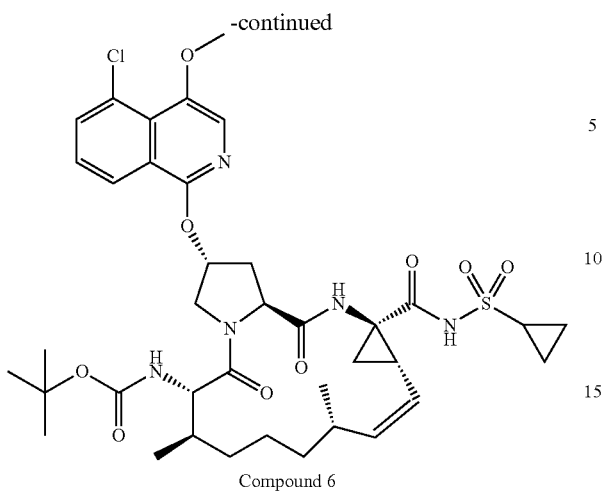

Compound 6

Step 1: Preparation of tert-butyl (2S,3R)-1-(2S,4R)-2-((1R,2S)-1-cyclopropylsulfonylcarbamoyl)-2-vinylcyclopropylcarbamoyl)-4-hydroxypyrrolidin-1-yl)-3,7-dimethyl-1-oxonon-8-en-2-ylcarbamate

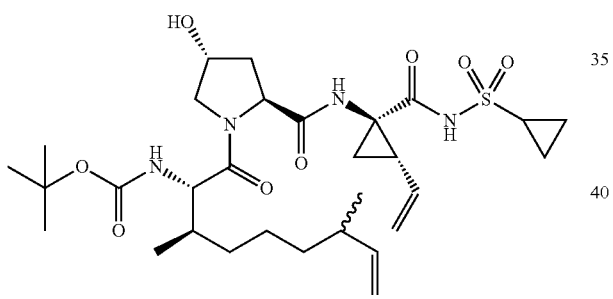

To a solution of (2S,4R)-1-((2S,3R)-2-((tert-butoxycarbonyl)amino)-3,7-dimethylnon-8-enoyl)-4-hydroxypyrrolidine-2-carboxylic acid (2 g, 4.9 mmol) in dichloromethane (15 mL) was added HATU (1.86 g, 4.9 mmol) followed by DIPEA (4.2 mL, 24.5 mmole) at room temperature. The reaction mass was stirred at the same temperature for 10 min. (1R,2S)-1-amino-N-(cyclopropylsulfonyl)-2-vinylcyclopropanecarboxamide hydrochloride (prepared according to the procedure described in WO 03/099274, Page No. 53-59, 74-76) (2 g, 5.3 mmole) was added to the reaction mass and was stirred at room temperature for 3 hrs. The reaction mass was diluted with dichloromethane and washed with water. The organic layer was dried over anhydrous $Na_2SO_4$ and concentrated under reduced pressure to get the crude compound. The crude compound was purified by Combiflash (3% MeOH in CHCl$_3$) to get 1.9 g (62%) of desired product as white solid. MS: MS m/z 623.5 (M$^+$-1).

Step 2: Preparation of tert-butyl tert-butyl (2R,6S,7R,13aS,14aR,16aS,Z)-14a-(cyclopropylsulfonylcarbamoyl)-2-hydroxy-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

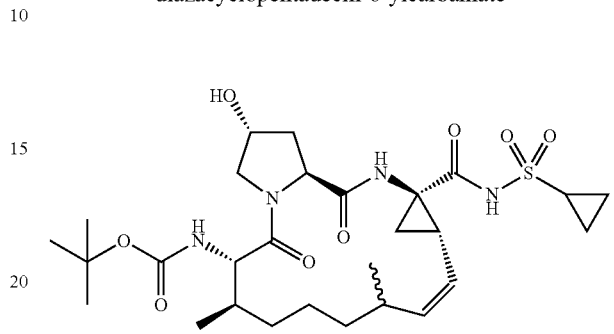

To a degassed solution of tert-butyl (2S,3R)-1-(2S,4R)-((1R,2S)-1-cyclopropylsulfonylcarbamoyl)-2-vinylcyclopropylcarbamoyl)-4-hydroxypyrrolidin-1-yl)-3,7-dimethyl-1-oxonon-8-en-2-ylcarbamate (0.9 g, 1.4 mmol) in dichloroethane (150 mL) was added Grubbs II generation catalyst (90 mg, 10% w/w) at room temperature under nitrogen atmosphere. The reaction mass was heated at 95° C. overnight. The solvent was evaporated under reduced pressure and the residue was purified by ISCO to get desired compound (600 mg, 69%). MS: MS m/z 595.2 (M$^+$-1).

Step 3: Preparation of tert-butyl (2R,6S,7R,13aS,14aR,16aS,Z)-2-(5-chloro-4-methoxyisoquinolin-1-yloxy)-14a-(cyclopropylsulfonylcarbamoyl)-7,11-dimethyl-5,16-dioxo-1,2,3,5,6,7,8,9,10,11,13a,14,14a,15,16,16a-hexadecahydrocyclopropa[e]pyrrolo[1,2-A][1,4]diazacyclopentadecin-6-ylcarbamate

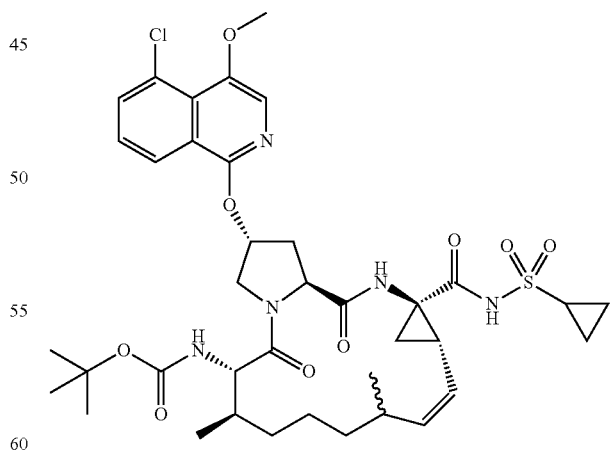

To a solution of tert-butyl ((2R,6S,7R,13aS,14aR,16aS,Z)-14a-((cyclopropylsulfonyl)carbamoyl)-2-hydroxy-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate (500 mg, 0.8 mmol) and 1,5-dichloro-4-methoxyisoquinoline (230 mg, 1.0 mmol)

in DMSO (5 mL) was added t-BuOK (1 M solution in THF, 450 mg, 4.0 mmol) at room temperature under nitrogen atmosphere. The reaction mixture was stirred at room temperature for 2 h. The reaction mass was quenched with aqueous citric acid solution and extracted with ethyl acetate (150 mL×3). The combined organic layer was washed with water, brine solution, dried over anhydrous $Na_2SO_4$ and concentrated under reduced pressure to get crude compound as diastereomer mixture. MS: MS m/z 789.3 ($M^+$+1).

Step 4: Preparation Compound 5 and Compound 6

Diastereomer mixture of (2R,6S,7R,13aS,14aR,16aS,Z)-2-(5-chloro-4-methoxyisoquinolin-1-yloxy)-14a-(cyclopropylsulfonylcarbamoyl)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate was separated by Prep-HPLC to get desired compound 5 and compound 6.

Compound 5

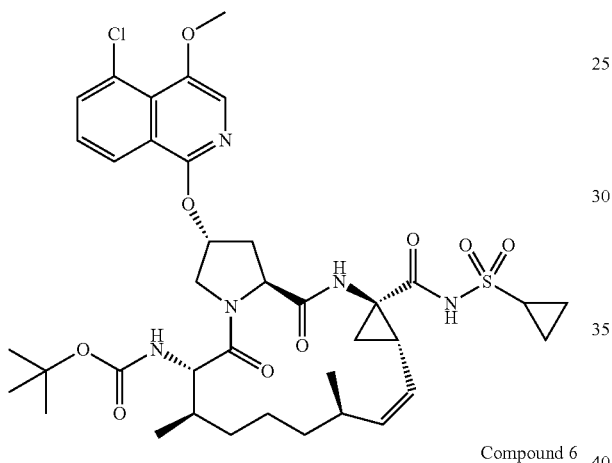

Compound 6

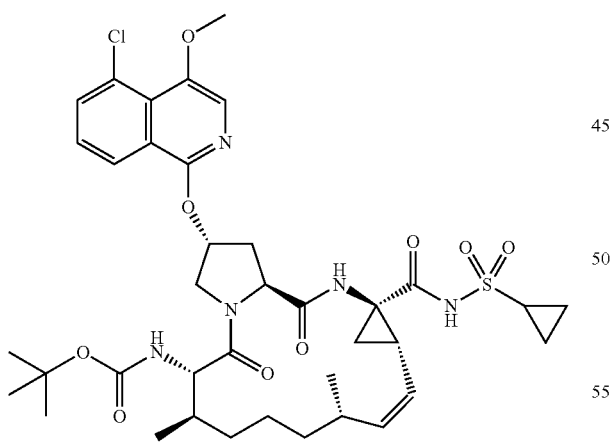

Compound 5: tert-butyl (2R,6S,7R,11R,13aS,14aR,16aS,Z)-2-(5-chloro-4-methoxyisoquinolin-1-yloxy)-14a-(cyclopropylsulfonylcarbamoyl)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (230 mg, 35%). $^1$H NMR (400 MHz, $CD_3OD$): δ ppm 8.18-8.16 (d, J=7.6 Hz, 1H), 7.78-7.76 (d, J=6.8 Hz, 1H), 7.70 (s, 1H), 7.48-7.44 (t, J=8.0 Hz, 1H), 6.67-6.64 (d, J=8.4 Hz, 1H), 5.83 (bs, 1H), 5.37-5.32 (t, J=11.2 Hz, 1H), 5.05-5.01 (m, 1H), 4.77-4.74 (d, J=11.2 Hz, 1H), 4.67-4.63 (m, 1H), 4.04-4.02 (m, 1H), 3.96 (s, 3H), 3.87-3.83 (m, 1H), 2.97-2.96 (m, 1H), 2.76-2.65 (m, 3H), 2.45-2.38 (m, 1H), 1.82-1.81 (m, 1H), 1.78-1.72 (m, 1H), 1.64-1.61 (m, 3H), 1.45-1.32 (m, 5H), 1.13-1.11 (m, 13H), 0.99-0.98 (d, J=6.4 Hz 3H), 0.95-0.93 (d, J=6.4 Hz, 3H), MS: MS m/z 789.2 ($M^+$+1).

Compound 6: tert-butyl (2R,6S,7R,11S,13aS,14aR,16aS,Z)-2-(5-chloro-4-methoxyisoquinolin-1-yloxy)-14a-(cyclopropylsulfonylcarbamoyl)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, $CD_3OD$): δ ppm 8.18-8.16 (d, J=8.4 Hz, 1H), 7.76-7.74 (d, J=7.6 Hz, 1H), 7.70 (s, 1H), 7.48-7.44 (d, J=7.6 Hz, 1H), 6.59-6.57 (d, J=8.4 Hz, 1H) 5.83 (bs, 1H), 5.38-5.33 (t, J=10.4 Hz, 1H), 5.06-5.04 (m, 1H), 4.74-4.71 (d, J=11.2 Hz, 1H), 4.69-4.64 (m, 1H), 4.03-4.01 (m, 1H), 3.96 (s, 3H), 3.89-3.84 (t, J=9.6 Hz, 1H), 3.28-3.18 (m, 1H), 2.96-2.88 (m, 1H), 2.72-2.57 (m, 2H), 2.35-2.32 (m, 1H), 1.98-1.95 (m, 1H), 1.75-1.69 (m, 2H), 1.64-1.61 (m, 3H), 1.40-1.38 (m, 1H), 1.30-1.26 (m, 3H), 1.19-1.12 (m, 3H), 1.07 (s, 9H), 0.99-0.91 (m, 6H), MS: MS m/z 787.8 ($M^+$−1).

Preparation of Compounds 7 and Compound 8

Compound 7

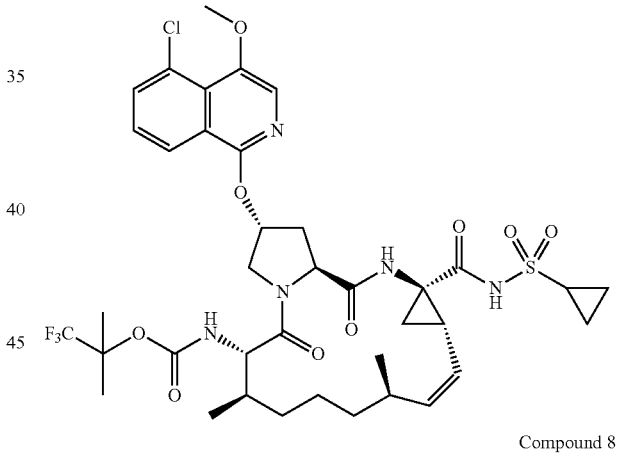

Compound 8

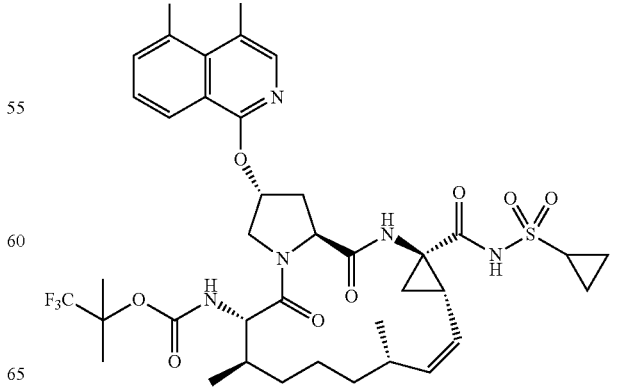

Preparation of (2R,6S,7R,13aS,14aR,16aS,Z)-6-amino-2-(5-chloro-4-methoxyisoquinolin-1-yloxy)-N-(cyclopropylsulfonyl)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride

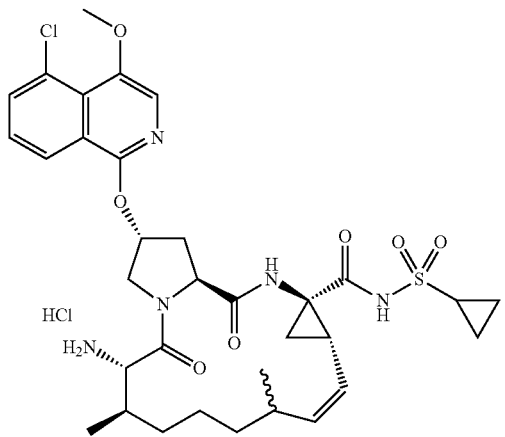 [SMILES: COc1cnc(O[C@@H]2C[C@H]3C(=O)N[C@]4(C(=O)NS(=O)(=O)C5CC5)C[C@H]4/C=C\C(C)CCC[C@@H](C)[C@H](N)C(=O)N3C2)c2cccc(Cl)c12 ; Cl]

A solution of tert-butyl (2R,6S,7R,13aS,14aR,16aS,Z)-2-(5-chloro-4-methoxyisoquinolin-1-yloxy)-14a-(cyclopropylsulfonylcarbamoyl)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (300 mg, 3.3 mmol) in dioxane.HCl was stirred at room temperature for 30 min. The solvent was evaporated under reduced pressure to get crude compound (250 mg, 96%). The crude compound was washed with diethyl ether and taken to the next step without further purification. MS: MS m/z 688.2 (M$^+$−36).

Compound 7 and compound 8 was prepared using the intermediates described herein and by following the general procedure described for the synthesis of Compound 3. Diastereomer mixture was separated by prep-HPLC.

Compound 7: 1,1,1-trifluoro-2-methylpropan-2-yl (2R,6S,7R,11R,13aS,14aR,16aS,Z)-2-(5-chloro-4-methoxyisoquinolin-1-yloxy)-14a-(cyclopropylsulfonylcarbamoyl)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.18-8.15 (d, J=7.6 Hz, 1H), 7.78-7.76 (d, J=6.4 Hz, 1H), 7.70 (s, 1H), 7.49-7.45 (t, J=8.0 Hz, 1H), 5.81 (m, 1H), 5.37-5.35 (t, J=10.8 Hz, 1H), 5.04-4.94 (m, 1H), 4.78-4.75 (d, J=11.2 Hz, 1H), 4.70-4.66 (m, 1H), 4.01-3.97 (m, 1H), 3.96 (s, 3H), 3.80-3.77 (d, J=10.4 Hz, 1H), 2.98-2.94 (m, 1H), 2.77-2.64 (m, 3H), 2.45-2.38 (m, 1H), 1.84-1.82 (m, 1H), 1.74-1.71 (m, 1H), 1.65-1.60 (m, 3H), 1.43-1.29 (m, 8H), 1.17-1.05 (m, 4H), 0.98-0.91 (m, 9H), $^{19}$F NMR: δ ppm −85.11 (3 F); MS: MS m/z 843.1 (M$^+$+1).

Compound 8: 1,1,1-trifluoro-2-methylpropan-2-yl (2R,6S,7R,11S,13aS,14aR,16aS,Z)-2-(5-chloro-4-methoxyisoquinolin-1-yloxy)-14a-(cyclopropylsulfonylcarbamoyl)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. MS: MS m/z 843.3 (M$^+$+1).

Preparation of Compounds 9 and Compound 10

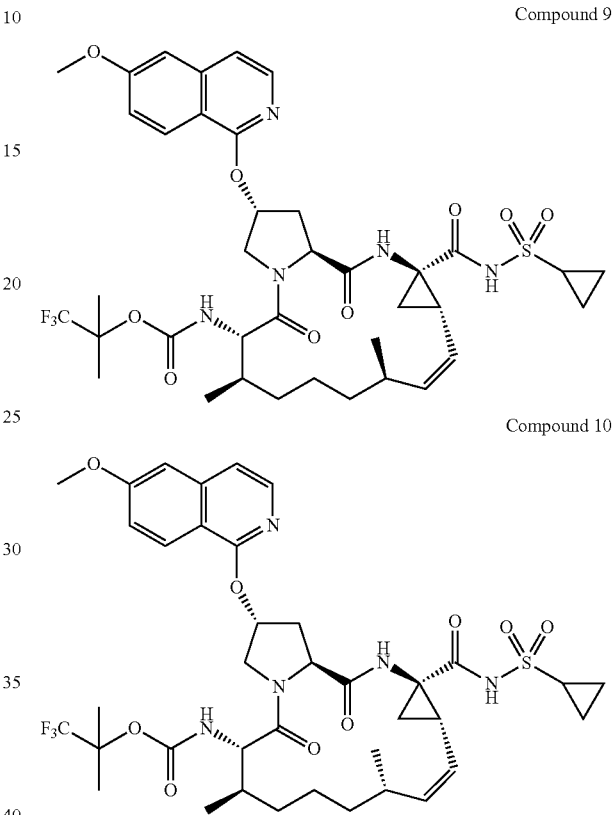

Compound 9 and 10 were prepared using the intermediates described herein and by following the general procedure described for the synthesis of Compound 7 and compound 8.

Compound 9: 1,1,1-trifluoro-2-methylpropan-2-yl (2R,6S,7R,11R,13aS,14aR,16aS,Z)-14a-(cyclopropylsulfonylcarbamoyl)-2-(6-methoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.10-8.08 (d, J=8.8 Hz, 1H), 7.92-7.91 (d, J=6.0 Hz, 1H), 7.26-7.25 (d, J=5.6 Hz, 1H), 7.23 (bs, 1H), 7.20 (s, 1H), 7.12-7.11 (dd, J=2.4 & 6.4 Hz, 1H) 5.88-5.87 (m, 1H), 5.39-5.33 (t, J=10.8 Hz, 1H), 5.04-5.00 (m, 1H), 4.74-4.68 (m, 2H), 4.02-3.99 (m, 1H), 3.99 (s, 3H), 3.88-3.84 (m, 1H), 3.23-3.21 (m, 1H), 2.96-2.90 (m, 1H), 2.72-2.58 (m, 2H), 2.37-2.34 (m, 1H), 1.80-1.76 (m, 1H), 1.72-1.68 (m, 1H), 1.65-1.57 (m, 3H), 1.40-1.28 (m, 6H), 1.21-1.02 (m, 5H), 0.99-0.89 (m, 10H), $^{19}$F NMR: δ ppm −85.15 (3 F); MS: MS m/z 806.2 (M$^+$−1).

Compound 10: 1,1,1-trifluoro-2-methylpropan-2-yl (2R,6S,7R,11S,13aS,14aR,16aS,Z)-14a-(cyclopropylsulfonylcarbamoyl)-2-(6-methoxyisoquinolin-1-yloxy)-7,11-dimethyl-5,16-dioxo-1,2,3,5,6,7,8,9,10,11,13a,14,14a,15,16, 16a-hexadecahydrocyclopropa[e]pyrrolo[1,2-a][1,4]diazacyclopentadecin-6-ylcarbamate. MS: MS m/z 806.2 (M+ +1).

Preparation of 1-Fluoro-4-methoxyisoquinoline

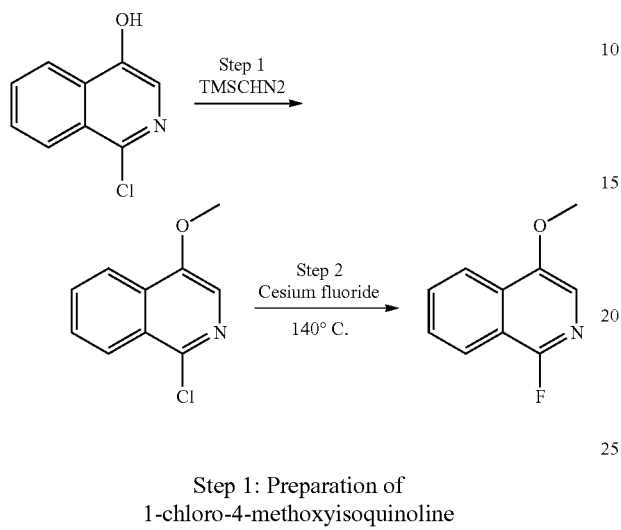

Step 1: Preparation of 1-chloro-4-methoxyisoquinoline

To a solution of 1-chloroisoquinolin-4-ol (5.0 g, 27.8 mmol) in acetonitrile (50 mL) was added TMS-diazomethane (12.73 g, 111.2 mmol) at 0° C. The reaction mixture was allowed to come to room temperature and stirred for 2 h. Solvent was evaporated under reduced pressure to get crude compound. The crude compound was purified by silica gel chromatography to get 1-chloro-4-methoxyisoquinoline (2.5 g, 46.4%) as off-white solid. $^1$H NMR (400 MHz, CD$_3$OD): δ ppm 8.29-8.17 (m, 2H), 7.97 (s, 1H), 7.91-7.82 (m, 2H), 4.05 (s, 3H); MS: MS m/z 194.7 (M+ +1).

Step 2: Preparation of 1-Fluoro-4-methoxyisoquinoline

To a solution of 1-chloro-4-methoxyisoquinolin (2.5 g, 12.91 mmol) in DMSO was added cesium fluoride (4.01 g, 25.82 mmol) at room temperature. The reaction vessel (Pressure tube) was sealed and heated at 145° C. for 18 h. The reaction mass was diluted with water and extracted with ethyl acetate. The organic layer was dried over anhydrous Na$_2$SO$_4$ and evaporated under reduced pressure to get crude compound. The crude compound was purified by silica gel chromatography to get desired compound (700 mg, 62%) as a white solid. $^1$H NMR (400 MHz, CD$_3$OD): δ ppm 8.10 (m, 1H), 8.08 (m, 1H), 7.78-7.75 (m, 1H), 7.69-7.65 (m, 1H), 7.49 (m, 1H), 4.04 (s, 3H); $^{19}$F NMR: δ ppm –78.66 (1 F); MS: MS m/z 178.1 (M+ +1).

Preparation of 1,5-dichloro-4-methoxyisoquinoline

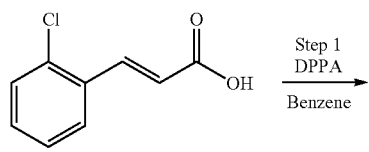

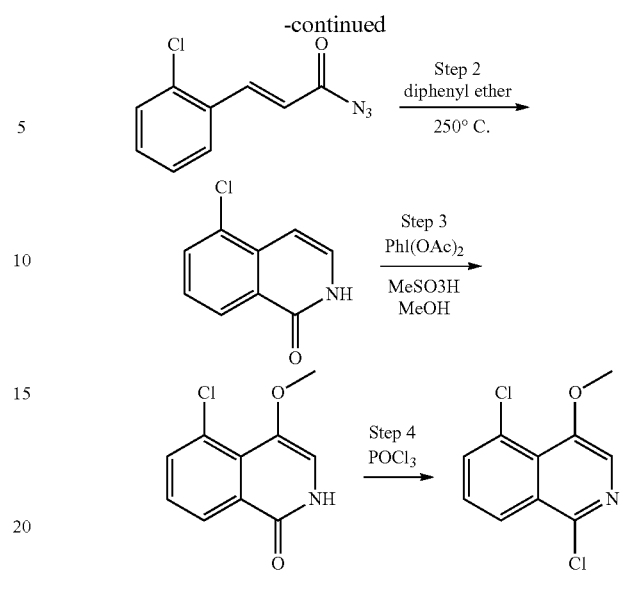

Step 1: Preparation of (E)-3-(2-chlorophenyl)acryloyl azide

To a solution of (E)-3-(2-chlorophenyl)acrylic acid (13 g, 71.2 mmol) in benzene (100 ml) was added triethylamine (14.4 g, 141 mmol) followed by DPPA (19.5 g, 71.2 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as pale yellow solid (14 g, 95%). $^1$H NMR (400 MHz, CDCl$_3$): δ ppm 8.19-8.15 (d, J=16 Hz, 1H), 7.63-7.61 (d, J=8 Hz, 1H), 7.44-7.42 (m, 1H), 7.36-7.26 (m, 2H), 6.44-6.40 (d, J=16 Hz, 1H).

Step 2: Preparation of 5-chloroisoquinolin-1(2H)-one

To a hot (125° C.) diphenyl ether (10 ml) was added (E)-3-(2-chlorophenyl) acryloyl azide (2 g, 9.63 mmol) portion wise. The reaction was heated at 250° C. for 2 h. The reaction mass was cooled to room temperature and diluted with pet ether. The precipitated solid was filtered washed with pet ether to get crude compound (1.1 g, 63.6%) as yellow solid. The crude compound was taken to the next step without further purification. $^1$H NMR (400 MHz, CD$_3$OD): δ ppm 8.29-8.27 (d, J=8 Hz, 1H), 7.84-7.82 (d, J=8 Hz, 1H), 7.49 (t, J=8 Hz, 1H), 7.32-7.30 (d, J=8 Hz, 1H), 6.98-6.96 (d, J=8 Hz, 1H); MS: MS m/z 180.7 (M+ +1).

Step 3: Preparation of 5-chloro-4-methoxyisoquinolin-1-(2H)-one

To a solution of 5-chloroisoquinolin-1(2H)-one (3.8 g, 21.2 mmol) in methanol (70 ml) was added iodosobenzenediacetate (7.5 g, 23.4 mmol) followed by methane sulphonic acid (2.45 g, 25.5 mmol) at room temperature. The reaction mass was heated at reflux for 3 h. The solvent was evaporated and the residue was diluted with cold water. The precipitated solid was filtered, washed with water to get crude compound (3.9 g, 88%) as a light red colored solid. $^1$H NMR (400 MHz, CDCl$_3$): δ ppm 8.06-8.03 (d, J=12 Hz, 1H), 7.60-7.57 (d, J=12 Hz, 1H), 7.42 (d, J=8 Hz, 1H), 7.01-6.99 (br s, 1H), 3.51 (s, 3H); MS: MS m/z 209.1 (M$^+$+1).

Step 4: Preparation of 1,5-dichloro-4-methoxyisoquinoline

A solution of 5-chloro-4-methoxyisoquinolin-1-(2H)-one (6.4 g, 30.5 mmol) in POCl$_3$ (45 ml) was refluxed for 18 h. The solvent was evaporated under reduced pressure and the residue was diluted with cold water. The precipitated solid was filtered, washed with water to get crude compound (4 g, 57.4%) as a light brown colored solid. $^1$H NMR (400 MHz, CDCl$_3$): δ ppm 8.28-8.25 (d, J=12 Hz, 1H), 7.87 (s, 1H), 7.79-7.76 (d, J=12 Hz, 1H), 7.58-7.54 (m, 1H), 4.03 (s, 3H); MS: MS m/z 228.0 (M$^+$+1).

Preparation of 1,7-difluoro-4,6-dimethoxyisoquinoline

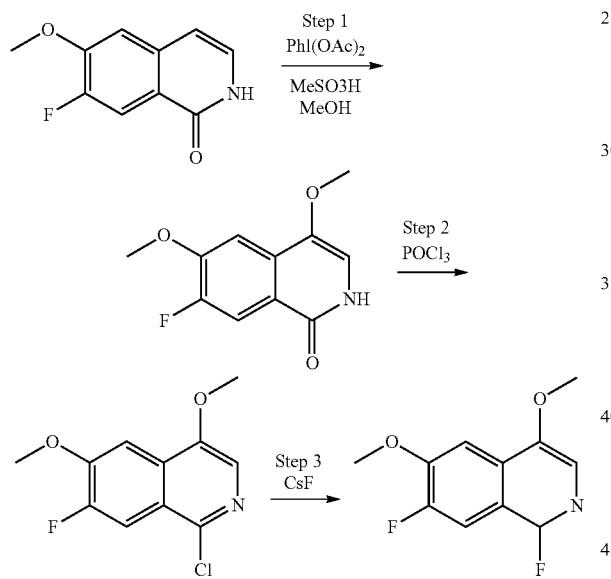

Step 1: Preparation of 7-fluoro-4,6-dimethoxyisoquinolin-1(2H)-one

To a solution of 7-fluoro-6-methoxyisoquinolin-1(2H)-one (6.3 g, 32.6 mmol) in methanol (70 ml) was added iodozobenzenediacetate (10.5 g, 32.6 mmol) followed by methane sulphonic acid (3.76 g, 39.1 mmol) at room temperature. The reaction mass was heated at reflux for 3 h. The solvent was evaporated and the residue was diluted with cold water. The precipitated solid was filtered, washed with water to get crude compound (6.6 g, 91%) as a light red colored solid. MS: MS m/z 224.0 (M$^+$+1).

Step 2: Preparation of 1-chloro-7-fluoro-4,6-dimethoxyisoquinoline

A solution of 7-fluoro-4,6-dimethoxyisoquinolin-1(2H)-one (7.6 g, 34.1 mmol) in POCl$_3$ (50 ml) was refluxed for 18 h. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get desired compound (2 g, 24.3%) as pale yellow solid. $^1$H NMR (400 MHz, CDCl$_3$): δ ppm 7.88-7.85 (d, J=12 Hz, 1H), 7.75 (s, 1H), 7.54-7.52 (d, J=8 Hz, 1H), 4.05 (s, 3H); MS: MS m/z 242.0 (M$^+$+1).

Step 3: Preparation of 1,7-difluoro-4,6-dimethoxyisoquinoline

To a solution of 1-chloro-7-fluoro-4,6-dimethoxyisoquinoline (2 g, 8.28 mmol) in DMSO (5 ml) was added cesium fluoride (2.51 g, 16.55 mmol) at room temperature. The reaction vessel (Pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (475 mg, 25.5%) as white solid. $^1$H NMR (400 MHz, CDCl$_3$): δ ppm 7.69-7.67 (d, J=8 Hz, 1H), 7.53-7.51 (d, J=8 Hz, 1H), 7.45-7.44 (m, 1H), 4.05 (s, 3H), 4.03 (s, 3H); $^{19}$F NMR: δ ppm −129.58 (1 F), −79.2 (1 F); MS: MS m/z 226.0 (M$^+$+1).

Preparation of 1-fluoro-4,6-dimethoxyisoquinoline

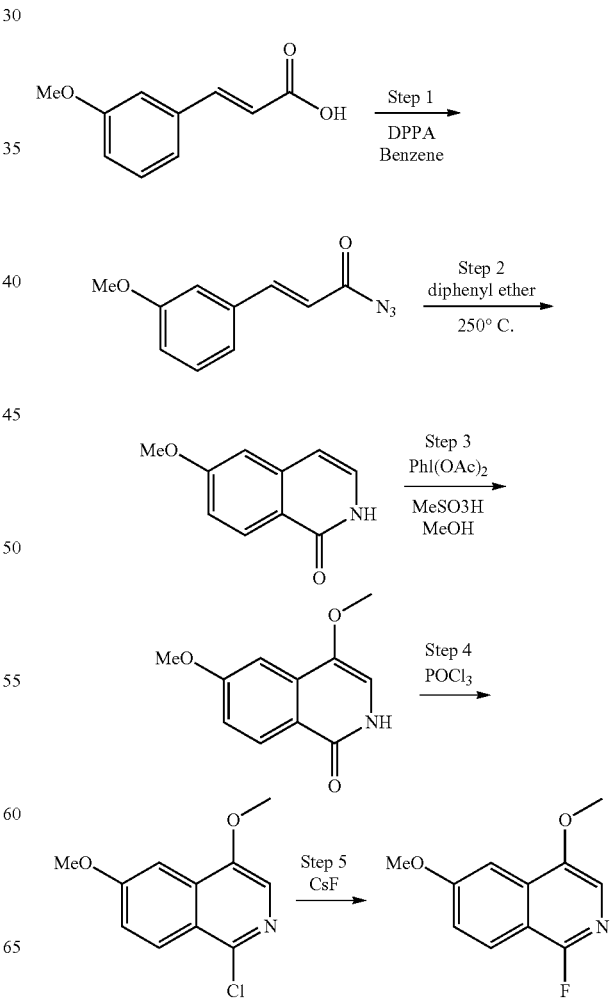

Step 1: Preparation of (E)-3-(3-methoxyphenyl)acrylic azide

To a solution of (E)-3-(3-methoxyphenyl)acrylic acid (20 g, 112 mmol) in benzene (200 ml) was added triethylamine (22.72 g, 224 mmol) followed by DPPA (30.9 g, 112 mmol) at room temperature. The reaction mass was stirred at the same temperature for 18 h. The solvent was evaporated under reduced pressure and the residue was diluted with water and extracted with dichloromethane. Combined organic layer was dried over anhydrous sodium sulfate, filtered and evaporated to get crude compound. The crude compound was purified by conventional column chromatography (Silica gel, 60-120 mesh) using 10% ethyl acetate in pet ether as mobile phase to get the desire compound as white solid (18 g, 79%). $^1$H NMR (400 MHz, CDCl$_3$): δ ppm 7.73-7.69 (d, J=16 Hz, 1H), 7.33-7.29 (t, J=8 Hz, 1H), 7.26 (s, 1H), 7.14-7.12 (d, J=8 Hz, 1H), 7.05 (s, 1H) 6.98-6.96 (d, J=4 Hz, 1H), 6.43-6.39 (d, J=16 Hz, 1H), 3.86 (s, 3H).

Step 2: Preparation of –6-methoxyisoquinolin-1(2H)-one

To a solution of (E)-3-(3-methoxyphenyl)acryloyl azide (7 g, 34.4 mmol) in 1,2-dichlorobenzene (70 ml) was added mercuric acetate (0.11 g, 0.34 mmol). The reaction was heated at 150° C. for 10 min and the temperature was raised to 180° C. for 1 h. The reaction mass was cooled to room temperature and diluted with pet ether. The precipitated solid was filtered washed with pet ether to get crude compound (3.5 g, 58%) as yellow solid. The crude compound was taken to the next step without further purification. $^1$H NMR (400 MHz, DMSO): δ ppm 8.09-8.06 (d, J=12 Hz, 1H), 7.14-7.11 (m, 2H), 7.05-7.03 (d, J=8 Hz, 1H), 6.48-6.46 (d, J=4 Hz, 1H), 3.86 (s, 3H); MS: MS m/z 176.0 (M$^+$+1).

Step 3: Preparation of 4,6-dimethoxyisoquinolin-1(2H)-one

To a solution of 7-fluoro-6-methoxyisoquinolin-1(2H)-one (7 g, 40.0 mmol) in methanol (70 ml) was added iodozobenzenediacetate (14.16 g, 40.0 mmol) followed by methane sulphonic acid (11.52 g, 120 mmol) at room temperature. The reaction mass was heated at reflux for 3 h. The solvent was evaporated and the residue was diluted with cold water. The precipitated solid was filtered, washed with water to get crude compound (4 g, 48.8%) as a light red colored solid. $^1$H NMR (400 MHz, DMSO): δ ppm 8.11-8.09 (d, J=8 Hz, 1H), 7.19 (s, 1H), 7.13-7.11 (d, J=8 Hz, 1H), 6.72-6.71 (d, J=12 Hz, 1H), 3.89 (s, 3H), 3.79 (s, 3H); MS: MS m/z 206.1 (M$^+$+1).

Step 4: Preparation of 1-chloro-4,6-dimethoxyisoquinoline

A solution of 4,6-dimethoxyisoquinolin-1(2H)-one (4 g, 19.49 mmol) in POCl$_3$ (40 mL) was refluxed for 18 h. The solvent was evaporated under reduced pressure and the residue was diluted with cold water. The aqueous solution was basified by solid sodium carbonate and extracted with ethyl acetate. The organic layer was dried over anhydrous sodium sulfate, filtered and evaporated under reduced pressure to get crude compound. The crude compound was purified by silica gel chromatography (20% ethyl acetate in pet ether) to get desired compound (1.2 g, 27.5%) as pale yellow solid. $^1$H NMR (400 MHz, CDCl$_3$): δ ppm 8.16-8.13 (d, J=12 Hz, 1H), 7.74 (s, 1H), 7.44-7.43 (d, J=4 Hz, 1H), 7.30-7.27 (d, J=12 Hz, 1H), 7.26 (s, 1H), 4.05 (s, 3H), 3.97 (s, 3H); MS: MS m/z 224.2 (M$^+$+1).

Step 5: Preparation of 1-fluoro-4,6-dimethoxyisoquinoline

To a solution of 1-chloro-4,6-dimethoxyisoquinoline (1.5 g, 6.71 mmol) in DMSO (15 ml) was added cesium fluoride (4 g, 26.8 mmol) at room temperature. The reaction vessel (Pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (280 mg, 20.15%) as white solid. $^1$H NMR (400 MHz, CDCl$_3$): δ ppm 7.99-7.97 (d, J=8 Hz, 1H), 7.44-7.39 (m, 2H), 7.27-7.11 (m, 1H), 4.03 (s, 3H), 3.97 (s, 3H); $^{19}$F NMR: δ ppm –79.32 (1 F); MS: MS m/z 208.0 (M$^+$+1).

Preparation of 1-chloro-7-fluoro-4-methoxyisoquinoline

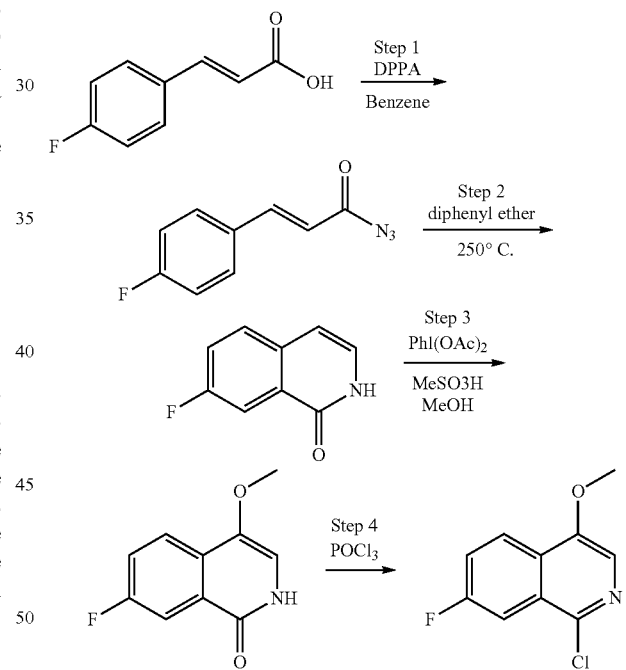

Step 1: Preparation of (E)-3-(4-fluorophenyl)acryloyl azide

To a solution of (E)-3-(4-fluorophenyl)acrylic acid (25 g, 150 mmol) in benzene (120 mL) was added triethylamine (30.5 g, 301 mmol) followed by DPPA (41.4 g, 150 mmol) at room temperature. The reaction mass was stirred at the same temperature for 18 h. The solvent was evaporated under reduced pressure and the residue was diluted with water and extracted with dichloromethane. The organic layer was dried over anhydrous sodium sulfate, filtered and evaporated to get crude compound. The crude compound was purified by conventional column chromatography (Silica gel, 60-120 mesh)

using 10% ethyl acetate in pet ether as mobile phase to get the desired compound as a white solid (26 g, 90%). $^1$H NMR (400 MHz, CDCl$_3$): δ ppm 7.73-7.69 (d, J=16 Hz, 1H), 7.55-7.51 (m, 2H), 7.11-7.07 (m, 2H), 6.36-6.32 (d, J=16 Hz, 1H).

Step 2: Preparation of 7-fluoroisoquinolin-1(2H)-one

To a hot (125° C.) diphenyl ether (25 ml) was added (E)-3-(4-fluorophenyl)acryloyl azide (5 g, 26.2 mmol) portion wise. The reaction was heated at 250° C. for 4 h. The reaction mass was cooled to room temperature and diluted with pet ether. The precipitated solid was filtered washed with pet ether to get crude compound (2.45 g, 57%). The crude compound was taken to the next step without further purification. $^1$H NMR (400 MHz, CD$_3$OD): δ ppm 7.96-7.93 (m, 1H), 7.76-7.72 (m, 1H), 7.56-7.51 (m, 1H), 7.18-7.16 (m, 1H), 6.72-6.70 (m, 1H); MS: MS m/z 164.1 (M$^+$+1).

Step 3: Preparation of 7-fluoro-4-methoxyisoquinolin-1(2H)-one

To a solution of 7-fluoroisoquinolin-1(2H)-one (11 g, 67.4 mmol) in methanol was added iodozobenzenediacetate (21.7 g, 67.4 mmol) followed by methane sulphonic acid (7.78 g, 81 mmol) at room temperature. The reaction mass was heated at reflux for 3 h. The solvent was evaporated and the residue was diluted with cold water. The precipitated solid was filtered and washed with water to get crude compound (11 g, 84%) as light red color solid. $^1$H NMR (400 MHz, CD$_3$OD): δ ppm 8.06-8.04 (m, 1H), 7.96-7.93 (m, 1H), 7.62-7.54 (m, 2H), 6.74 (s, 1H), 3.89 (s, 3H); MS: MS m/z 194.1 (M$^+$+1).

Step 4: Preparation of 1-chloro-7-fluoro-4-methoxyisoquinoline

A solution of 7-fluoro-4-methoxyisoquinolin-1(2H)-one (11 g, 56.9 mmol) in POCl$_3$ (100 ml) was refluxed for 18 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to get desired compound (2.9 g, 24%) as off-white solid. $^1$H NMR (400 MHz, CDCl$_3$): δ ppm 8.36-8.32 (m, 1H), 7.93-7.90 (m, 1H), 7.88 (s, 1H), 7.70-7.65 (m, 1H), 4.11 (s, 3H); MS: MS m/z 212.1 (M$^+$+1).

Preparation of 1,7-difluoro-4-methoxyisoquinoline

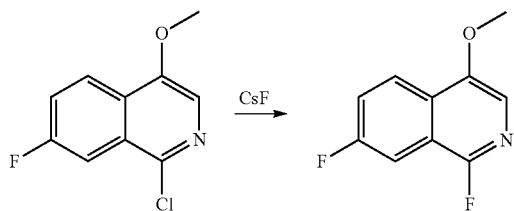

To a solution of 1-chloro-7-fluoro-4-methoxyisoquinoline (3.7 g, 17.48 mmol) in DMSO was added cesium fluoride (10.26 g, 69.9 mmol) at room temperature. The reaction vessel (Pressure tube) was sealed and heated at 145° C. for 18 h. The reaction mass was diluted with water and extracted with ethyl acetate. The combined organic layer was dried over anhydrous Na$_2$SO$_4$ and evaporated under reduced pressure to get crude compound. The crude compound was purified by silica gel chromatography to get desired compound (1.7 g, 49%) as white solid. $^1$H NMR (400 MHz, CD$_3$OD): δ ppm 8.20-8.18 (m, 1H), 7.69-7.66 (m, 1H), 7.54-7.47 (m, 1H), 7.46 (s, 1H), 4.04 (s, 3H); $^{19}$F NMR: δ ppm 109.65 (1 F), −78.53 (1 F); MS: MS m/z 196.1 (M$^+$+1).

Preparation of 2-chloro-6-methoxyquinoxaline and 3-chloro-6-methoxyquinoxaline

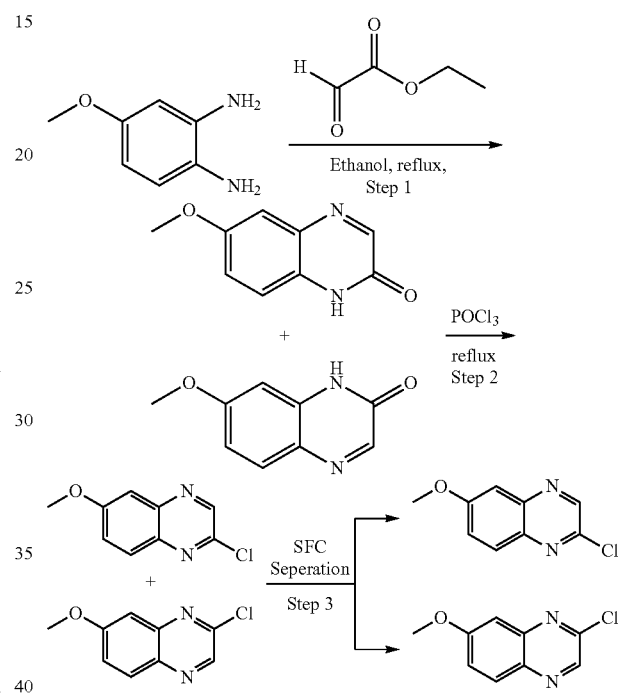

Step 1: Preparation of 6-methoxylquinoxalin-2(1H)-one and 7-methoxyquinoxalin-2(1H)-one To a solution of 4-methoxybenzene-1,2-diamine (5 g, 36.2 mmol) in ethanol (50 ml) was added ethyl 2-oxoacetate (4.06 g, 39.8 mmol)). The reaction mass was heated at reflux for overnight. The solvent was evaporated under reduced pressure and the residue was diluted with ethyl acetate and then evaporated to dryness to get the crude compound. The crude compound was washed with pet ether to get crude compound (5.1 g, 80% yield) as a mixture of regioisomers (black solid). This crude compound was taken to the next step without separation of isomers. $^1$H NMR (400 MHz, DMSO-d$_6$): δ ppm 8.17 (s, 1H), 7.98 (s, 1H), 7.70-7.68 (d, J=8 Hz, 1H), 7.31-7.30 (d, J=4 Hz, 1H), 7.27-7.20 (m, 2H), 6.93-6.90 (m, 1H), 6.77-6.76 (d, J=4 Hz, 1H), 3.84 (s, 3H), 3.83 (s, 3H); MS: MS m/z 177.0 (M$^+$+1).

Steps 2 and 3: Preparation of 2-chloro-6-methoxyquinoxaline and 3-chloro-6-methoxyquinoxaline A solution of 6-methoxyquinoxalin-2(1H)-one & 7-methoxyquinoxalin-2(1H)-one (3 g, 18.28 mmol) in POCl$_3$ (20 ml) was refluxed for 3 h. The solvent was evaporated under reduced pressure and the residue was diluted with cold water. The aqueous solution was basified by solid sodium carbonate and extracted with ethyl acetate. The combine organic layer was dried over anhydrous sodium sulfate, filtered and evaporated under reduced pressure to get crude compound. The crude compound was purified by silica gel chromatography (20% ethyl acetate in pet ether) to afford mixture of regioisomers (3.7 g). 2 g of the above mixture was separated by SFC purification to afford 2-chloro-7-methoxyquinoxaline (0.7 g, 34.7%) and 2-chloro-7-methoxyquinoxaline (0.9 g, 44.6%) as off white solid.

2-chloro-6-methoxyquinoxaline: $^1$H NMR (400 MHz, DMSO-d6): δ ppm $^1$H NMR (400 MHz, CDCl$_3$): δ ppm 8.71 (s, 1H), 7.91-7.89 (d, J=8 Hz, 1H), 7.46-7.38 (m, 2H), 3.97 (s, 3H); MS: MS m/z 194.9 (M$^+$+1).

2-chloro-7-methoxyquinoxaline: $^1$H NMR (400 MHz, CDCl$_3$): δ ppm 8.63 (s, 1H), 7.99-7.96 (d, J=12 Hz, 1H), 7.43-7.40 (d, J=12 Hz, 1H), 7.30 (s, 1H), 3.96 (s, 3H); MS: MS m/z 194.9 (M$^+$+1).

Preparation of 1-fluoro-4-ethoxyisoquinoline

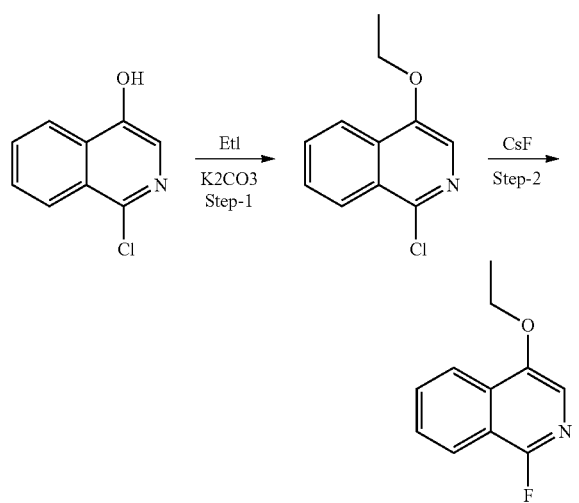

Step 1: Preparation of 1-chloro-4-ethoxyisoquinoline

To a solution of 1-chloroisoquinolin-4-ol (1.0 g, 5.5 mmol) in acetonitrile (10 mL) was added K$_2$CO$_3$ (2.3 g, 16.7 mmol) followed by ethyl iodide (0.87 ml, 11.0 mmol) at room temperature. The reaction mixture was stirred at room temperature for overnight. The solvent was evaporated under reduced pressure and the residue was diluted with water and extracted with ethyl acetate. The combined organic layer was dried over anhydrous Na$_2$SO$_4$ and evaporated under reduced pressure to get crude compound. The crude compound was purified by silica gel chromatography to get 1-chloro-4-ethoxyisoquinoline (0.7 g, 62%) as off-white solid. $^1$H NMR (400 MHz, CD$_3$OD): δ ppm 8.26-8.24 (m, 2H), 7.79 (s, 1H), 7.76-7.26 (m, 2H), 4.29-4.24 (q, J=6.8 Hz, 2H), 1.58-1.54 (t, J=6.8 Hz, 3H); MS: MS m/z 207.7 (M$^+$+1).

Step 2: Preparation of 1-Fluoro-4-ethoxyisoquinoline

To a solution of 1-chloro-4-ethoxyisoquinolin (4.8 g, 23.12 mmol) in DMSO was added cesium fluoride (6.9 g, 46.24 mmol) at room temperature. The reaction vessel (Pressure tube) was sealed and heated at 145° C. for 18 h. The reaction mass was diluted with water and extracted with ethyl acetate. The organic layer was dried over anhydrous Na$_2$SO$_4$ and evaporated under reduced pressure to get crude compound. The crude compound was purified by silica gel chromatography to get desired compound (2.6 g, 58.8%) as white solid. MS: MS m/z 192.3 (M$^+$+1).

Preparation of 1-methylcyclopropane-1-sulfonamide

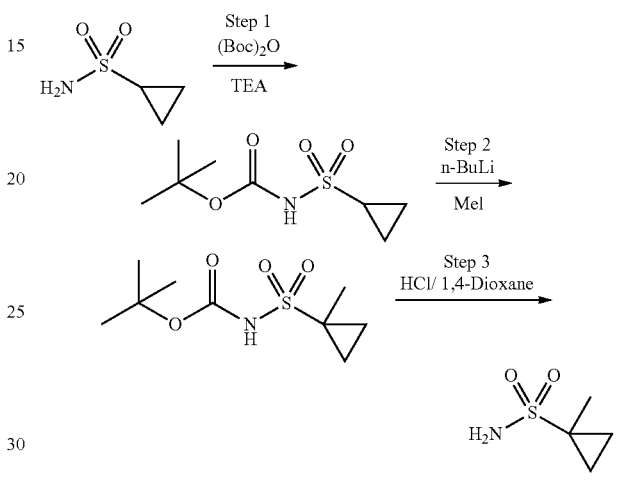

Step 1: Preparation of tert-butyl cyclopropylsulfonylcarbamate

To a solution of cyclopropanesulfonamide (100 g, 82.6 mmol) in DCM (800 ml) was added triethylamine (234 ml, 165 mmol) followed by DMAP (10.28 g, 82.6 mmol) at 0° C. under nitrogen. To this reaction mixture Boc anhydride (247 ml, 107 mmol) in DCM (400 ml) was added slowly. The resulting mixture was stirred for 4 h at room temperature. The reaction mixture was diluted with water and extracted with ethyl acetate. The combine organic layer was washed with 1.5 N HCl solution and 10% NaHCO$_3$ and dried over anhydrous sodium sulfate, filtered and evaporated under reduced pressure to get crude compound (143 g, 65.0%) as solid. The crude compound was directly taken for the next step. $^1$H NMR (400 MHz, DMSO-d6): δ ppm 11.08 (s, 1H), 2.90 (m, 1H), 1.48 (s, 9H), 1.06 (m, 4H).

Step 2: Preparation of tert-butyl (1-methylcyclopropyl)sulfonylcarbamate

A solution of tert-butyl cyclopropylsulfonylcarbamate (4.3 g, 20 mmol) was dissolved in dry THF (100 ml) and cooled to −78° C. To this solution was added n-BuLi (17.6 ml, 44 mmol, 2.5 M in hexane) slowly. The reaction mixture was allowed to warm to room temperature over a period of 1.5 h. This mixture was then cooled to −78° C., and a solution of n-BuLi (20 mmol, 8 ml, 2.5M in hexane) was added, stirred for 1 h and a neat solution of methyl iodide (5.68 g, 40 mmol) was added. The reaction mixture was allowed to warm to room temperature for overnight, quenched with aqueous saturated NH$_4$Cl (100 ml) at room temperature. It was extracted with EtOAc (100 ml). The combined organic layer was washed with brine dried on Na$_2$SO$_4$, filtered and evaporated under reduced pressure to give a yellow oil which was crystallized from hexane to afford the product as a slightly yellow solid. (3.1 g, 81%). $^1$H NMR (400 MHz, DMSO-$d_6$): δ ppm 10.97 (s, 1H), 1.44 (s, 12H), 1.35-1.33 (m, 2H), 0.93-0.91 (m, 2H).

Step 3: Preparation of 1-methylcyclopropane-1-sulfonamide

A solution of N-tert-butyl-(1-methyl)cyclopropyl-sulfonamide (1.91 g, 10 mmol) was dissolved in 4M HCl in dioxane (30 ml) and the reaction mixture stirred at rt for 16 h. The solvent was removed in vacuo to give a yellow oil which was crystallized from EtOAc/hexane (1:4, 40 ml) to yield 1-methyl-cyclopropylsulfonamide, as a white solid (1.25 g, 96%). $^1$H NMR (400 MHz, CDCl$_3$): δ ppm 6.73 (s, 2H), 1.43 (s, 3H), 1.14-1.12 (m, 2H), 0.75-0.73 (m, 2H).

Preparation 1-(Fluoro methyl)cyclopropane-1-sulfonamide

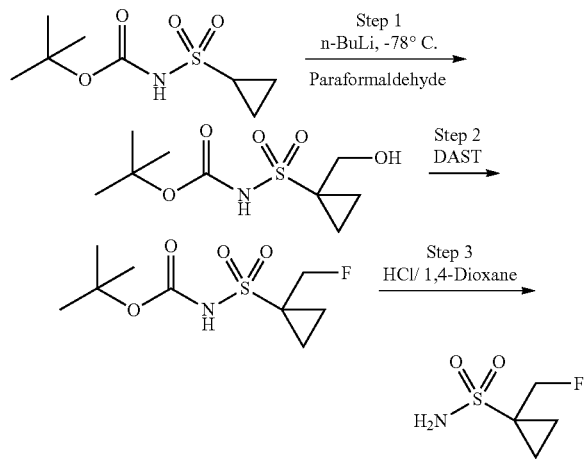

Step 1: Preparation of tert-butyl 1-(hydroxymethyl)cyclopropylsulfonylcarbamate To a solution of tert-butyl cyclopropylsulfonylcarbamate (30 g, 136 mmol) in 750 mL of THF was added dropwise butyllithium (1.6 M in hexane, 212 mL, 339 mmol) over 30 min at −78° C. and the resulting mixture was stirred at −78° C. for 1 h. Formaldehyde gas was generated from para-formaldehyde (by heating at 180° C.) and was purged into the above reaction mass for 30 min at −30° C. The reaction was stirred at the same temperature for 1 h, then allowed to warm to room temperature. The reaction was quenched with aqueous ammonium chloride solution and diluted with water. The resulting mass was washed with ethyl acetate and the aqueous layer was acidified to pH~2 and extracted with ethyl acetate. The combined organics were dried over sodium sulfate, filtered and evaporated under reduced pressure to get desired compound (27 g, 79%) as white solid. $^1$H NMR (400 MHz, DMSO-$d_6$): δ ppm 10.90 (sb, 1H), 4.95 (sb, 1H), 3.75 (s, 2H), 1.42 (s, 9H), 1.27 (m, 2H), 1.08 (m, 2H).

Step 2: Preparation of tert-butyl (1-(fluoromethyl)cyclopropyl)sulfonylcarbamate To a solution of tert-butyl (1-hydroxymethyl)cyclopropyl) sulfonylcarbamate (10 g, 39.98 mmol) in DCM (150 ml) at −78° C. was added DAST (25.7 g, 159 mmol) drop wise. The reaction mass was stirred for 2 hr. The reaction mass was quenched with 1N NaOH solution (200 ml), separated the DCM layer. The DCM layer was washed with NaOH solution (400 ml), combined aqueous layer was acidified with 1.5N HCl solution (600 ml) and extracted with DCM. The combine organic layer was dried over anhydrous sodium sulfate, filtered and evaporated under reduced pressure to get desired compound (9.8 g, 97%) as a light brown solid. $^1$H NMR (400 MHz, CDCl$_3$): δ ppm 6.97 (br, s, 1H), 4.74-4.62 (d, J=48 Hz, 2H), 1.83-1.80 (m, 2H), 1.56-1.44 (m, 9H), 1.20-1.11 (m, 2H).

Step 3: Preparation of 1-(fluoromethyl)cyclopropane-1-sulfonamide

To a solution of tert-butyl (1-(fluoromethyl)cyclopropyl) sulfonylcarbamate (19.8 g, 38.7 mmol) in DCM (100 ml) was added TFA (30 ml, 387 mmol) drop wise at room temperature. The reaction mass was stirred for 2 hr. The reaction mass was evaporated under reduced pressure to get desired compound (6 g, 100%) as off white solid. $^1$H NMR (400 MHz, CDCl$_3$): δ ppm 4.78-4.66 (d, J=48 Hz, 2H), 2.61 (br, s, 1H), 1.59-1.56 (m, 2H), 1.13-1.10 (m, 2H).

Preparation of Compound 11

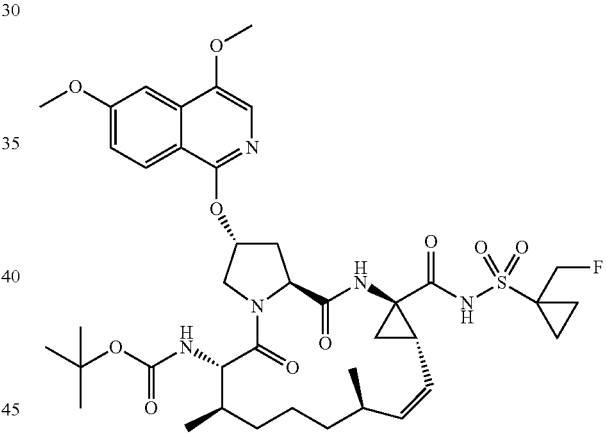

Compound 11 was prepared using the intermediates described herein and by following the general procedure described for the synthesis of Compound 5. Compound 11: tert-butyl (2R,6S,7R,11R,13aS,14aR,16aS,Z)-2-(4,6-dimethoxyisoquinolin-1-yloxy)-14a-(1-(fluoromethyl)cyclopropylsulfonylcarbamoyl)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.06 (d, J=9.03 Hz, 1H) 7.51 (s, 1H) 7.42 (d, J=2.51 Hz, 1H) 7.14 (dd, J=9.16, 2.64 Hz, 1H) 5.79 (br. s., 1H) 5.29 (br. s., 1H) 4.54-4.65 (m, 2H) 4.02 (s, 3H) 3.95 (s, 3H) 3.03-3.09 (m, 3H) 2.67 (d, J=17.57 Hz, 2H) 1.77 (d, J=4.77 Hz, 1H) 1.62 (d, J=11.80 Hz, 2H) 1.43 (s, 1H) 1.29-

1.35 (m, 9H) 1.24 (br. s., 2H) 1.12 (s, 9H) 0.99 (dd, J=13.05, 6.53 Hz, 6H) 0.89-0.94 (m, 3H); MS: MS m/z 816.4 (M⁺+1).

Preparation of Compound 12 and Compound 13

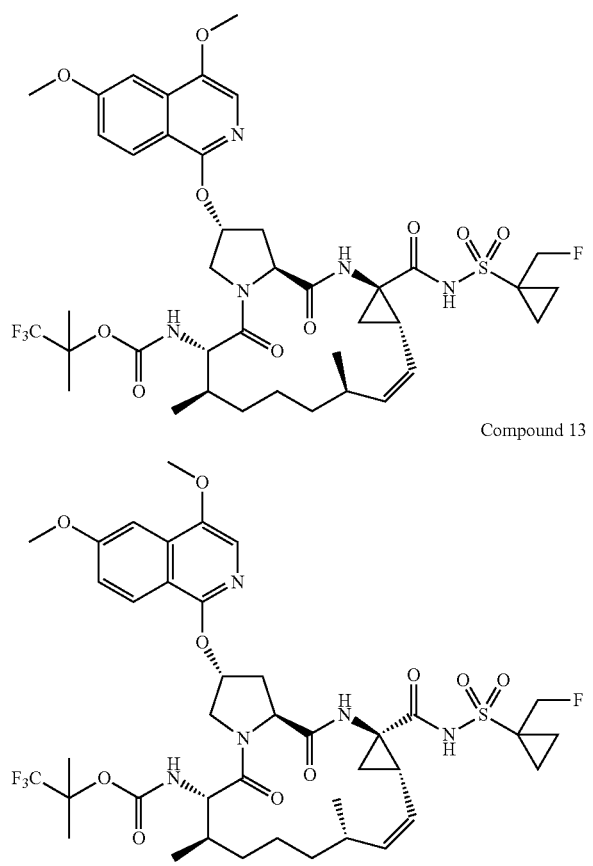

Compound 12

Compound 13

Compound 12 and Compound 13 were prepared using the intermediates described herein and by following the general procedure described for the synthesis of Compound 7 and Compound 8.

Compound 12: 1,1,1-trifluoro-2-methylpropan-2-yl (2R,6S,7R,11R,13aS,14aR,16aS,Z)-2-(4,6-dimethoxyisoquinolin-1-yloxy)-14a-(1-(fluoromethyl)cyclopropylsulfonylcarbamoyl)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.89 (s, 1H) 8.09 (d, J=9.29 Hz, 1H) 7.52 (s, 1H) 7.45 (d, J=2.51 Hz, 1H) 7.17 (dd, J=9.03, 2.51 Hz, 1H) 5.81 (br. s., 1H) 5.37 (t, J=9.66 Hz, 1H) 4.96-5.03 (m, 2H) 4.67-4.75 (m, 2H) 4.43-4.61 (m, 1H) 4.00-4.05 (m, 3H) 3.96 (s, 3H) 3.85 (d, J=10.79 Hz, 1H) 3.23 (d, J=7.03 Hz, 2H) 2.59-2.71 (m, 2H) 2.29-2.36 (m, 1H) 1.70-1.82 (m, 2H) 1.63 (td, J=8.47, 5.40 Hz, 4H) 1.36 (s, 3H) 1.31 (s, 3H) 1.25-1.28 (m, 3H) 1.15-1.21 (m, 2H) 0.97 (d, J=4.52 Hz, 6H) 0.87-0.93 (m, 2H); MS: MS m/z 870.4 (M⁺+1).

Compound 13: 1,1,1-trifluoro-2-methylpropan-2-yl((2R,6S,7R,11S,13aS,14aR,16aS,Z)-2-((4,6-dimethoxyisoquinolin-1-yl)oxy)-14a-(((1-(fluoromethyl)cyclopropyl)sulfonyl)carbamoyl)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)carbamate. ¹H NMR (400 MHz, CD₃OD): δ ppm 8.07 (d, J=9.29 Hz, 1H) 7.52 (s, 1H) 7.42 (d, J=2.26 Hz, 1H) 7.09-7.16 (m, 1H) 6.71 (d, J=8.53 Hz, 1H) 5.80 (s, 1H) 5.34 (br. s., 1H) 4.81-4.81 (m, 1H) 4.62-4.71 (m, 3H) 4.02 (s, 4H) 3.95 (s, 4H) 2.67-2.75 (m, 3H) 2.42 (br. s., 1H) 1.83 (br. s., 1H) 1.66 (d, J=7.53 Hz, 6H) 1.48 (br. s., 1H) 1.17 (s, 11H) 1.00 (d, J=6.53 Hz, 3H) 0.95 (d, J=6.27 Hz, 4H); MS: MS m/z 870.6 (M⁺+1).

Preparation of Compound 14

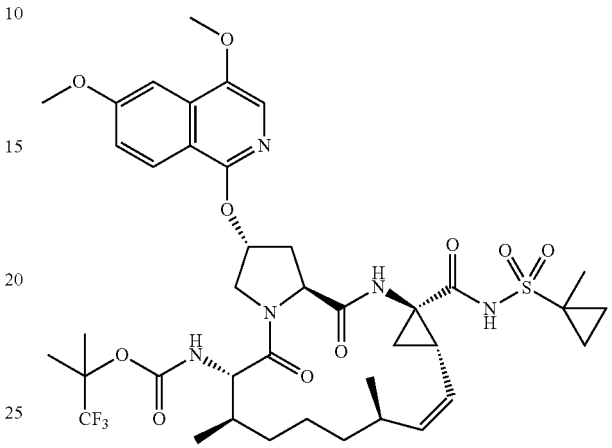

Compound 14 was prepared using the intermediates described herein and by following the general procedure described for the synthesis of Compound 7.

Compound 14: 1,1,1-trifluoro-2-methylpropan-2-yl (2R,6S,7R,11R,13aS,14aR,16aS,Z)-2-(4,6-dimethoxyisoquinolin-1-yloxy)-7,11-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.07 (d, J=9.03 Hz, 1H) 7.53 (s, 1H) 7.44 (d, J=2.51 Hz, 1H) 7.28 (d, J=8.28 Hz, 1H) 7.15 (dd, J=9.03, 2.51 Hz, 1H) 5.81 (br. s., 1H) 5.34-5.40 (m, 1H) 5.02 (dd, J=10.42, 7.40 Hz, 1H) 4.67-4.74 (m, 2H) 3.98-4.04 (m, 4H) 3.95 (s, 3H) 3.84-3.90 (m, 1H) 3.20 (br. s., 1H) 2.58-2.72 (m, 2H) 2.35 (q, J=8.11 Hz, 1H) 1.79 (d, J=7.03 Hz, 1H) 1.57-1.69 (m, 5H) 1.54 (s, 3H) 1.42-1.51 (m, 2H) 1.37 (s, 3H) 1.27-1.33 (m, 1H) 1.17 (dd, J=14.18, 8.91 Hz, 1H) 0.96-1.00 (m, 8H) 0.89-0.93 (m, 3H); MS: MS m/z 852.5 (M⁺+1).

Preparation of Compound 15 and Compound 16

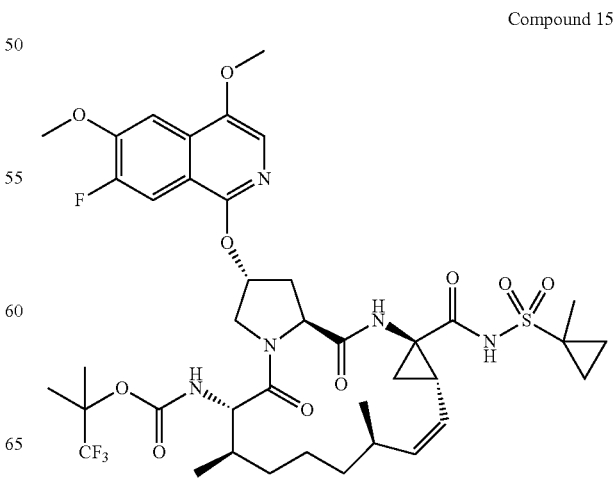

Compound 15

-continued

Compound 16

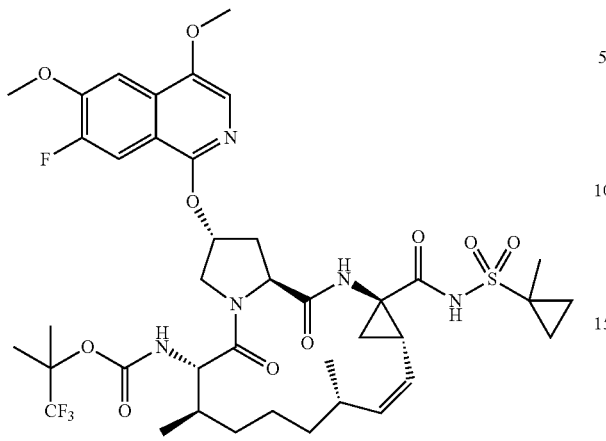

Compound 15 and Compound 16w as prepared using the intermediates described herein and by following the general procedure described for the synthesis of Compound 7 and Compound 8.

Compound 15: 1,1,1-trifluoro-2-methylpropan-2-yl (2R, 6S,7R,11R,13aS,14aR,16aS,Z)-2-(7-fluoro-4,6-dimethoxy-isoquinolin-1-yloxy)-7,11-dimethyl-14a-(1-methylcyclo-propylsulfonylcarbamoyl)-5,16-dioxo-1,2,3,5,6,7,8,9,10,11, 13a,14,14a,15,16,16a-hexadecahydrocyclopropa[e]pyrrolo [1,2-a][1,4]diazacyclopentadecin-6-ylcarbamate. $^1$H NMR (400 MHz, CD$_3$OD): δ ppm 7.75 (d, J=11.54 Hz, 1H) 7.58 (d, J=8.28 Hz, 1H) 7.54 (s, 1H) 5.82 (br. s., 1H) 5.33-5.40 (m, 1H) 5.04 (d, J=10.54 Hz, 1H) 4.64-4.73 (m, 2H) 3.97-4.05 (m, 7H) 3.86 (d, J=10.79 Hz, 1H) 2.57-2.72 (m, 2H) 2.34 (d, J=6.53 Hz, 1H) 1.79 (d, J=6.78 Hz, 1H) 1.57-1.70 (m, 5H) 1.53 (s, 3H) 1.48 (d, J=11.04 Hz, 1H) 1.39 (s, 3H) 1.32 (br. s., 1H) 1.12-1.29 (m, 3H) 1.08 (s, 3H) 0.98 (d, J=6.53 Hz, 6H) 0.87-0.93 (m, 3H); MS: MS m/z 870.4 (M$^+$+1).

Compound 16: 1,1,1-trifluoro-2-methylpropan-2-yl (2R, 6S,7R,11S,13aS,14aR,16aS,Z)-2-(7-fluoro-4,6-dimethoxy-isoquinolin-1-yloxy)-7,11-dimethyl-14a-(1-methylcyclo-propylsulfonylcarbamoyl)-5,16-dioxo-1,2,3,5,6,7,8,9,10,11, 13a,14,14a,15,16,16a-hexadecahydrocyclopropa[e]pyrrolo [1,2-a][1,4]diazacyclopentadecin-6-ylcarbamate. $^1$H NMR (400 MHz, CD$_3$OD): δ ppm 7.75 (d, J=11.54 Hz, 1H) 7.58 (d, J=8.28 Hz, 1H) 7.54 (s, 1H) 5.81 (br. s., 1H) 5.36 (t, J=10.29 Hz, 1H) 4.95 (t, J=10.42 Hz, 1H) 4.65-4.72 (m, 2H) 4.03 (d, J=2.01 Hz, 7H) 3.83 (d, J=10.29 Hz, 1H) 2.73 (dt, J=13.93, 6.84 Hz, 3H) 2.36-2.44 (m, 1H) 1.85 (br. s., 1H) 1.57-1.74 (m, 5H) 1.54 (s, 3H) 1.45 (d, J=11.80 Hz, 2H) 1.41 (s, 3H) 1.30 (d, J=14.05 Hz, 3H) 1.14 (s, 4H) 1.01 (d, J=6.27 Hz, 3H) 0.95 (d, J=6.53 Hz, 3H) 0.91 (br. s., 2H); MS: MS m/z 868.9 (M$^+$−1).

Preparation of Compound 17 and Compound 18

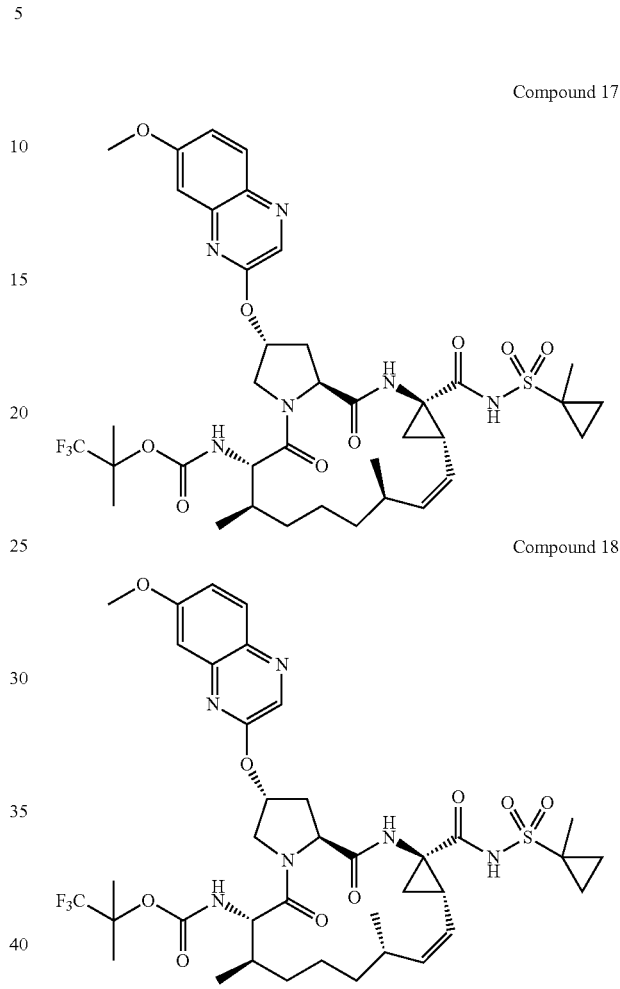

Compound 17 and Compound 18 was prepared using the intermediates described herein and by following the general procedure described for the synthesis of Compound 7 and Compound 8.

Compound 17: 1,1,1-trifluoro-2-methylpropan-2-yl((2R, 6S,7R,11R,13aS,14aR,16aS,Z)-2-((7-methoxyquinoxalin-2-yl)oxy)-7,11-dimethyl-14a-(((1-methylcyclopropyl)sulfo-nyl)carbamoyl)-5,16-dioxo-1,2,3,5,6,7,8,9,10,11,13a,14, 14a,15,16,16a-hexadecahydrocyclopropa[e]pyrrolo[1,2-a] [1,4]diazacyclopentadecin-6-yl)carbamate NMR (400 MHz, CD$_3$OD): δ ppm 8.26 (s, 1H) 7.87 (d, J=9.03 Hz, 1H) 7.32 (d, J=2.76 Hz, 1H) 7.26-7.30 (m, 1H) 5.88 (br. s., 1H) 5.34 (br. s., 1H) 4.75 (s, 1H) 4.68 (br. s., 1H) 4.07 (d, J=8.78 Hz, 1H) 3.99 (s, 3H) 3.84 (s, 1H) 2.66 (d, J=7.03 Hz, 2H) 2.27 (br. s., 1H) 1.74-1.83 (m, 1H) 1.69 (br. s., 1H) 1.60 (d, J=8.03 Hz, 3H) 1.54 (s, 4H) 1.40 (d, J=6.27 Hz, 3H) 1.31 (s, 2H) 1.26 (s, 4H) 1.20 (s, 3H) 0.97 (dd, J=13.68, 6.40 Hz, 7H) 0.88 (br. s., 2H); MS: MS m/z 823.5 (M$^+$+1).

Compound 18: 1,1,1-trifluoro-2-methylpropan-2-yl((2R, 6S,7R,11S,13aS,14aR,16aS,Z)-2-((7-methoxyquinoxalin-2-yl)oxy)-7,11-dimethyl-14a-(((1-methylcyclopropyl)sulfo-nyl)carbamoyl)-5,16-dioxo-1,2,3,5,6,7,8,9,10,11,13a,14, 14a,15,16,16a-hexadecahydrocyclopropa[e]pyrrolo[1,2-a] [1,4]diazacyclopentadecin-6-yl)carbamate. $^1$H NMR (400

MHz, CD₃OD): δ ppm 8.27 (s, 1H) 7.87 (d, J=9.03 Hz, 1H) 7.34 (d, J=2.51 Hz, 1H) 7.28 (dd, J=9.03, 2.76 Hz, 1H) 5.88 (br. s., 1H) 5.32 (t, J=10.29 Hz, 1H) 4.73-4.81 (m, 1H) 4.66 (t, J=8.41 Hz, 1H) 4.12 (d, J=10.54 Hz, 1H) 3.99 (s, 3H) 3.84 (d, J=10.29 Hz, 1H) 2.70 (dd, J=13.93, 7.65 Hz, 3H) 2.45-2.59 (m, 2H) 1.98 (s, 2H) 1.85 (d, J=6.02 Hz, 1H) 1.70-1.77 (m, 2H) 1.61 (br. s., 3H) 1.54 (s, 3H) 1.31-1.47 (m, 2H) 1.28 (s, 4H) 1.23 (s, 3H) 0.96 (t, J=6.90 Hz, 6H) 0.87 (br. s., 2H); MS: MS m/z 823.5 (M⁺+1).

Preparation of Compound 19 and Compound 20

Compound 19

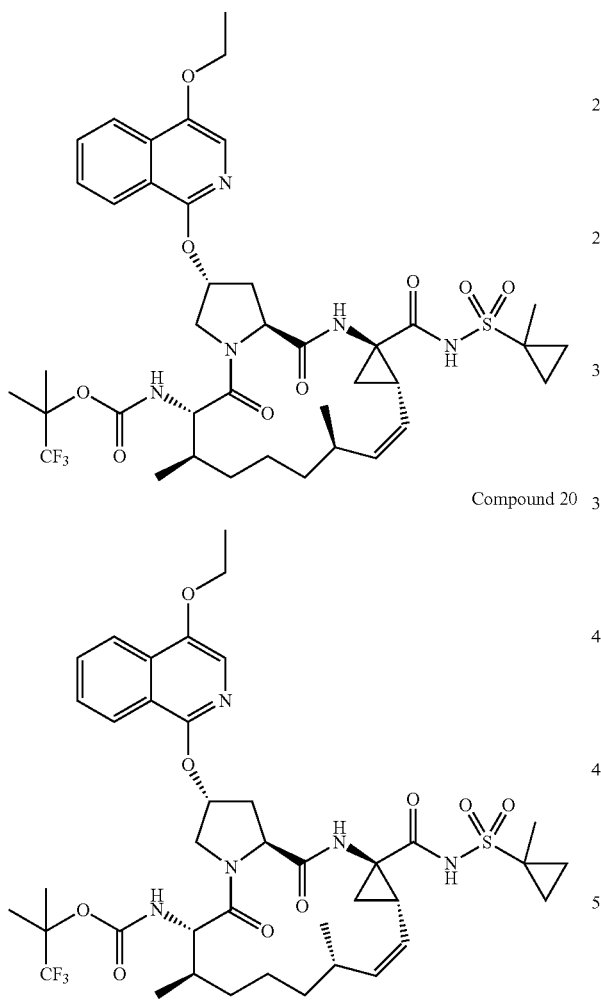

Compound 20

Compound 19 and Compound 20 were prepared using the intermediates described herein and by following the general procedure described for the synthesis of Compound 7 and Compound 8.

Compound 19: 1,1,1-trifluoro-2-methylpropan-2-yl (2R, 6S,7R,11R,13aS,14aR,16aS,Z)-2-(4-ethoxyisoquinolin-1-yloxy)-7,11-dimethyl-14a-(1-methylcyclopropylsulfonyl-carbamoyl)-5,16-dioxo-1,2,3,5,6,7,8,9,10,11,13a,14,14a,15, 16,16a-hexadecahydrocyclopropa[e]pyrrolo[1,2-a][1,4]diazacyclopentadecin-6-ylcarbamate. ¹H NMR (400 MHz, CD₃OD): δ ppm 8.16 (t, J=8.03 Hz, 2H) 7.74 (t, J=7.78 Hz, 1H) 7.54-7.60 (m, 2H) 5.83 (br. s., 1H) 5.37 (t, J=10.29 Hz, 1H) 5.00-5.06 (m, 1H) 4.69-4.77 (m, 2H) 4.25 (q, J=7.03 Hz, 2H) 4.02 (d, J=12.05 Hz, 1H) 3.87 (d, J=10.79 Hz, 1H) 2.58-2.75 (m, 3H) 2.35 (d, J=8.53 Hz, 1H) 1.73-1.84 (m, 1H) 1.58-1.70 (m, 5H) 1.53-1.57 (m, 6H) 1.40-1.51 (m, 2H) 1.31-1.37 (m, 4H) 1.28 (s, 1H) 1.09-1.21 (m, 1H) 0.98 (dd, J=6.27, 5.02 Hz, 6H) 0.91 (s, 5H); MS: MS m/z 836.5 (M⁺+1).

Compound 20: 1,1,1-trifluoro-2-methylpropan-2-yl (2R, 6S,7R,11S,13aS,14aR,16aS,Z)-2-(4-ethoxyisoquinolin-1-yloxy)-7,11-dimethyl-14a-(1-methylcyclopropylsulfonyl-carbamoyl)-5,16-dioxo-1,2,3,5,6,7,8,9,10,11,13a,14,14a,15, 16,16a-hexadecahydrocyclopropa[e]pyrrolo[1,2-a][1,4]diazacyclopentadecin-6-ylcarbamate. ¹H NMR (400 MHz, CD₃OD): δ ppm 8.16 (t, J=7.40 Hz, 2H) 7.74 (t, J=7.78 Hz, 1H) 7.53-7.59 (m, 2H) 5.83 (br. s., 1H) 5.36 (s, 1H) 4.93-4.99 (m, 1H) 4.69-4.79 (m, 2H) 4.24 (q, J=6.94 Hz, 2H) 4.04 (d, J=10.29 Hz, 1H) 3.85 (d, J=11.29 Hz, 1H) 2.63-2.79 (m, 3H) 2.42 (br. s., 1H) 1.85 (d, J=9.54 Hz, 1H) 1.62-1.77 (m, 3H) 1.52-1.59 (m, 6H) 1.39-1.49 (m, 3H) 1.36 (s, 3H) 1.27-1.32 (m, 3H) 1.17 (s, 1H) 0.89-1.01 (m, 11H). MS: MS m/z 836.4 (M⁺+1).

Preparation of Compound 21

Compound 21

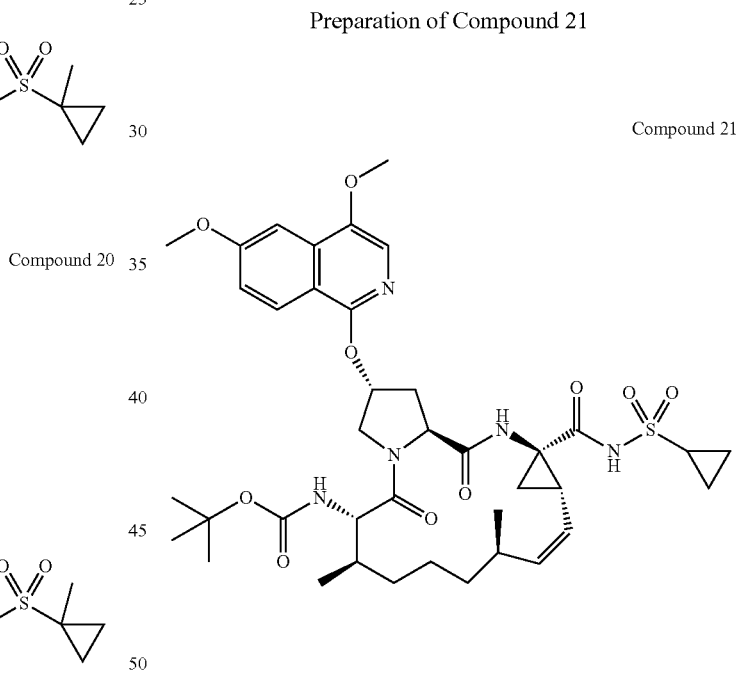

Compound 21 was prepared using the intermediates described herein and by following the general procedure described for the synthesis of Compound 5.

Compound 21: tert-butyl (2R,6S,7R,11R,13aS,14aR, 16aS,Z)-14a-(cyclopropylsulfonylcarbamoyl)-2-(4,6-dimethoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.06 (d, J=9.04 Hz, 1H) 7.51 (s, 1H) 7.42 (d, J=2.51 Hz, 1H) 7.13 (dd, J=9.03, 2.51 Hz, 1H) 5.81 (br. s., 1H) 5.37 (t, J=10.16 Hz, 1H) 5.01 (dd, J=10.54, 7.28 Hz, 1H) 4.62-4.69 (m, 2H) 3.98-4.04 (m, 4H) 3.89-3.96 (m, 4H) 3.18-3.25 (m, 1H) 2.89-2.97 (m, 1H) 2.55-2.70 (m, 2H) 2.38 (q, J=7.86 Hz, 1H) 1.77 (td, J=10.54, 6.27 Hz, 1H) 1.70 (dd, J=8.28, 5.27 Hz, 1H) 1.57-1.66 (m, 3H) 1.35-1.46 (m, 1H)

1.24-1.34 (m, 3H) 1.02-1.22 (m, 12H) 0.98 (t, J=6.53 Hz, 6H) 0.88-0.94 (m, 1H); MS: MS m/z 784.2 (M⁺+1).

Preparation of Compound 22

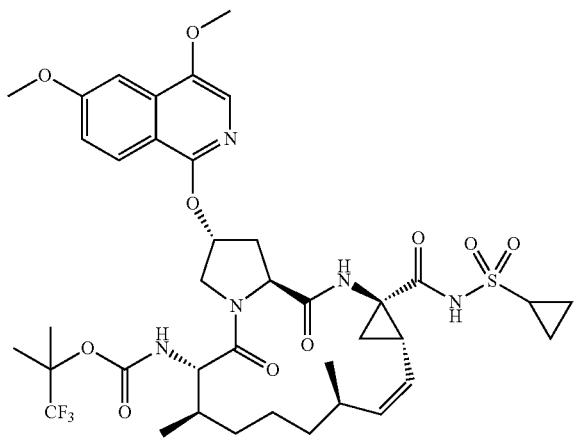 [SMILES: COc1ccc2c(O[C@@H]3C[C@H]4C(=O)N[C@]5(C(=O)NS(=O)(=O)C6CC6)C[C@H]5/C=C\[C@H](C)CCC[C@@H](C)[C@H](NC(=O)OC(C)(C)C(F)(F)F)C(=O)N4C3)ncc(OC)c2c1]

Compound 22 was prepared using the intermediates described herein and by following the general procedure described for the synthesis of Compound 7.

Compound 22: 1,1,1-trifluoro-2-methylpropan-2-yl (2R,6S,7R,11R,13aS,14aR,16aS,Z)-14a-(cyclopropylsulfonylcarbamoyl)-2-(4,6-dimethoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.06 (d, J=9.29 Hz, 1H) 7.53 (s, 1H) 7.43 (d, J=2.51 Hz, 1H) 7.15 (dd, J=9.16, 2.64 Hz, 1H) 5.81 (br. s., 1H) 5.37 (t, J=10.04 Hz, 1H) 5.00-5.06 (m, 1H) 4.67-4.73 (m, 2H) 3.97-4.04 (m, 4H) 3.95 (s, 3H) 3.83-3.89 (m, 1H) 3.22 (d, J=9.54 Hz, 1H) 2.94 (s, 1H) 2.56-2.71 (m, 2H) 2.36 (d, J=7.28 Hz, 1H) 1.75-1.84 (m, 1H) 1.71 (dd, J=8.03, 5.27 Hz, 1H) 1.56-1.66 (m, 3H) 1.39-1.46 (m, 1H) 1.37 (s, 3H) 1.24-1.32 (m, 2H) 1.03-1.22 (m, 4H) 0.98 (t, J=7.53 Hz, 9H) 0.88-0.93 (m, 1H); MS: MS m/z 838.2 (M⁺+1).

Preparation of Compound 23

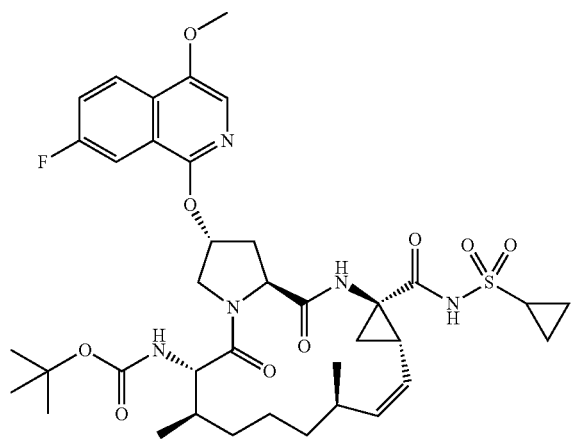 [SMILES: COc1cnc(O[C@@H]2C[C@H]3C(=O)N[C@]4(C(=O)NS(=O)(=O)C5CC5)C[C@H]4/C=C\[C@H](C)CCC[C@@H](C)[C@H](NC(=O)OC(C)(C)C)C(=O)N3C2)c2cc(F)ccc12]

Compound 23 was prepared using the intermediates described herein and by following the general procedure described for the synthesis of Compound 5.

Compound 23: tert-butyl (2R,6S,7R,11R,13aS,14aR,16aS,Z)-14a-(cyclopropylsulfonylcarbamoyl)-2-(7-fluoro-4-methoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 9.09 (s, 1H) 8.17 (dd, J=9.03, 5.27 Hz, 1H) 7.74 (dd, J=9.54, 2.51 Hz, 1H) 7.49-7.58 (m, 2H) 5.83 (br. s., 1H) 5.36 (t, J=10.67 Hz, 1H) 5.03 (t, J=10.67 Hz, 1H) 4.63-4.78 (m, 2H) 3.99-4.05 (m, 4H) 3.85 (d, J=10.54 Hz, 1H) 2.97 (tt, J=7.94, 4.86 Hz, 1H) 2.64-2.78 (m, 3H) 2.41 (ddd, J=13.80, 9.66, 4.14 Hz, 1H) 1.78-1.87 (m, 1H) 1.73 (dd, J=8.28, 5.77 Hz, 1H) 1.56-1.67 (m, 3H) 1.29-1.49 (m, 5H) 1.04-1.21 (m, 12H) 1.00 (d, J=6.53 Hz, 3H) 0.95 (d, J=6.27 Hz, 3H); MS: MS m/z 772.4 (M⁺+1).

Preparation of Compound 24

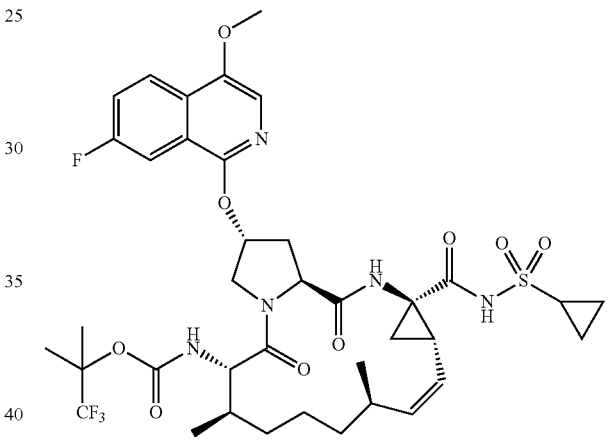

Compound 24 was prepared using the intermediates described herein and by following the general procedure described for the synthesis of Compound 7.

Compound 24: 1,1,1-trifluoro-2-methylpropan-2-yl (2R,6S,7R,11R,13aS,14aR,16aS,Z)-14a-(cyclopropylsulfonylcarbamoyl)-2-(7-fluoro-4-methoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 9.10 (s, 1H) 8.19 (dd, J=9.16, 5.40 Hz, 1H) 7.76 (dd, J=9.54, 2.51 Hz, 1H) 7.51-7.61 (m, 2H) 5.80-5.85 (m, 1H) 5.36 (t, J=10.54 Hz, 1H) 4.99-5.06 (m, 1H) 4.65-4.77 (m, 2H) 3.99-4.05 (m, 4H) 3.81 (d, J=10.29 Hz, 1H) 2.94-3.00 (m, 1H) 2.64-2.79 (m, 3H) 2.41 (ddd, J=13.80, 9.79, 4.27 Hz, 1H) 1.85 (d, J=6.27 Hz, 1H) 1.73 (dd, J=8.28, 5.77 Hz, 1H) 1.57-1.68 (m, 3H) 1.44 (d, J=12.05 Hz, 1H) 1.29-1.39

(m, 7H) 1.09-1.20 (m, 3H) 1.04-1.08 (m, 3H) 1.00 (d, J=6.53 Hz, 3H) 0.94 (d, J=6.53 Hz, 3H); MS: MS m/z 824.2 (M$^+$−1).

Preparation of Compound 25

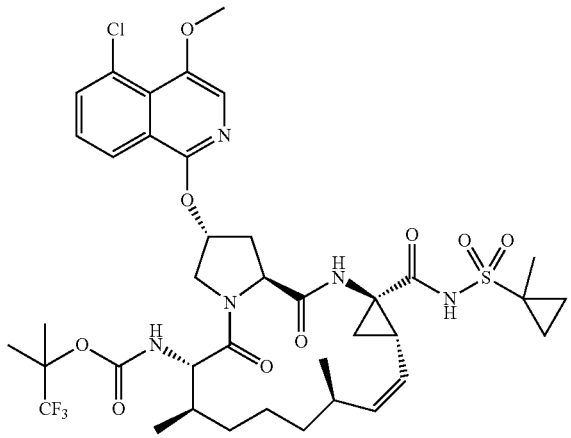 [SMILES: COc1cnc(O[C@@H]2C[C@H]3C(=O)N[C@]4(C(=O)NS(=O)(=O)C5(C)CC5)C[C@H]4/C=C\[C@H](C)CCC[C@@H](C)[C@H](NC(=O)OC(C)(C)C(F)(F)F)C(=O)N3C2)c2cccc(Cl)c12]

Compound 25 was prepared using the intermediates described herein and by following the general procedure described for the synthesis of Compound 7.

Compound 25: 1,1,1-trifluoro-2-methylpropan-2-yl (2R,6S,7R,11R,13aS,14aR,16aS,Z)-2-(5-chloro-4-methoxyisoquinolin-1-yloxy)-7,11-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.18 (dd, J=8.41, 1.13 Hz, 1H) 7.78 (dd, J=7.53, 1.00 Hz, 1H) 7.72 (s, 1H) 7.48 (t, J=8.03 Hz, 1H) 5.83 (br. s., 1H) 5.36 (t, J=9.91 Hz, 1H) 5.01-5.07 (m, 1H) 4.69-4.79 (m, 2H) 3.96-4.03 (m, 4H) 3.83 (d, J=10.79 Hz, 1H) 3.19 (br. s., 1H) 2.60-2.74 (m, 3H) 2.32 (br. s., 1H) 1.73-1.81 (m, 1H) 1.56-1.71 (m, 5H) 1.54 (s, 3H) 1.46-1.51 (m, 1H) 1.39 (br. s., 1H) 1.31-1.35 (m, 3H) 1.24 (d, J=7.28 Hz, 2H) 0.97 (t, J=6.02 Hz, 6H) 0.90 (s, 6H); MS: MS m/z 856.2 (M$^+$+1).

Preparation of Compound 26 and Compound 27

Compound 26

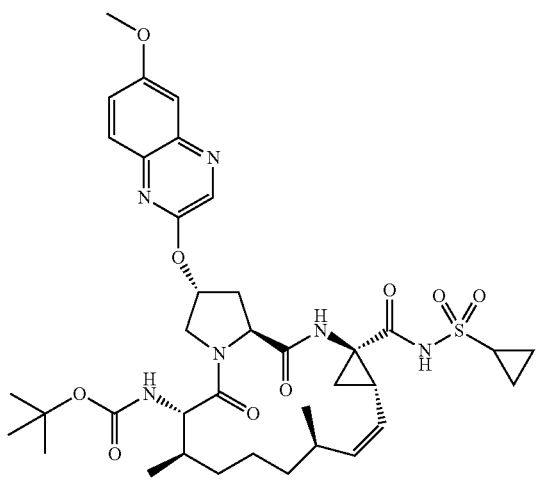

Compound 27

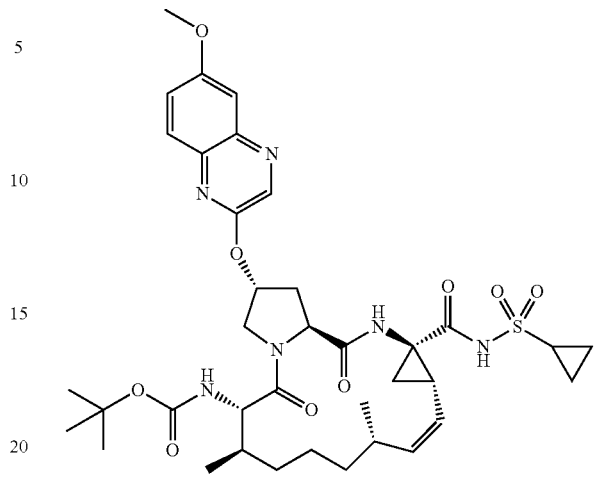

Compound 26 and Compound 27 were prepared using the intermediates described herein and by following the general procedure described for the synthesis of Compound 5 and Compound 6.

Compound 26: tert-butyl (2R,6S,7R,11R,13aS,14aR,16aS,Z)-14a-(cyclopropylsulfonylcarbamoyl)-2-(6-methoxyquinoxalin-2-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.86 (s, 1H) 8.37 (s, 1H) 7.82 (d, J=9.03 Hz, 1H) 7.36-7.44 (m, 2H) 5.87 (br. s., 1H) 5.37 (t, J=10.42 Hz, 1H) 5.02 (dd, J=10.54, 7.28 Hz, 1H) 4.64-4.73 (m, 2H) 4.04 (dd, J=11.80, 3.51 Hz, 1H) 3.95 (s, 3H) 3.84 (d, J=10.79 Hz, 1H) 3.18-3.23 (m, 1H) 2.90-2.98 (m, 1H) 2.64 (d, J=8.53 Hz, 2H) 2.31-2.38 (m, 1H) 1.68-1.80 (m, 2H) 1.55-1.67 (m, 3H) 1.36-1.45 (m, 1H) 1.22-1.34 (m, 2H) 1.15-1.22 (m, 2H) 1.02-1.13 (m, 11H) 0.98 (d, J=6.27 Hz, 3H) 0.94 (d, J=6.53 Hz, 3H) 0.86 (br. s., 1H); MS: MS m/z 755.4 (M$^+$+1).

Compound 27: tert-butyl (2R,6S,7R,11S,13aS,14aR,16aS,Z)-14a-(cyclopropylsulfonylcarbamoyl)-2-(6-methoxyquinoxalin-2-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.38 (s, 1H) 7.82 (d, J=9.03 Hz, 1H) 7.34-7.46 (m, 2H) 5.86 (br. s., 1H) 5.26-5.38 (m, 1H) 4.53-4.76 (m, 2H) 4.12 (q, J=7.28 Hz, 1H) 3.95 (s, 3H) 3.85 (d, J=10.29 Hz, 1H) 2.94 (br. s., 1H) 2.62-2.77 (m, 2H) 2.46 (br. s., 1H)

1.55-1.87 (m, 5H) 1.23-1.42 (m, 6H) 1.14 (s, 11H) 1.05 (dd, J=6.53, 4.02 Hz, 2H) 0.89-0.98 (m, 6H); MS: MS m/z 755.4 (M⁺+1).

Preparation of Compound 28 and Compound 29

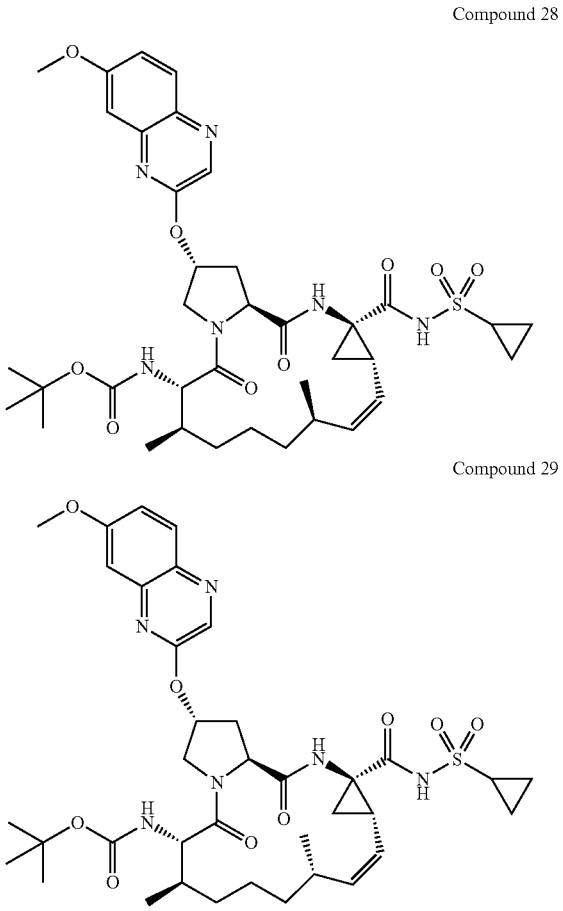

Compound 28

Compound 29

Compound 28 and Compound 29 were prepared using the intermediates described herein and by following the general procedure described for the synthesis of Compound 5 and Compound 6.

Compound 28: tert-butyl (2R,6S,7R,11R,13aS,14aR,16aS,Z)-14a-(cyclopropylsulfonylcarbamoyl)-2-(7-methoxyquinoxalin-2-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.24 (s, 1H) 7.86 (s, 1H) 7.23-7.33 (m, 2H) 5.89 (d, J=2.76 Hz, 1H) 5.36 (t, J=9.54 Hz, 1H) 5.05 (br. s., 1H) 4.62-4.75 (m, 2H) 4.07 (d, J=8.28 Hz, 1H) 3.98 (s, 3H) 3.85 (d, J=10.79 Hz, 1H) 2.93 (br. s., 1H) 2.60-2.72 (m, 2H) 2.31 (br. s., 1H) 1.68-1.82 (m, 2H) 1.54-1.67 (m, 3H) 1.36-1.48 (m, 1H) 1.16-1.32 (m, 5H) 1.11 (s, 11H) 0.96 (dd, J=18.82, 6.53 Hz, 6H) 0.81-0.91 (m, 1H); MS: MS m/z 755.4 (M⁺+1).

Compound 29: tert-butyl (2R,6S,7R,11S,13aS,14aR,16aS,Z)-14a-(cyclopropylsulfonylcarbamoyl)-2-(7-methoxyquinoxalin-2-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4] diazacyclopentadecin-6-ylcarbamate. ¹H NMR (400 MHz, CD₃OD): δ ppm 8.25 (s, 1H) 7.84 (d, J=9.03 Hz, 1H) 7.33 (d, J=2.51 Hz, 1H) 7.26 (dd, J=9.03, 2.76 Hz, 1H) 5.88 (br. s., 1H) 5.29 (br. s., 1H) 4.71 (d, J=11.54 Hz, 1H) 4.56-4.64 (m, 1H) 4.16 (br. s., 1H) 3.98 (s, 3H) 3.88 (d, J=10.29 Hz, 1H) 2.94 (br. s., 1H) 2.68 (dd, J=13.43, 7.91 Hz, 2H) 2.50 (br. s., 1H) 1.95-2.00 (m, 1H) 1.73-1.89 (m, 3H) 1.62 (br. s., 2H) 1.32 (d, J=12.05 Hz, 4H) 1.20-1.27 (m, 1H) 1.13 (s, 12H) 0.93-0.97 (m, 7H); MS: MS m/z 755.4 (M⁺+1).

Preparation of Compound 30 and Compound 31

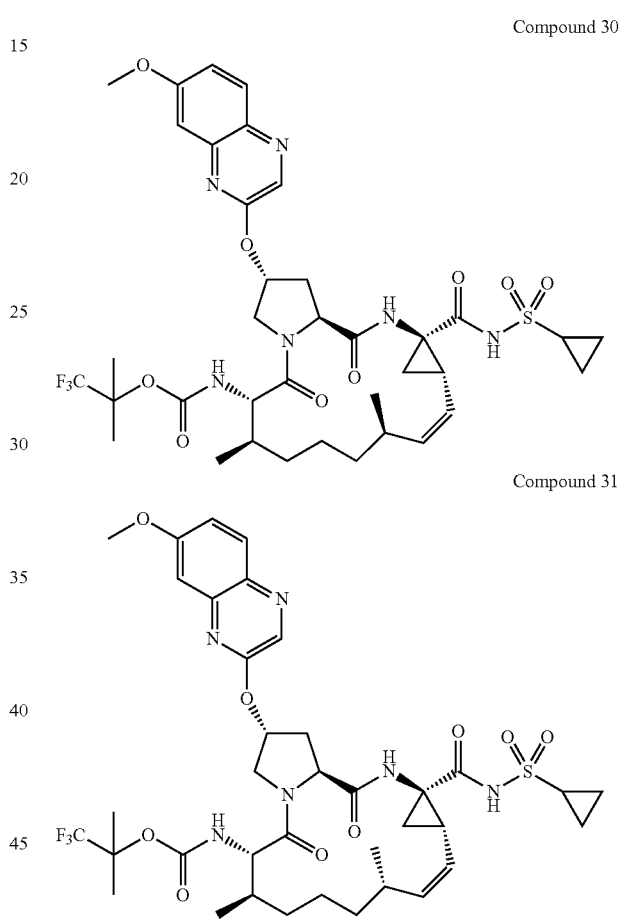

Compound 30

Compound 31

Compound 30 and Compound 31 were prepared using the intermediates described herein and by following the general procedure described for the synthesis of Compound 7 and Compound 8.

Compound 30: 1,1,1-trifluoro-2-methylpropan-2-yl (2R,6S,7R,11R,13aS,14aR,16aS,Z)-14a-(cyclopropylsulfonylcarbamoyl)-2-(7-methoxyquinoxalin-2-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. ¹H NMR (400 MHz, CD₃OD): δ ppm 8.89 (s, 1H) 8.26 (s, 1H) 7.87 (d, J=9.03 Hz, 1H) 7.25-7.35 (m, 2H) 5.88 (d, J=2.76 Hz, 1H) 5.33-5.41 (m, 1H) 5.03 (dd, J=10.67, 7.15 Hz, 1H) 4.76-4.81 (m, 1H) 4.69 (t, J=8.41 Hz, 1H) 3.96-4.07 (m, 4H) 3.81 (d, J=10.79 Hz, 1H) 3.23 (br. s., 2H) 2.90-3.00 (m, 1H) 2.66 (d, J=6.02 Hz, 2H) 2.29-2.38 (m, 1H) 1.54-1.82 (m, 5H) 1.40 (d, J=6.27 Hz, 1H) 1.28-1.35 (m, 3H) 1.25 (s, 3H) 1.03-1.22 (m, 5H) 0.84-1.02 (m, 7H); MS: MS m/z 809.2 (M⁺+1).

Compound 31: 1,1,1-trifluoro-2-methylpropan-2-yl (2R,6S,7R,11S,13aS,14aR,16aS,Z)-14a-(cyclopropylsulfonylcarbamoyl)-2-(7-methoxyquinoxalin-2-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.27 (s, 1H) 7.86 (d, J=9.03 Hz, 1H) 7.33 (d, J=2.76 Hz, 1H) 7.27 (dd, J=9.29, 2.76 Hz, 1H) 5.86 (br. s., 1H) 5.30 (br. s., 1H) 4.57-4.77 (m, 2H) 4.15 (br. s., 1H) 3.93-4.04 (m, 4H) 3.84 (d, J=10.79 Hz, 1H) 2.94 (br. s., 1H) 2.63-2.74 (m, 2H) 2.51 (d, J=14.31 Hz, 2H) 1.98 (s, 1H) 1.72-1.91 (m, 3H) 1.62 (br. s., 2H) 1.32 (d, J=12.30 Hz, 4H) 1.28 (s, 3H) 1.22 (s, 3H) 1.10 (d, J=4.52 Hz, 3H) 0.95 (t, J=6.02 Hz, 6H); MS: MS m/z 807.2 (M$^+$−1).

Preparation of Compound 32

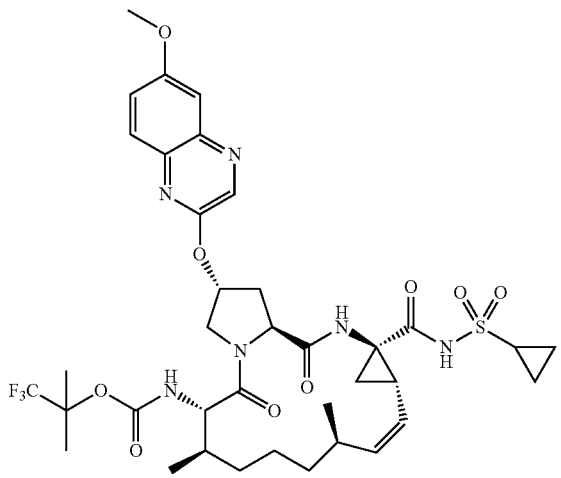 [SMILES: COc1ccc2nc(O[C@@H]3C[C@H]4C(=O)N[C@]5(C(=O)NS(=O)(=O)C6CC6)C[C@H]5/C=C\[C@H](C)CCC[C@@H](C)[C@H](NC(=O)OC(C)(C)C(F)(F)F)C(=O)N4C3)cnc2c1]

Compound 32 was prepared using the intermediates described herein and by following the general procedure described for the synthesis of Compound 7.

Compound 32: 1,1,1-trifluoro-2-methylpropan-2-yl (2R,6S,7R,11R,13aS,14aR,16aS,Z)-14a-(cyclopropylsulfonylcarbamoyl)-2-(6-methoxyquinoxalin-2-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.88 (s, 1H) 8.39 (s, 1H) 7.92 (s, 1H) 7.83 (d, J=9.03 Hz, 1H) 7.39-7.45 (m, 2H) 5.86 (br. s., 1H) 5.34-5.40 (m, 1H) 5.03 (dd, J=10.79, 7.78 Hz, 2H) 4.66-4.77 (m, 2H) 4.02 (dd, J=11.92, 3.39 Hz, 1H) 3.78-3.84 (m, 1H) 3.20 (br. s., 1H) 2.91-2.98 (m, 1H) 2.63-2.68 (m, 2H) 2.29-2.35 (m, 1H) 1.55-1.80 (m, 5H) 1.39 (br. s., 1H) 1.28-1.35 (m, 2H) 1.24-1.28 (m, 4H) 1.22 (s, 3H) 1.04-1.20 (m, 4H) 0.99 (d, J=6.53 Hz, 3H) 0.94 (d, J=6.53 Hz, 3H) 0.87 (br. s., 1H); MS: MS m/z 809.4 (M$^+$+1).

Preparation of Compound 33

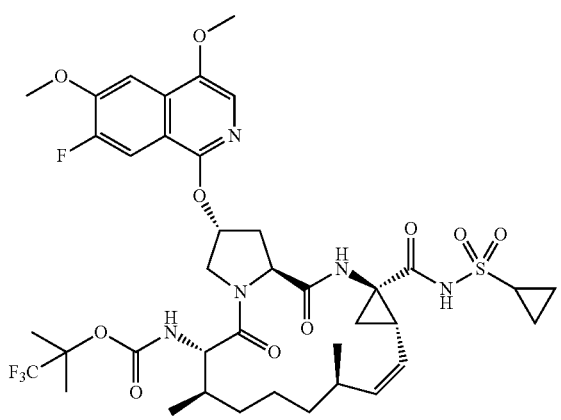 [SMILES: COc1cc2c(OC)cnc(O[C@@H]3C[C@H]4C(=O)N[C@]5(C(=O)NS(=O)(=O)C6CC6)C[C@H]5/C=C\[C@H](C)CCC[C@@H](C)[C@H](NC(=O)OC(C)(C)C(F)(F)F)C(=O)N4C3)c2cc1F]

Compound 33 was prepared using the intermediates described herein and by following the general procedure described for the synthesis of Compound 7.

Compound 33: 1,1,1-trifluoro-2-methylpropan-2-yl (2R,6S,7R,11R,13aS,14aR,16aS,Z)-14a-(cyclopropylsulfonylcarbamoyl)-2-(7-fluoro-4,6-dimethoxyisoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 7.74 (d, J=11.54 Hz, 1H) 7.57 (d, J=8.28 Hz, 1H) 7.54 (s, 1H) 5.81 (br. s., 1H) 5.37 (t, J=10.42 Hz, 1H) 5.02 (dd, J=10.42, 7.40 Hz, 1H) 4.64-4.71 (m, 2H) 4.03 (d, J=1.25 Hz, 6H) 3.95-4.00 (m, 1H) 3.82-3.87 (m, 1H) 3.22 (d, J=6.53 Hz, 1H) 2.90-2.97 (m, 1H) 2.57 (d, J=4.27 Hz, 2H) 2.31-2.38 (m, 1H) 1.74-1.82 (m, 1H) 1.70 (dd, J=8.03, 5.27 Hz, 1H) 1.57-1.66 (m, 3H) 1.38 (s, 3H) 1.23-1.33 (m, 3H) 1.10-1.22 (m, 3H) 1.02-1.09 (m, 4H) 0.98 (dd, J=6.53, 3.76 Hz, 6H) 0.93 (d, J=6.53 Hz, 1H); MS: MS m/z 856.2 (M$^+$+1).

Preparation of Compound 34

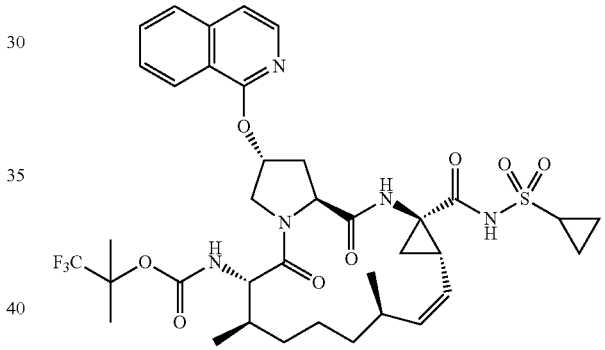

Compound 34 was prepared using the intermediates described herein and by following the general procedure described for the synthesis of Compound 7.

Compound 34: 1,1,1-trifluoro-2-methylpropan-2-yl (2R,6S,7R,11R,13aS,14aR,16aS,Z)-14a-(cyclopropylsulfonylcarbamoyl)-2-(isoquinolin-1-yloxy)-7,11-dimethyl-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.22 (d, J=8.78 Hz, 1H) 8.00 (d, J=6.02 Hz, 1H) 7.92 (s, 2H) 7.83 (d, J=8.03 Hz, 1H) 7.72 (td, J=7.53, 1.25 Hz, 1H) 7.54 (t, J=7.15 Hz, 1H) 7.34 (d, J=5.77 Hz, 1H) 5.90 (br. s., 1H) 5.36 (t, J=10.04 Hz, 1H) 5.04 (br. s., 2H) 4.72-4.81 (m, 3H) 4.62 (s, 1H) 4.01 (br. s., 1H) 3.85 (d, J=10.79 Hz, 1H) 2.94 (br. s., 1H) 2.61-2.76 (m, 2H) 1.74-1.82 (m, 1H) 1.68-1.73 (m, 1H) 1.64 (dd, J=9.54, 5.27 Hz, 3H) 1.41 (br. s., 1H) 1.30 (s, 3H) 1.23-1.28 (m, 1H) 1.19 (d, J=8.28 Hz, 4H) 0.98 (dd, J=9.03, 6.53 Hz, 6H) 0.90-0.94 (m, 1H) 0.87 (s, 3H); MS: MS m/z 776.2 (M$^+$−1).

Preparation of Compound 35

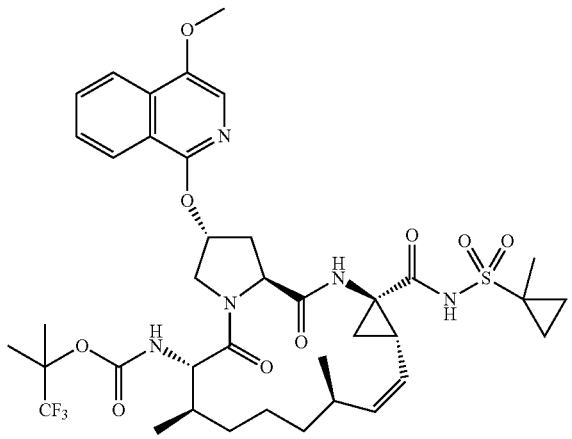 [SMILES: COc1cnc(O[C@@H]2C[C@H]3C(=O)N[C@]4(C(=O)NS(=O)(=O)C5(C)CC5)C[C@H]4/C=C\[C@H](C)CCC[C@@H](C)[C@H](NC(=O)OC(C)(C)C(F)(F)F)C(=O)N3C2)c2ccccc12]

Compound 35 was prepared using the intermediates described herein and by following the general procedure described for the synthesis of Compound 7.

Compound 35: 1,1,1-trifluoro-2-methylpropan-2-yl (2R,6S,7R,11R,13aS,14aR,16aS,Z)-2-(4-methoxyisoquinolin-1-yloxy)-7,11-dimethyl-14a-(1-methylcyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate. $^1$H NMR (400 MHz, CD$_3$OD): δ ppm 8.14 (dd, J=17.69, 8.16 Hz, 2H) 7.74 (ddd, J=8.28, 7.03, 1.25 Hz, 1H) 7.55-7.59 (m, 2H) 5.83 (br. s., 1H) 5.36 (t, J=10.29 Hz, 1H) 5.03 (br. s., 1H) 4.74 (d, J=10.29 Hz, 2H) 4.03 (s, 3H) 3.86 (d, J=10.54 Hz, 1H) 3.21 (d, J=18.07 Hz, 1H) 2.58-2.74 (m, 2H) 2.34 (br. s., 1H) 1.74-1.83 (m, 1H) 1.56-1.70 (m, 5H) 1.53 (s, 3H) 1.38-1.50 (m, 3H) 1.31-1.35 (m, 3H) 1.13-1.29 (m, 3H) 0.97 (t, J=6.02 Hz, 6H) 0.90 (s, 5H); MS: MS m/z 823.4 (M$^+$+1).

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, *J. Clin. Microbiol.,* 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, *J. Proc. Natl. Acad. Sci. U.S.A.* 94(16), 8738-8743 (1997); AF054247, see Yanagi, M., St Claire, M., Shapiro, M., Emerson, S. U., Purcell, R. H. and Bukh, J., *Virology* 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. *Biochemistry.* 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., *J Virol.* 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-N'-(2-Ethane Sulfonic acid) (HEPES), pH 7.5, 20% glycerol, 500 mM Sodium Chloride (NaCl), 0.5% Triton X-100, 1 microgram/milliliter ("μg/mL") lysozyme, 5 mM Magnesium Chloride (MgCl$_2$), 1 μg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM (βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS- PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET 51 (Resonance Energy Transfer Depsipeptide Substrate; AnaSpec, Inc. cat #22991) (FRET peptide), described by Taliani et al. in *Anal. Biochem.* 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y=A+((B-A)/(1+((C/x)^D)))$.

Compounds of the present disclosure, which were tested against more than one type of NS3/4A complex, were found to have similar inhibitory properties though the compounds uniformly demonstrated greater potency against the 1b strains as compared to the 1a strains.

Generation of HCV Replicon

An HCV replicon whole cell system was established as described by Lohmann V, Korner F, Koch J, Herian U, Theilmann L, Bartenschlager R., Science 285(5424):110-3 (1999) and modified to introduce a luciferase reporter, as first described by Krieger et al (Krieger N, Lohmann V, and Bartenschlager R, *J. Virol.* 75(10):4614-4624 (2001)). CDNA encoding a humanized form of the *Renilla luciferase* gene and a linker sequence fused directly to the 3'-end of the luciferase gene were introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, *Science* 290(5498):1972-1974). A stable cell line constitutively expressing this HCV replicon construct was generated by first linearizing plasmid DNAs with ScaI. RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

A stable HCV replicon luciferase reporter cell line representing the genotype 1a H77 strain (Yanagi M, Purcell R H, Emerson S U, et al. Transcripts from a single full-length cDNA clone of hepatitis C virus are infectious when directly transfected into the liver of a chimpanzee. Proc Natl Acad Sci USA 1997; 94(16):8738-8743) was generated as described previously for the genotype 1b (Con1) replicon luciferase cell line. The replicon construct was modified by introducing mutations were introduced into the genes encoding the NS3 helicase domain (proline replaced by leucine at position 1496) and NS5A (serine to isoleucine at position 2204) to improve replication in cell culture.

HCV Replicon Luciferase Reporter Assay

HCV replicon luciferase assays were developed to monitor the inhibitory effects of compounds described in the disclosure on HCV genotypes 1a and 1b viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/mL G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 µL of cells at a density of $3.0\times10^3$ cells/well in DMEM containing 4% FCS (final DMSO concentration at 0.5%). After 3 days incubation at 37° C., cells were analyzed for Renilla Luciferase activity using the EnduRen as substrate (Promega cat #E6485). The EnduRen substrate was diluted in DMEM and then added to the plates to a final concentration of 7.5 µM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat #G8082). Cell-Titer Blue (3 µL) was added to each well and incubated for 8 hrs at 37° C. The fluorescence signal from each well was read, with an excitation wavelength at 525/10 nm and an emission wavelength of 598/10 nm, using the Viewlux Imager.

The $EC_{50}$ values for compounds were calculated by using a four-parameter logistic equation:

$$y = A + ((B-A)/(1+((C/x)^{\wedge}D)))$$, where A and B denotes minimal and maximal % inhibition, respectively, C is the $EC_{50}$, D is the hill slope and x represents compound concentration.

Table 2 shows the $EC_{50}$ values of representative compounds of the present disclosure. Ranges are as follows: A=0.20 nM-1.0 nM; B=1.01 nM-2.0 nM; C=2.01 nM-5.0 nM; D=5.01 nM-68 nM.

TABLE 2

| Compound Number | Genotype 1a $EC_{50}$ (nM) | Genotype 1b $EC_{50}$ (nM) |
|---|---|---|
| 3 | A | A |
| 4 | 4.9 | 2.8 |
| 5 | 0.41 | 1.2 |
| 6 | B | C |
| 7 | B | A |
| 8 | C | B |
| 9 | 1.0 | 0.36 |
| 11 | C | A |
| 12 | C | B |
| 13 | D | C |
| 14 | C | B |
| 15 | B | B |
| 17 | D | D |
| 18 | D | D |
| 19 | C | B |
| 21 | B | A |
| 22 | B | A |
| 23 | D | D |
| 24 | D | D |
| 25 | B | A |
| 26 | 214.8 | 86.5 |
| 27 | D | D |
| 28 | D | B |
| 29 | D | D |
| 30 | C | A |
| 31 | D | D |
| 32 | D | D |
| 33 | C | B |
| 34 | C | A |
| 35 | 1.96 | 0.51 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A compound of formula (I)

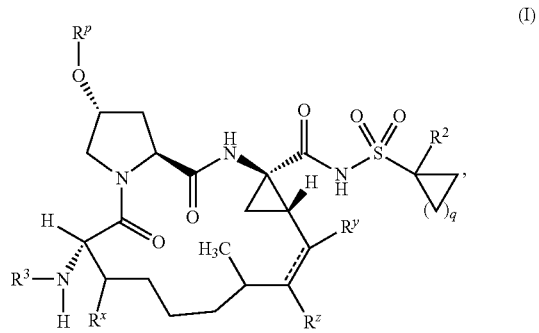

or a pharmaceutically acceptable salt thereof, wherein
q is 1 or 2;
⸺ is a single or double bond;
$R^p$ is selected from

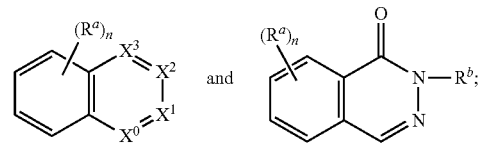

wherein $R^p$ is attached to the parent molecular moiety through any substitutable carbon atom in the group;
n is 0, 1, 2, 3, 4, 5, or 6;
$X^0$ is selected from CH and N;
$X^1$ is selected from CH and N;
$X^2$ and $X^3$ are independently selected from CH, C($R^a$) and N; provided that at least one of $X^1$, $X^2$, and $X^3$ is other than N;
each $R^a$ is independently selected from alkenyloxy, alkoxy, alkoxyalkoxy, alkyl, benzodioxanyl, carboxamido, carboxy, carboxyalkoxy, cyano, cycloalkylalkoxy, cycloalkyloxy, deuteroalkoxy, dialkylamino, halo, haloalkyl, haloalkoxy, haloalkoxycarbonyl, hydroxy, morpholinyl, phenyl, piperazinyl, pyrazolyl, pyridinyl, and pyrrolidinyl, wherein the morpholinyl, the phenyl, the piperazinyl, the pyridinyl, and the pyrrolidinyl are optionally substituted with one or two groups independently selected from alkoxy, alkyl, alkylsulfonyl, halo, haloalkoxy, haloalkyl, and morpholinyl; and wherein two adjacent $R^a$ groups, together with the carbon atoms to which they are attached, can optionally form a ring selected from dioxanyl, dioxolanyl, morpholinyl, pyranyl, and phenyl, wherein the ring is optionally substituted with one or two groups independently selected from alkyl and halo;
$R^b$ is alkyl;
$R^x$ is selected from methyl and ethyl;
$R^y$ and $R^z$ are independently selected from hydrogen and hydroxy; provided that when ⸺ is a double bond, $R^y$ and $R^z$ are each hydrogen;
$R^2$ is selected from hydrogen, alkyl, halo, haloalkoxy, haloalkyl, and hydroxyalkyl; and
$R^3$ is selected from hydrogen, alkoxyalkoxycarbonyl, alkoxycarbonyl, alkylaminocarbonyl, alkylcarbonyl, cycloalkylalkoxycarbonyl, cycloalkylcarbonyl, cycloalkyloxycarbonyl, deuteroalkoxycarbonyl, deuterohaloalkoxycarbonyl, dialkylaminocarbonyl, dialkylaminocarbonylcarbonyl, haloalkoxycarbonyl, haloalkylaminocarbonyl, haloalkylcarbonyl, heterocyclylcarbonyl, heterocyclyloxycarbonyl, phenylcarbonyl, and phenyloxycarbonyl, wherein the cycloalkyl part of the cycloalkylalkoxycarbonyl, the cycloalkylcarbonyl, and the cycloalkyloxycarbonyl, the heterocyclyl part of the heterocyclylcarbonyl and the heterocyclyloxycarbonyl, and the phenyl part of the phenylcarbonyl and the phenyloxycarbonyl, is optionally substituted with one, two, or three groups independently selected from alkyl, alkylamino, alkylcarbonyl, cycloalkyl, dialkylamino, halo, haloalkoxy, and haloalkyl.

2. A compound of claim 1, or a pharmaceutically acceptable salt thereof, wherein:
q is 1;
═══ is a double bond;
$R^x$ is methyl; and
$R^y$ and $R^z$ are each hydrogen.

3. A compound of claim 1, or a pharmaceutically acceptable salt thereof, wherein $R^p$ is:

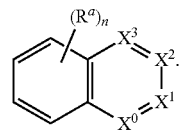

4. A compound of claim 2, or a pharmaceutically acceptable salt thereof, wherein
n is 0, 1, 2, or 3;
each $R^a$ is independently selected from alkoxy, and halo; and
$R^3$ is selected from alkoxycarbonyl and haloalkoxycarbonyl.

5. A compound of formula (II)

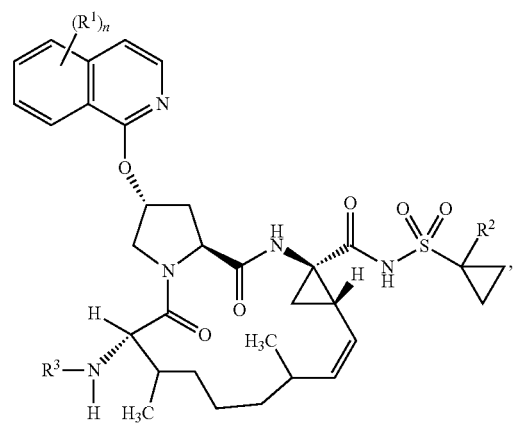

or a pharmaceutically acceptable salt thereof, wherein
n is 0, 1, 2, 3, 4, 5, or 6;
each $R^1$ is independently selected from alkoxy, alkyl, carboxamido, carboxy, cyano, cycloalkyloxy, dialkylamino, halo, haloalkyl, haloalkoxy, and phenyl, wherein the phenyl is optionally substituted with one or two groups independently selected from alkoxy, alkyl, halo, haloalkoxy, and haloalkyl;
$R^2$ is selected from hydrogen, alkyl, halo, and haloalkyl; and $R^3$ is selected from alkoxycarbonyl, alkylcarbonyl, haloalkoxycarbonyl, haloalkylcarbonyl, and phenylcarbonyl, wherein the phenyl is optionally substituted with one or two groups independently selected from alkyl and halo.

6. A compound selected from

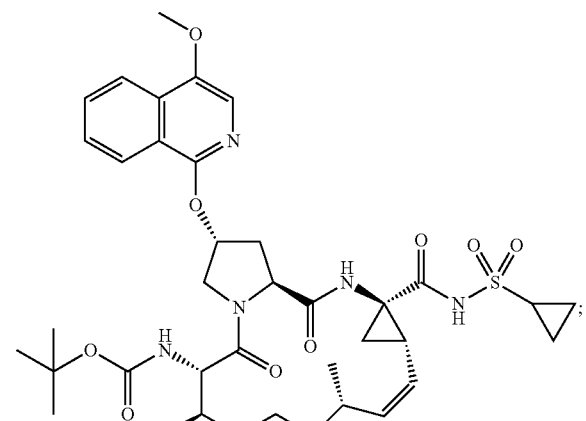

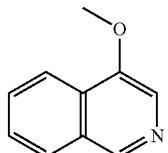

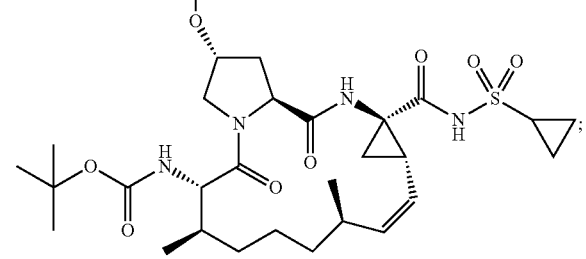

75
-continued
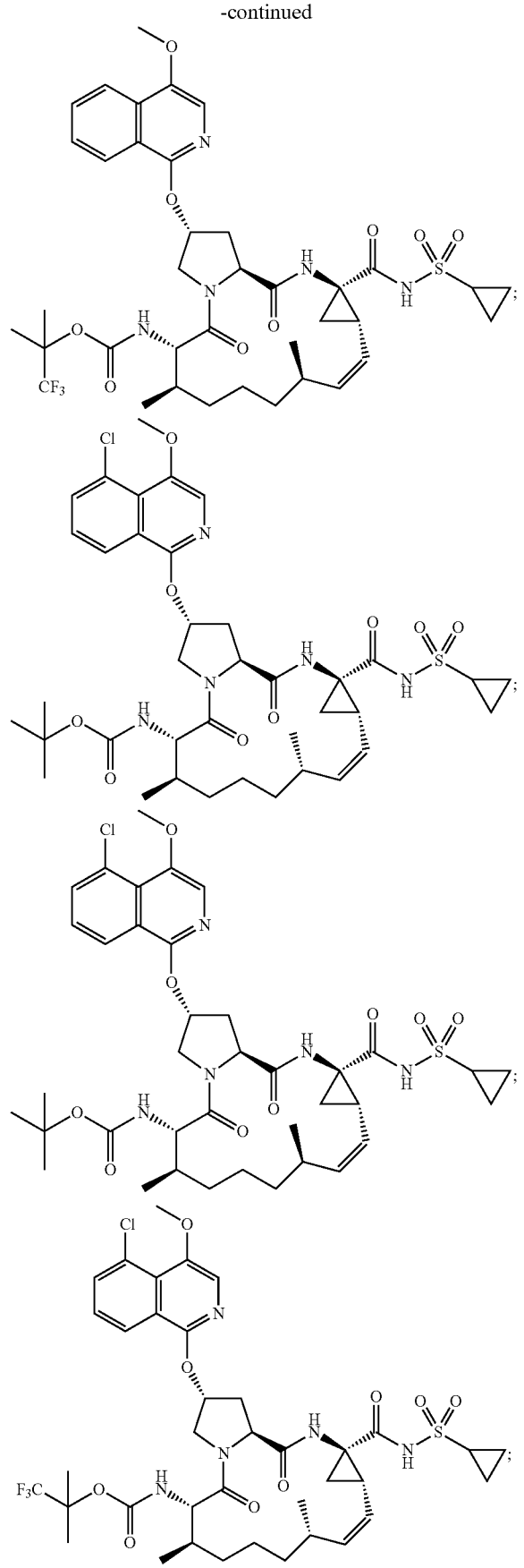
76
-continued
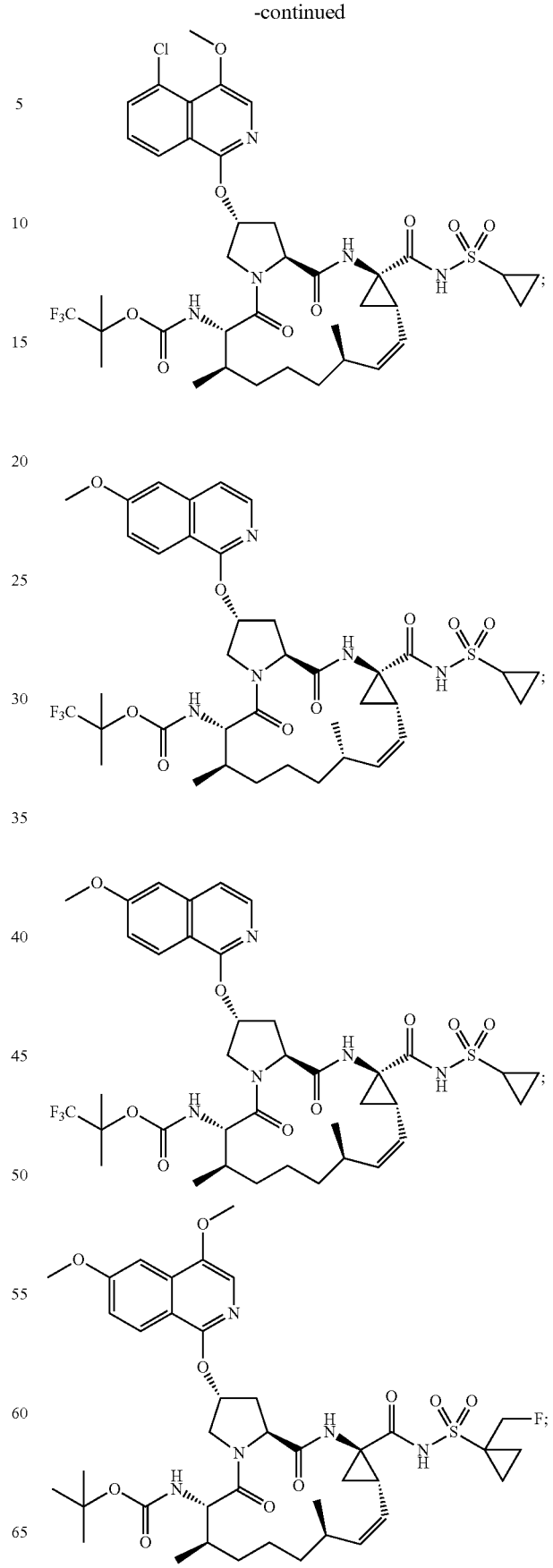

77
-continued
78
-continued
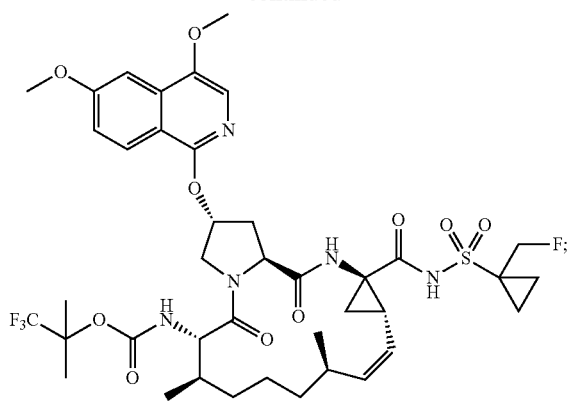
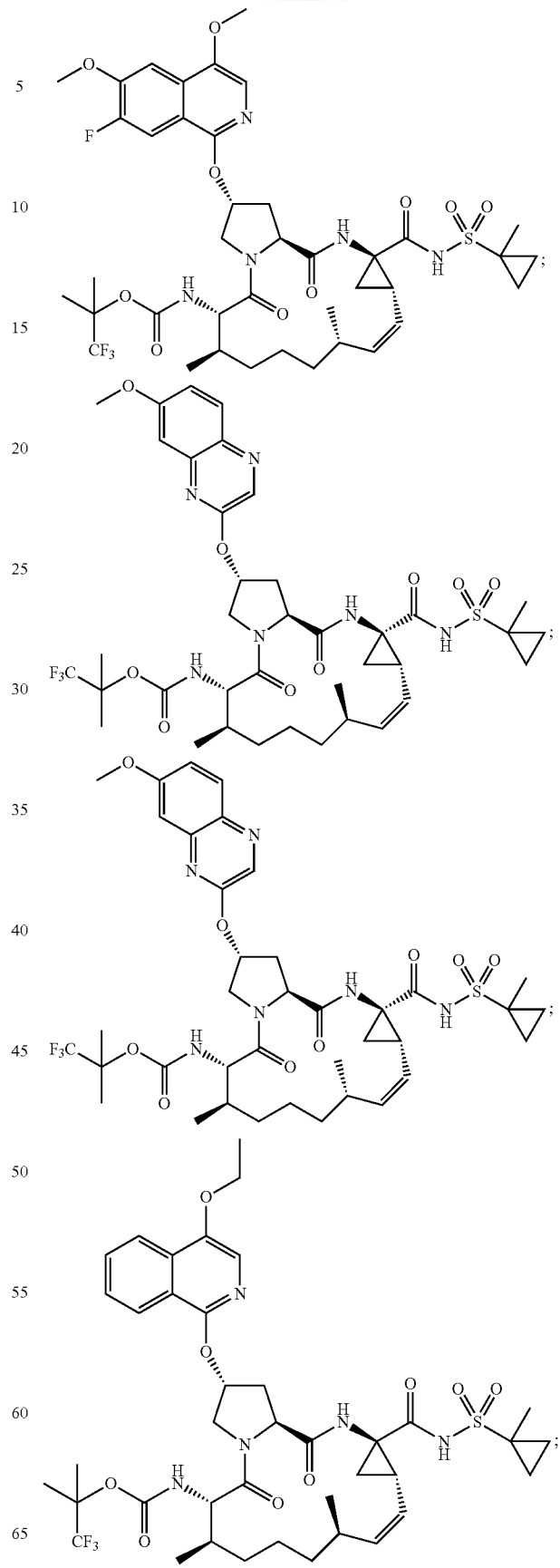

79
-continued
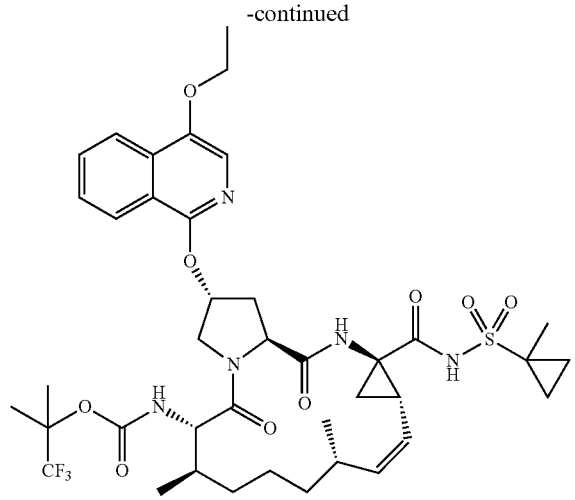
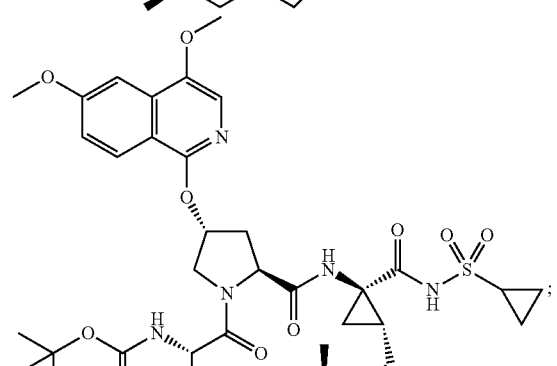
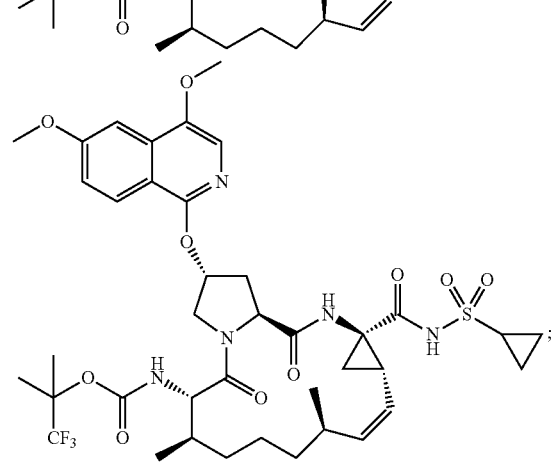
80
-continued
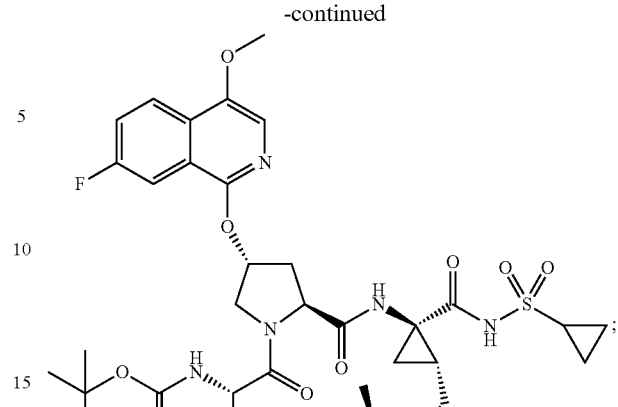
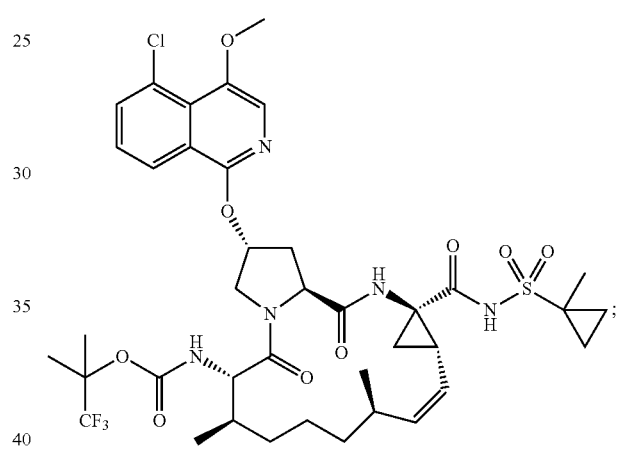
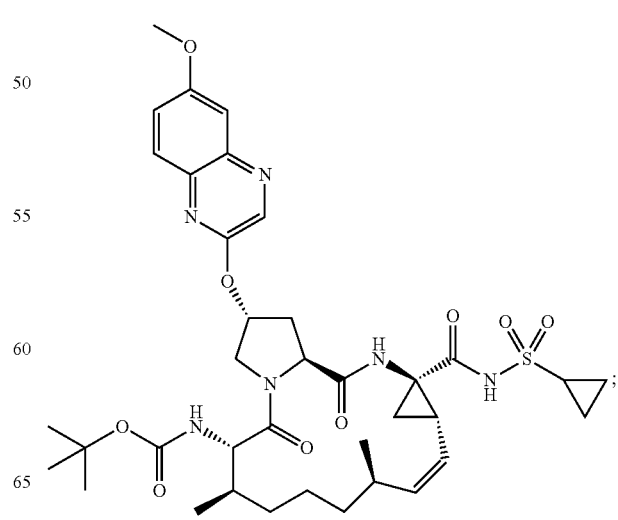

81
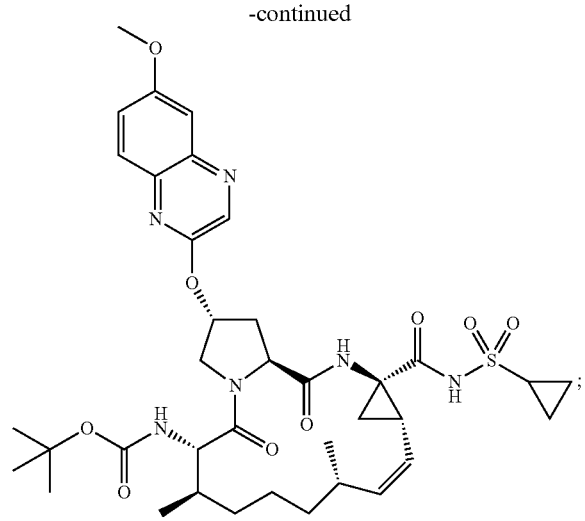
82
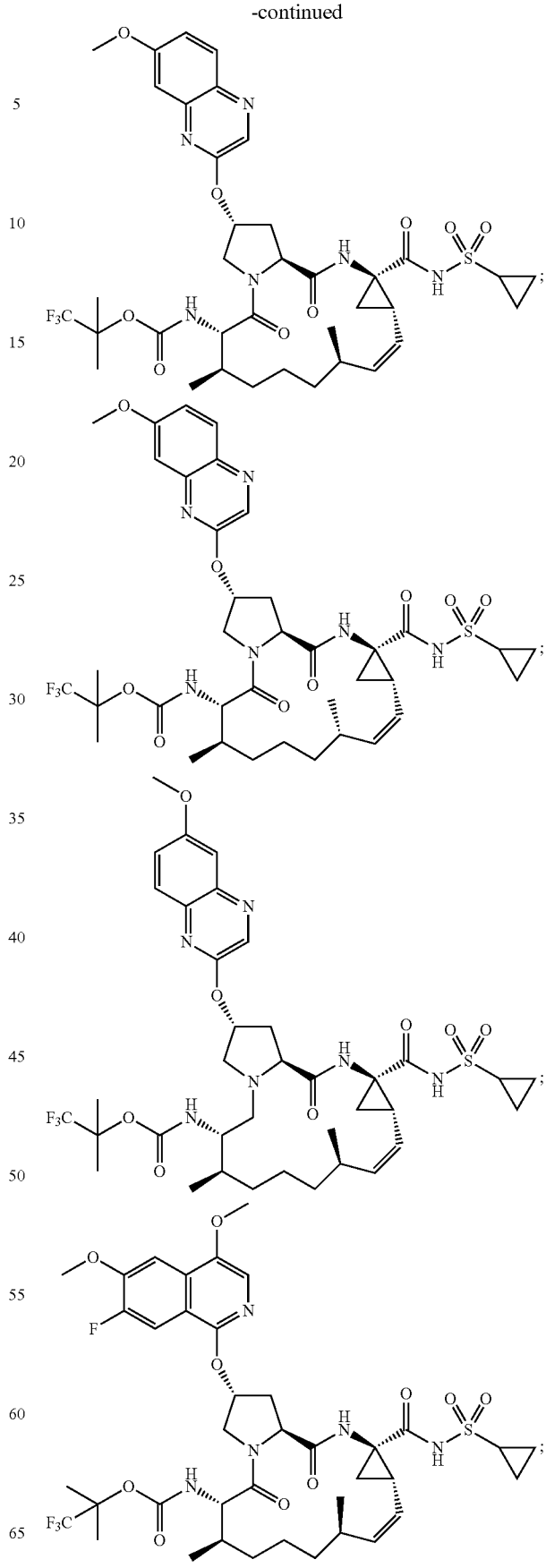

-continued

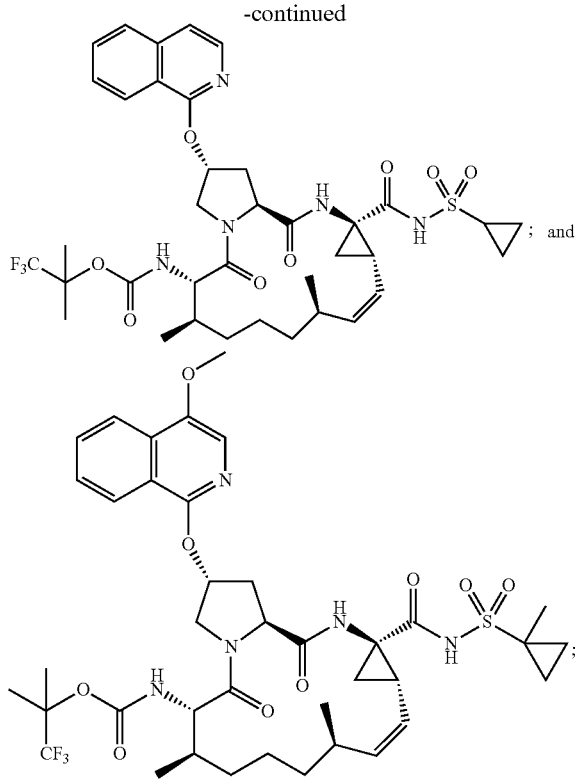

or a pharmaceutically acceptable salt thereof.

7. A composition comprising a compound of formula (I), or a pharmaceutically acceptable salt thereof, and a pharmaceutically acceptable carrier.

8. The composition of claim 7 further comprising at least one additional compound having anti-HCV activity.

9. The composition of claim 8 wherein at least one of the additional compounds is an interferon or a ribavirin.

10. The composition of claim 9 wherein the interferon is selected from interferon alpha 2B, pegylated interferon alpha, consensus interferon, interferon alpha 2A, and lymphoblastiod interferon tau.

11. The composition of claim 8 wherein at least one of the additional compounds is selected from interleukin 2, interleukin 6, interleukin 12, Imiquimod, ribavirin, an inosine 5'-monophospate dehydrogenase inhibitor, amantadine, and rimantadine.

12. The composition of claim 8 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

13. A method of treating an HCV infection in a patient, comprising administering to the patient a therapeutically effective amount of a compound of formula (I), or a pharmaceutically acceptable salt thereof.

14. The method of claim 13 further comprising administering at least one additional compound having anti-HCV activity prior to, after, or simultaneously with the compound of formula (I), or a pharmaceutically acceptable salt thereof.

15. The method of claim 14 wherein at least one of the additional compounds is an interferon or a ribavirin.

16. The method of claim 15 wherein the interferon is selected from interferon alpha 2B, pegylated interferon alpha, consensus interferon, interferon alpha 2A, and lymphoblastiod interferon tau.

17. The method of claim 14 wherein at least one of the additional compounds is selected from interleukin 2, interleukin 6, interleukin 12, Imiquimod, ribavirin, an inosine 5'-monophospate dehydrogenase inhibitor, amantadine, and rimantadine.

18. The method of claim 14 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

\* \* \* \* \*

UNITED STATES PATENT AND TRADEMARK OFFICE
CERTIFICATE OF CORRECTION

PATENT NO.      : 8,691,757 B2
APPLICATION NO. : 13/492982
DATED           : April 8, 2014
INVENTOR(S)     : Ramkumar Rajamani et al.

Page 1 of 1

It is certified that error appears in the above-identified patent and that said Letters Patent is hereby corrected as shown below:

In the Specification:

Column 4, lines 48 and 49, change "lymphoblastiod" to -- lymphoblastoid --.

Column 5, line 14, change "lymphoblastiod" to -- lymphoblastoid --.

In the Claims:

Claim 10:

Column 84, lines 3 and 4, change "lymphoblastiod" to -- lymphoblastoid --.

Claim 11:

Column 84, line 8, change "5′-monophospate" to -- 5′-monophosphate --.

Claim 16:

Column 84, lines 27 and 28, change "lymphoblastiod" to -- lymphoblastoid --.

Claim 27:

Column 84, line 32, change "5′-monophospate" to -- 5′-monophosphate --.

Signed and Sealed this
Seventh Day of April, 2015

Michelle K. Lee
*Director of the United States Patent and Trademark Office*